(12) United States Patent
Alvizo et al.

(10) Patent No.: US 12,410,410 B2
(45) Date of Patent: Sep. 9, 2025

(54) KETOREDUCTASE POLYPEPTIDES FOR THE SYNTHESIS OF CHIRAL COMPOUNDS

(71) Applicant: Codexis, Inc., Redwood City, CA (US)

(72) Inventors: Oscar Alvizo, Fremont, CA (US); Nicholas J. Agard, San Francisco, CA (US); Xinkai Xie, Castro Valley, CA (US); David Entwistle, San Carlos, CA (US); Birgit Kosjek, Westfield, NJ (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 17/553,455

(22) Filed: Dec. 16, 2021

(65) Prior Publication Data

US 2022/0106575 A1 Apr. 7, 2022

Related U.S. Application Data

(60) Continuation of application No. 16/874,574, filed on May 14, 2020, now Pat. No. 11,236,308, which is a division of application No. 15/543,535, filed as application No. PCT/US2016/016692 on Feb. 5, 2016, now Pat. No. 10,696,953.

(60) Provisional application No. 62/114,380, filed on Feb. 10, 2015.

(51) Int. Cl.
| | | |
|---|---|---|
| C12N 9/04 | (2006.01) | |
| C12P 7/02 | (2006.01) | |
| C12P 7/40 | (2006.01) | |
| C12P 17/12 | (2006.01) | |
| C12P 41/00 | (2006.01) | |

(52) U.S. Cl.
CPC .............. *C12N 9/0006* (2013.01); *C12P 7/02* (2013.01); *C12P 7/40* (2013.01); *C12P 17/12* (2013.01); *C12P 41/002* (2013.01); *C12Y 101/01184* (2013.01)

(58) Field of Classification Search
None
See application file for complete search history.

(56) References Cited

U.S. PATENT DOCUMENTS

| | | |
|---|---|---|
| 5,538,867 A | 7/1996 | Durliat et al. |
| 5,559,030 A | 9/1996 | Matsuyama et al. |
| 5,605,793 A | 2/1997 | Stemmer |
| 5,700,670 A | 12/1997 | Yamagishi et al. |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,891,685 A | 4/1999 | Yamagishi et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |

(Continued)

FOREIGN PATENT DOCUMENTS

| | | |
|---|---|---|
| WO | 95/22625 A1 | 8/1995 |
| WO | 95/33836 A1 | 12/1995 |

(Continued)

OTHER PUBLICATIONS

UniProtKB/Swiss-Prot No. P14941 dated May 10, 2017.
Grau, B.T., et al., "Chemo- and Enantioselective Routes to Chiral Fluorinated Hydroxyketones Using Ketoreductases," Organic Letters, 9(24):4951-4954 [2007].
Ngo, J.T., et al., "Computational Complexity, Protein Structure Prediction and the Levinthal Paradox" in The Protein Folding Problem and Tertiary Structure Prediction, Merz et al. (ed.), Birkhauser, Boston, MA, pp. 433 and 492-495 [1994].
Altschul, S., et al., "Basic local alignment search tool," J. Mol. Biol., 215: 403-410 (1990).
Altschul, S.F., et al., "Gapped BLAST and PSI-BLAST: a new generation of protein database search programs," Nucleic Acids Res., 25(17):3389-3402 (1997).

(Continued)

*Primary Examiner* — Richard G Hutson
(74) *Attorney, Agent, or Firm* — FisherBroyles, LLP; Adam K. Whiting

(57) ABSTRACT

The present disclosure provides engineered ketoreductase enzymes having improved properties as compared to a naturally occurring wild-type ketoreductase enzyme. Also provided are polynucleotides encoding the engineered ketoreductase enzymes, host cells capable of expressing the engineered ketoreductase enzymes, and methods of using the engineered ketoreductase enzymes to synthesize a variety of chiral compounds.

6 Claims, 1 Drawing Sheet
Specification includes a Sequence Listing.

(56) References Cited

U.S. PATENT DOCUMENTS

| | | | |
|---|---|---|---|
| 6,391,640 B1 | 5/2002 | Minshull et al. |
| 6,395,547 B1 | 5/2002 | Stemmer |
| 6,399,339 B1 | 6/2002 | Wolberg et al. |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,495,023 B1 | 12/2002 | Zeikus et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,645,746 B1 | 11/2003 | Kizaki et al. |
| 6,653,072 B1 | 11/2003 | Patten et al. |
| 6,716,631 B1 | 4/2004 | delCardayre et al. |
| 6,800,477 B2 | 10/2004 | Patel et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selifonov et al. |
| 7,430,477 B2 | 9/2008 | Selifonov et al. |
| 7,534,564 B2 | 5/2009 | Patten et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,499 B2 | 1/2011 | Selifonov et al. |
| 7,883,879 B2 | 2/2011 | Campopiano et al. |
| 7,904,249 B2 | 3/2011 | Selifonov et al. |
| 7,957,912 B2 | 6/2011 | Selifonov et al. |
| 7,977,078 B2 * | 7/2011 | Liang ............... C12P 17/00 435/189 |
| 8,748,143 B2 | 6/2014 | Liang et al. |
| 10,696,953 B2 | 6/2020 | Alvizo et al. |
| 2005/0095619 A1 | 5/2005 | Davis et al. |
| 2005/0153417 A1 | 7/2005 | Davis et al. |
| 2006/0195947 A1 | 8/2006 | Davis et al. |
| 2006/0286646 A1 | 12/2006 | Patel et al. |
| 2008/0220990 A1 | 9/2008 | Fox |
| 2009/0191605 A1 | 7/2009 | Liang et al. |
| 2009/0312196 A1 | 12/2009 | Colbeck et al. |
| 2011/0159567 A1 | 6/2011 | Campopiano et al. |

FOREIGN PATENT DOCUMENTS

| | | |
|---|---|---|
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 2000/42651 A1 | 7/2000 |
| WO | 2000/053731 A2 | 9/2000 |
| WO | 2001/040450 A1 | 6/2001 |
| WO | 2001/75767 A2 | 10/2001 |
| WO | 2005/018579 A2 | 3/2005 |
| WO | 2005/054491 A1 | 6/2005 |
| WO | 2008/042876 A2 | 4/2008 |
| WO | 2009/036404 A2 | 3/2009 |
| WO | 2009/152336 A1 | 12/2009 |
| WO | 2013/074650 A1 | 5/2013 |
| WO | 2014/188353 A2 | 11/2014 |
| WO | 2016/130412 A1 | 8/2016 |

OTHER PUBLICATIONS

Botstein, D., et al., "Strategies and applications of in vitro mutagenesis," Science, 229(4719):1193-1201, 1985.

Broussy, R.W., et al., "Enantioselective, Ketoreductase-Based Entry into Pharmaceutical Building Blocks: Ethanol as Tunable Nicotinamide Reductant," Org. Lett., 11(2):305-308 [2009].

Carter, P., "Site-directed mutagenesis," Biochem. J., 237:1-7 (1986).

Christians, F.C., et al., "Directed evolution of thymidine kinase for AZT phosphorylation using DNA family shuffling," Nat. Biotechnol., 17:259-264 (1999).

Crameri, A., et al., "DNA shuffling of a family of genes from diverse species accelerates directed evolution," Nature, 391:288-291 (1998).

Crameri, A., et al., "Improved green fluorescent protein by molecular evolution using DNA shuffling," Nat. Biotechnol., 14(3):315-319 (1996).

Crameri, A., et al., "Molecular evolution of an arsenate detoxification pathway by DNA shuffling," Nat. Biotechnol., 15(5):436-438 (1997).

Dale, S.J., et al., "Oligonucleotide-directed random mutagenesis using the phosphorothioate method," Methods Mol. Biol., 57:369-74 (1996).

De Boer, H.A., et al., "The tac promoter: A functional hybrid derived from the trp and lac promoters," Proc. Natl Acad. Sci. USA, 80: 21-25 (1983).

Ehrlich, S.D.,"DNA cloning in Bacillus subtilis," Proc. Natl. Acad. Sci. USA, 75(3):1433-1436 [1978].

Guo, Z., et al., "3'-End-Forming Signals of Yeast mRNA," Mol. Cell. Biol., 15(11):5983-5990 [1995].

Heilmann, H.J., et al., "Identification and isolation of glucose dehydrogenase genes of Bacillus megaterium M1286 and their expression in Escherichia coli," Eur. J. Biochem., 174:485-490 [1988].

Henikoff, S.,et al., "Amino acid substitution matrices from protein blocks," Proc. Natl. Acad. Sci., 89:10915-10919 (1992).

Hummel, W., et al., "Dehydrogenases for the synthesis of chiral compounds," Eur. J. Biochem., 184:1-13 [1989].

Vanova, N., et al., "Genome sequence of Bacillus cereus and comparative analysis with Bacillus anthracis," Nature, 123:87-91 [2003].

Kramer, B., et al., "Different base/base mismatches are corrected with different efficiencies by the methyl-directed DNA mismatch-repair system of E. coli," Cell, 38(3):879-887 [1984].

Lampel, K.A., et al., "Characterization of the developmentally regulated Bacillus subtilis glucose dehydrogenase gene," J. Bacteriol., 166:238-243 [1986].

Lathe, R., et al., "Plasmid and bacteriophage vectors fir excision of intact inserts," Gene, 57:193-201 [1987].

Ling, M., et al., "Approaches to DNA Mutagenesis: An Overview," Anal. Biochem., 254:157-78 (1997).

Matthes, H.W.D., et al., "Simultaneous rapid chemical synthesis of over one hundred oligonucleotides on a microscale," EMBO J., 3(4):801-05 (1984).

(56) References Cited

OTHER PUBLICATIONS

Minshull, J., et al., "Protein evolution by molecular breeding," Curr. Op. Chem. Biol., 3(3):284-290 (1999).
Mitamura, T., et al., "Structure of isozyme genes of glucose dehydrogenase from Bacillus megaterium IAM1030," J. Ferment. Bioeng., 70:363-369 [1990].
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Romanos, M.A., et al., "Foreign gene expression in yeast: a review," Yeast 8:423-488 [1992].
Santaniello, E., et al., "Chiral synthesis of a component of Amanita muscaria, (−)-4-hydroxypyrrolidin-2-one, and Assessment of its absolute configuration," J. Chem. Res., (S)132-133 [1984].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stellwagon, E., "Dye Affinity Chromatography," Current Protocols in Protein Science, Unit 9.2-9.2.16 [2001].
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Vasantha, N., et al., "Isolation of a developmental gene of Bacillus subtilis and its expression in *Escherichia coli*," Proc. Natl. Acad. Sci. USA, 80(3):785-789 [1983].
Villa-Komaroff, L., et al., "A bacterial clone synthesizing proinsulin," Proc. Natl Acad. Sci. USA, 75:3727-3731 (1978).
Wells, J.A., et al., "Cassette mutagenesis: an efficient method for generation of multiple mutations at defined sites," Gene, 34:315-323 (1985).
Yamane, K., et al., "The 25°-36° region of the Bacillus subtilis chromosome: determination of the sequence of a 146 kb segment and identification of 113 genes ," Microbiology, 142(11):3047-3056 [1996].
Zhang, J-H., et al., "Directed evolution of a fucosidase from a galactosidase by DNA shuffling and screening ," Proc. Nat. Acad. Sci., U.S.A., 94:4504-4509 (1997).
Zhou, B., et al., "Stereochemical control of yeast reductions. 1. Asymmetric synthesis of L-Carnitine," J. Am. Chem. Soc., 105:5925-5926 [1983].
4-Chloro-6,7dihydro-5H-cyclopenta[b]pyridine-7-ol, CRST Pharmatech [2016]; retrieved from http://www.crstpharma.com.
Genbank Accession No. 1NXQ_A dated Sep. 24, 2008.
Genbank Accession No. AAP94029.1 dated Apr. 1, 2004.
Genbank Accession No. AE017013 dated May 16, 2003.
Genbank Accession No. AF160799 dated Dec. 9, 1999.
Genbank Accession No. BAA24528.1 dated Jan. 28, 1998.
Genbank Accession No. D50453 dated Jul. 6, 2007.
Genbank Accession No. JC7338 dated Jun. 3, 2002.
Genbank Accession No. M12276 dated Apr. 26, 1993.
Genbank Accession No. X12370 dated Oct. 23, 2008.

\* cited by examiner

KETOREDUCTASE POLYPEPTIDES FOR THE SYNTHESIS OF CHIRAL COMPOUNDS The present application claims priority to copending U.S. patent application Ser. No. 16/874,574 filed May 14, 2020, which claims priority to U.S. patent application Ser. No. 15/543,535 filed Jul. 13, 2017, now U.S. Pat. No. 10,696,953, which is a national stage application filed under 35 USC § 371 and claims priority to international application to PCT International Application No. PCT/US2016/016692, filed Feb. 5, 2016, which claims priority to U.S. Prov. Pat. Appln. Ser. No. 62/114,380, filed Feb. 10, 2015, all of which are hereby incorporated by reference, in their entireties and for all purposes.

REFERENCE TO SEQUENCE LISTING, TABLE OR COMPUTER PROGRAM

The Sequence Listing concurrently submitted herewith under 37 C.F.R. § 1.821 in a computer readable form (CRF) via EFS-Web as file name CX2-148WO1_ST25.txt is herein incorporated by reference. The electronic copy of the Sequence Listing was created on Feb. 4, 2016, with a file size of 456 Kbytes.

FIELD OF THE INVENTION

The present invention provides engineered ketoreductase enzymes having improved properties as compared to a naturally occurring wild-type ketoreductase enzyme, as well as polynucleotides encoding the engineered ketoreductase enzymes, host cells capable of expressing the engineered ketoreductase enzymes, and methods of using the engineered ketoreductase enzymes to synthesize a variety of chiral compounds.

BACKGROUND

Enzymes belonging to the ketoreductase (KRED) or carbonyl reductase class (EC1.1.1.184) are useful for the synthesis of optically active alcohols from the corresponding prochiral ketone substrate and by stereoselective reduction of corresponding racemic aldehyde substrates. KREDs typically convert ketone and aldehyde substrates to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state), but not both.

In order to circumvent many chemical synthetic procedures for the production of key compounds, ketoreductases are being increasingly employed for the enzymatic conversion of different keto and aldehyde substrates to chiral alcohol products. These applications can employ whole cells expressing the ketoreductase for biocatalytic ketone and aldehyde reductions, or by use of purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase etc. can be used in conjunction with the ketoreductase. It is desirable to identify other ketoreductase enzymes that can be used to carryout conversion of various keto substrates to corresponding chiral alcohol products.

SUMMARY OF THE INVENTION

The present invention provides engineered ketoreductase enzymes having improved properties as compared to a naturally occurring wild-type ketoreductase enzyme, as well as polynucleotides encoding the engineered ketoreductase enzymes, host cells capable of expressing the engineered ketoreductase enzymes, and methods of using the engineered ketoreductase enzymes to synthesize a variety of chiral compounds.

The present disclosure provides engineered ketoreductase ("KRED") enzymes that are capable of stereoselectively reducing a defined keto substrate to its corresponding alcohol product and having an improved property when compared with the naturally-occurring, wild-type KRED enzyme obtained from *L. kefir* (SEQ ID NO:2) or when compared with other engineered ketoreductase enzymes.

Moreover, the engineered enzymes described herein can have one or more improved properties in addition to the altered stereoselectivity. For example, the engineered ketoreductase polypeptide can have increased enzymatic activity as compared to the wild-type ketoreductase enzyme for reducing the substrate to the product and/or further increases stereoselectivity for the (S) enantiomer. Improvements in enzyme properties can also include, among others, increases in thermostability, solvent stability, and/or reduced product inhibition.

The present invention provides engineered polypeptides comprising amino acid sequences with at least 80% sequence identity to SEQ ID NO:2 and at least one substitution at a position selected from X68, X94, X102, X110, X114, X135, X144, X145, X147, X149, X150, X153, X158, X173, X175, X190, X196, X197, X198, X199, X201, X202, X203, X205, X206, X207, X209, X210, X211, X212, X213, X217, X233, X249, X250, and X252, as compared to SEQ ID NO:2, and wherein the polypeptide has greater 2a:2c selectivity as compared to SEQ ID NO:2. In some embodiments, the amino acid sequences of the engineered polypeptides comprise at least one of the following: the residue corresponding to X68 is a non-polar, or aliphatic residue; the residue corresponding to X94 is a polar, or non-polar residue; the residue corresponding to X102 is an acidic residue; the residue corresponding to X110 is an acidic, or aromatic residue; the residue corresponding to X114 is a non-polar residue; the residue corresponding to X135 is a basic residue; the residue corresponding to X144 is a non-polar, or aromatic residue; the residue corresponding to X145 is an aromatic residue; the residue corresponding to X147 is a non-polar, or aliphatic residue; the residue corresponding to X149 is a polar residue; the residue corresponding to X150 is an aromatic, or acidic residue; the residue corresponding to X153 is a polar, or aromatic residue; the residue corresponding to X158 is a non-polar, or aliphatic residue; the residue corresponding to X173 is a non-polar, or aliphatic residue; the residue corresponding to X175 is a polar residue; the residue corresponding to X190 is an aromatic, aliphatic, non-polar, or polar residue; the residue corresponding to X196 is an aromatic, polar, basic, non-polar, or aliphatic residue; the residue corresponding to X197 is an aromatic residue; the residue corresponding to X198 is a non-polar, polar residue; the residue corresponding to X199 is an acidic residue; the residue corresponding to X201 is a polar residue; the residue corresponding to X202 is an aromatic, or basic residue; the residue corresponding to X203 is an aromatic, non-polar, or aliphatic residue; the residue corresponding to X205 is a polar residue; the residue corresponding to X206 is an aromatic residue; the residue corresponding to X207 is an aromatic, acidic, non-polar, or aliphatic residue; the residue corresponding to X209 is an aromatic, acidic, non-polar, polar, or aliphatic residue; the residue corresponding to X210 is a non-polar, or aliphatic residue; the residue corresponding to X211 is an aromatic, acidic, aliphatic, polar, or non-polar residue; the residue corresponding to X212 is an aromatic, basic, non-polar, aliphatic, or acidic residue; the residue corresponding to X213 is an aromatic, basic, acidic, polar, non-polar, or aliphatic residue; the residue corresponding to X217 is a polar, or aromatic residue; the residue corresponding to X233 is a polar residue; the residue corresponding to X249 is a basic, or non-polar residue; the residue corresponding to X250 is a non-polar residue; and the residue corresponding to X252 is an aromatic residue, as compared to SEQ ID NO:2. In some additional embodiments, the amino acid sequences of the engineered polypeptides comprise at least one substitution selected from X68V, X94G/M/Q, X102D, X110E/W, X114G, X135K, X144G/W, X145W, X147L, X149S, X150D/F/P/W, X153H/P/T/V/C, X158V, X173L, X175T, X190A/L/Q/T/W, X196H/I/K/N/Q, X196I, X196K/N/Q, X197Y, X198G/S, X199E, X201N, X202F/H/R/Y, X203G/L/W, X205T, X206H/W/Y, X207D/G/V/Y, X209E/F/G/I/M/T/V/W, X210L/P, X211E/H/I/P/S, X212A/E/G/H/N/P/R/V, X213D/E/G/H/K/M/N/R, X217H/N, X233Q/T, X249G/K/R, X250G, and X252W, as compared to SEQ ID NO:2. In some further embodiments, the amino acid sequences of the engineered polypeptides comprise a substitution at position X190, as compared to SEQ ID NO:2. In still some additional embodiments, the amino acid sequences of the engineered polypeptides comprise a substitution at position X190, wherein the substitution is selected from P, A, T, and Q, as compared to SEQ ID NO:2. In some embodiments, the amino acid sequences of the engineered polypeptides comprise a substitution at position X249, as compared to SEQ ID NO:2. In some additional embodiments, the amino acid sequences of the engineered polypeptides comprise a substitution at position X249, wherein the substitution is selected from R, K, and G, as compared to SEQ ID NO:2. In some further embodiments, the amino acid sequences of the engineered polypeptides comprise substitutions at positions X190 and X249, as compared to SEQ ID NO:2. In still some further embodiments, the amino acid sequences of the engineered polypeptides comprise substitutions at positions X190 and X249, wherein the substitution at position X190 is selected from P, A, T, and Q, and the substitution at position 249 is selected from R, K, and G, as compared to SEQ ID NO:2.

The present invention also provides engineered polypeptides comprising amino acid sequences with at least 80% sequence identity to SEQ ID NO:4, and at least one substitution at a position selected from X94, X144, X145, X150, X190, and X249, as compared to SEQ ID NO: \4, and wherein said polypeptide has greater 2a:2c selectivity as compared to SEQ ID NO:4. In some embodiments, the amino acid sequences of the engineered polypeptides comprise at least one of the following: the residue corresponding to X145 is an aromatic residue; the residue corresponding to X249 is a basic residue; the residue corresponding to X94 is a non-polar residue; the residue corresponding to X144 is a non-polar residue; the residue corresponding to X150 is a residue; and the residue corresponding to X190 is an aromatic residue, as compared to SEQ ID NO:4. In some additional embodiments, the amino acid sequences of the engineered polypeptides comprise at least one substitution selected from X145W, X249K/R, X94G, X144G, X150P, X190W, as compared to SEQ ID NO:4.

The present invention also provides engineered polypeptides comprising amino acid sequences with at least 80% sequence identity to SEQ ID NO:10 and at least one substitution at a position selected from X145, X150, X153, X190, X198, X206, and X211, as compared to SEQ ID NO:10, and wherein said polypeptide has greater 2a:2c selectivity as compared to SEQ ID NO:10. In some embodiments, the amino acid sequences of the engineered polypeptides comprise at least one of the following: the residue corresponding to X145 is an aromatic residue; the residue corresponding to X150 is an aromatic residue; the residue corresponding to X153 is a residue; the residue corresponding to X190 is an aliphatic or non-polar residue; the residue corresponding to X198 is a non-polar residue; the residue corresponding to X206 is an aromatic residue; and the residue corresponding to X211 is an aromatic, acidic, aliphatic, polar, or non-polar residue, as compared to SEQ ID NO:10. In some further embodiments, the amino acid sequences of the engineered polypeptides comprise at least one substitution selected from X145W, X150W/F, X153C, X190A, X198G, X206Y, and X211I/H/S/E, as compared to SEQ ID NO:10.

The present invention also provides engineered polypeptides comprising amino acid sequences with at least 80% sequence identity to SEQ ID NO:26 and at least one substitution at a position selected from X94, X147, X153, X175, X190, X196, X199, X201, X202, X203, X206, X207, X209, X210, X211, X212, X213, X217, as compared to SEQ ID NO:26, and wherein said polypeptide has greater 2a:2c selectivity as compared to SEQ ID NO:26. In some embodiments, the amino acid sequences of the engineered polypeptides comprise at least one of the following: the residue corresponding to X147 is a non-polar, or aliphatic residue; the residue corresponding to X153 is a polar, or aromatic residue; the residue corresponding to X175 is a polar residue; the residue corresponding to X190 is a polar, aliphatic, or non-polar residue; the residue corresponding to X196 is a polar, basic, non-polar, or aliphatic residue; the residue corresponding to X199 is an acidic residue; the residue corresponding to X201 is a polar residue; the residue corresponding to X202 is an aromatic, or basic residue; the residue corresponding to X203 is an aromatic, non-polar, or aliphatic residue; the residue corresponding to X206 is an aromatic residue; the residue corresponding to X207 is an aromatic, acidic, or non-polar residue; the residue corresponding to X209 is an aromatic, acidic, non-polar, polar, or aliphatic residue; the residue corresponding to X210 is a non-polar, or aliphatic residue; the residue corresponding to X211 is a non-polar residue; the residue corresponding to X212 is an aromatic, basic, non-polar, or acidic residue; the residue corresponding to X213 is an aromatic, basic, acidic, polar, non-polar, or aliphatic residue; the residue corresponding to X217 is a polar residue; and the residue corresponding to X94 is a polar, or non-polar residue, as compared to SEQ ID NO:26. In some further embodiments, the amino acid sequences of the engineered polypeptides comprise at least one substitution selected from X94Q/M, X147L, X153T/H, X175T, X190Q/L, X196N/K/I, X199E, X201N, X202Y/R/H/F, X203W/L, X206W/H, X207Y/G/D, X209Y/W/V/T/M/I/G/F/E, X210P/L, X211P, X212R/H/G/E, X213T/R/N/M/K/H/G/E/D, and X217N, as compared to SEQ ID NO:26.

The present invention also provides engineered polypeptides comprising amino acid sequences with at least 80% sequence identity to SEQ ID NO:42 and at least one substitution at a position selected from X68, X94, X102, X110, X114, X135, X149, X150, X153, X158, X173, X190, X196, X197, X198, X203, X205, X207, X209, X212, X213, X217, X233, X249, X250, X252, as compared to SEQ ID NO:42, and wherein said polypeptide has greater 2a:2c selectivity as compared to SEQ ID NO:42. In some embodiments, the amino acid sequences of the engineered polypeptides comprise at least one of the following: the residue corresponding to X102 is an acidic residue; the residue corresponding to X110 is an acidic, or aromatic residue; the residue corresponding to X114 is a non-polar residue; the residue corresponding to X135 is a basic residue; the residue corresponding to X149 is a polar residue; the residue corresponding to X150 is an acidic residue; the residue corresponding to X153 is a residue; the residue corresponding to X158 is a non-polar, or aliphatic residue; the residue corresponding to X173 is a non-polar, or aliphatic residue; the residue corresponding to X190 is a non-polar, polar, or aliphatic residue; the residue corresponding to X196 is an aromatic, or polar residue; the residue corresponding to X197 is an aromatic residue; the residue corresponding to X198 is a polar residue; the residue corresponding to X203 is a non-polar, aromatic, aliphatic residue; the residue corresponding to X205 is a polar residue; the residue corresponding to X207 is a non-polar, or aliphatic residue; the residue corresponding to X209 is a non-polar residue; the residue corresponding to X212 is a non-polar, aliphatic, acidic, or aromatic residue; the residue corresponding to X213 is an acidic, basic, non-polar, aliphatic, or polar residue; the residue corresponding to X217 is an aromatic residue; the residue corresponding to X233 is a polar residue; the residue corresponding to X249 is a non-polar residue; the residue corresponding to X250 is a non-polar residue; the residue corresponding to X252 is an aromatic residue; the residue corresponding to X68 is a non-polar, or aliphatic residue; and the residue corresponding to X94 is a polar residue. In some additional embodiments, the amino acid sequences of the engineered polypeptides comprise at least substitution selected from X68V, X94Q, X102D, X110E/W, X114G, X135K, X149S, X150D, X153P, X158V, X173L, X190L/T, X196H/N/Q, X197Y, X198S, X203G/L/W, X205T, X207V, X209G, X212A/E/G/H/N/P, X213E/G/K/M/N/T/R/V, X217H, X233Q/T, X249G, X250G, and X252W, as compared to SEQ ID NO:42.

The present invention also provides engineered polypeptides, wherein the stereoselective activity of the polypeptides is increased at least 2-fold as compared to the corresponding activity of the reference polypeptide of SEQ ID NOS:4, 10, 26, and/or 42.

The present invention also provides engineered polypeptides in which the amino acid sequence comprises a sequence selected from the group consisting of the even-numbered sequence identifiers of SEQ ID NOS:6-238.

The present invention also provides engineered polypeptides having ketoreductase activity, wherein the polypeptide comprises SEQ ID NO:240. In some embodiments, the residue corresponding to X173 is leucine. In some alternative embodiments, the residue corresponding to X249 is glycine. In some further embodiments, the residue corresponding to X173 is leucine and the residue corresponding to X249 is glycine.

The present invention also provides engineered polypeptides having ketoreductase activity, wherein the polypeptide comprises SEQ ID NO:239. In some embodiments, the residue corresponding to X173 is leucine. In some alternative embodiments, the residue corresponding to X249 is glycine. In some further embodiments, the residue corresponding to X173 is leucine and the residue corresponding to X249 is glycine.

The present invention also provides polynucleotides encoding the engineered polypeptides provided herein. In some embodiments, the polynucleotide comprises a nucleic acid sequence selected from the group consisting of the odd-numbered sequence identifiers of SEQ ID NOS:5-237.

The present invention also provides expression vectors comprising the polynucleotide(s) provided herein.

The present invention also provides host cells comprising the polynucleotide(s) provided herein or at least one expression vector provided herein.

The present invention also provides methods of preparing engineered polypeptides having ketoreductase activity, comprising culturing the host cell provided herein, under conditions suitable for expression of the polypeptide, optionally further comprising isolating the engineered polypeptide.

DESCRIPTION OF THE INVENTION

Figure 1:
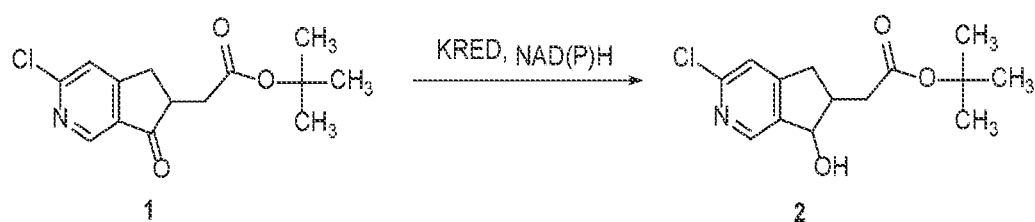
FIG. 1 provides the reaction scheme.

The present invention provides engineered ketoreductase enzymes having improved properties as compared to a naturally occurring wild-type ketoreductase enzyme, as well as polynucleotides encoding the engineered ketoreductase enzymes, host cells capable of expressing the engineered ketoreductase enzymes, and methods of using the engineered ketoreductase enzymes to synthesize a variety of chiral compounds.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings. All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation and amino acid sequences are written left to right in amino to carboxy orientation, respectively.

The headings provided herein are not limitations of the various aspects or embodiments of the invention that can be had by reference to the specification as a whole. Accordingly, the terms defined below are more fully defined by reference to the specification as a whole.

"Ketoreductase" and "KRED" are used interchangeably herein to refer to a polypeptide having an enzymatic capability of reducing a carbonyl group to its corresponding alcohol. More specifically, the ketoreductase polypeptides of the invention are capable of stereoselectively reducing the compound of formula (I) to the corresponding product of formula (II), as shown in Scheme 1 (See, FIG. 1).

As used herein, the terms "protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

As used herein, "polynucleotide" and "nucleic acid' refer to two or more nucleosides that are covalently linked together. The polynucleotide may be wholly comprised ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine, and cytosine), it may include one or more modified and/or synthetic nucleobases (e.g., inosine, xanthine, hypoxanthine, etc.). Preferably, such modified or synthetic nucleobases will be encoding nucleobases.

As used herein, "coding sequence" refers to that portion of a nucleic acid (e.g., a gene) that encodes an amino acid sequence of a protein.

As used herein, "naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

As used herein, "non-naturally occurring" or "engineered" or "recombinant" when used in the present disclosure with reference to (e.g., a cell, nucleic acid, or polypeptide), refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

As used herein, "percentage of sequence identity," "percent identity," and "percent identical" refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (See e.g., Altschul et al., J. Mol. Biol. 215: 403-410 [1990]; and Altschul et al., Nucleic Acids Res. 3389-3402 [1977]). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See e.g., Henikoff and Henikoff, Proc Natl Acad Sci USA 89:10915 [1989]).

Numerous other algorithms are available and known in the art that function similarly to BLAST in providing percent identity for two sequences. Optimal alignment of sequences for comparison can be conducted using any suitable method known in the art (e.g., by the local homology algorithm of Smith and Waterman, Adv. Appl. Math. 2:482 [1981]; by the homology alignment algorithm of Needleman and Wunsch, J. Mol. Biol. 48:443 [1970]; by the search for similarity method of Pearson and Lipman, Proc. Natl. Acad. Sci. USA 85:2444 [1988]; and/or by computerized implementations of these algorithms [GAP, BESTFIT, FASTA, and TFASTA in the GCG Wisconsin Software Package]), or by visual inspection, using methods commonly known in the art. Additionally, determination of sequence alignment and percent sequence identity can employ the BESTFIT or GAP programs in the GCG Wisconsin Software package (Accelrys, Madison WI), using the default parameters provided.

As used herein, "reference sequence" refers to a defined sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, in some embodiments, a "reference sequence" can be a previously engineered or altered amino acid sequence.

As used herein, "comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. As used herein, a reference to a residue position, such as "Xn" as further described below, is to be construed as referring to "a residue corresponding to", unless specifically denoted otherwise. Thus, for example, "X94" refers to any amino acid at position 94 in a polypeptide sequence (e.g., SEQ ID NOS:2, 4, 10, 26, or 42).

As used herein, "stereoselectivity" refers to the preferential formation in a chemical or enzymatic reaction of one stereoisomer over another stereoisomer or another set of stereoisomers. Stereoselectivity can be partial, where the formation of a stereoisomer is favored over another, or it may be complete where only one stereoisomer is formed. When the stereoisomers are enantiomers, the stereoselectivity is referred to as enantioselectivity, the fraction (typically reported as a percentage) of one enantiomer in the sum of both enantiomers. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess. It is also to be understood that stereoselectivity is not limited to single stereoisomers and can be described for sets of stereoisomers.

As used herein, "highly stereoselective" refers to a chemical or enzymatic reaction that is capable of converting a substrate to its corresponding chiral alcohol product, with at least about 75% stereomeric excess.

As used herein, "increased enzymatic activity" and "increased activity" refer to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of ketoreductase) as compared to a reference enzyme. Exemplary methods to determine enzyme activity are provided in the Examples. Any property relating to enzyme activity may be affected, including the classical enzyme properties of Km, Vmax or kcat, changes of which can lead to increased enzymatic activity. The ketoreductase activity can be measured by any one of standard assays used for measuring ketoreductases, such as change in substrate or product concentration, or change in concentration of the cofactor (in absence of a cofactor regenerating system). Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

As used herein, "conversion" refers to the enzymatic transformation of a substrate to the corresponding product.

As used herein "percent conversion" refers to the percent of the substrate that is converted to the product within a period of time under specified conditions. Thus, for example, the "enzymatic activity" or "activity" of a ketoreductase polypeptide can be expressed as "percent conversion" of the substrate to the product.

As used herein, "thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (e.g., more than 60% to 80% for example) after exposure to elevated temperatures.

As used herein, "solvent stable" refers to the ability of a polypeptide to maintain similar activity (e.g., more than e.g., 60% to 80%) after exposure to varying concentrations (e.g., 5-99%) of solvent (e.g., isopropyl alcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

As used herein, "amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X40 as compared to SEQ ID NO:2" refers to a difference of the amino acid residue at the polypeptide position corresponding to position 40 of SEQ ID NO:2. Thus, if the reference polypeptide of SEQ ID NO:2 has a histidine at position 40, then a "residue difference at position X40 as compared to SEQ ID NO:2" refers to an amino acid substitution of any residue other than histidine at the position of the polypeptide corresponding to position 40 of SEQ ID NO:2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances, the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X192A/G). The present disclosure includes engineered polypeptide sequences comprising one or more amino acid differences that include either/or both conservative and non-conservative amino acid substitutions. The amino acid sequences of the specific recombinant carbonic anhydrase polypeptides included in the Sequence Listing of the present disclosure include an initiating methionine (M) residue (i.e., M represents residue position 1). The skilled artisan, however, understands that this initiating methionine residue can be removed by biological processing machinery, such as in a host cell or in vitro translation system, to generate a mature protein lacking the initiating methionine residue, but otherwise retaining the enzyme's properties. Consequently, the term "amino acid residue difference relative to SEQ ID NO:2 at position Xn" as used herein may refer to position "Xn" or to the corresponding position (e.g., position (X−1)n) in a reference sequence that has been processed so as to lack the starting methionine.

As used herein, the phrase "conservative amino acid substitutions" refers to the interchangeability of residues having similar side chains, and thus typically involves substitution of the amino acid in the polypeptide with amino acids within the same or similar defined class of amino acids. By way of example and not limitation, in some embodiments, an amino acid with an aliphatic side chain is substituted with another aliphatic amino acid (e.g., alanine, valine, leucine, and isoleucine); an amino acid with a hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively. Exemplary conservative substitutions are provided in Table 1.

TABLE 1

Exemplary Conservative Amino Acid Substitutions

| Residue | Possible Conservative Substitutions |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | Non-polar |

As used herein, the phrase "non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

As used herein, "deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

As used herein, "insertion" refers to modification of the polypeptide by addition of one or more amino acids to the reference polypeptide. In some embodiments, the improved engineered ketoreductase enzymes comprise insertions of one or more amino acids to the naturally occurring ketoreductase polypeptide as well as insertions of one or more amino acids to engineered ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The term "amino acid substitution set" or "substitution set" refers to a group of amino acid substitutions in a polypeptide sequence, as compared to a reference sequence. A substitution set can have 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant KREDs listed in the Tables provided in the Examples.

As used herein, "fragment" refers to a polypeptide that has an amino-terminal and/or carboxy-terminal deletion, but where the remaining amino acid sequence is identical to the corresponding positions in the sequence. Fragments can typically have about 80%, about 90%, about 95%, about 98%, or about 99% of the full-length ketoreductase polypeptide, for example the polypeptide of SEQ ID NO:4. In some embodiments, the fragment is "biologically active" (i.e., it exhibits the same enzymatic activity as the full-length sequence).

As used herein, "isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the engineered ketoreductase polypeptides of the present disclosure can be an isolated polypeptide.

As used herein, "substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure engineered ketoreductase polypeptide composition will comprise about 60% or more, about 70% or more, about 80% or more, about 90% or more, about 91% or more, about 92% or more, about 93% or more, about 94% or more, about 95% or more, about 96% or more, about 97% or more, about 98% or more, or about 99% of all macromolecular species by mole or % weight present in the composition. Solvent species, small molecules (<500 Daltons), and elemental ion species are not considered macromolecular species. In some embodiments, the isolated improved ketoreductase polypeptide is a substantially pure polypeptide composition.

As used herein, when used with reference to a nucleic acid or polypeptide, the term "heterologous" refers to a sequence that is not normally expressed and secreted by an organism (e.g., a wild-type organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector). In some embodiments, "heterologous polynucleotide" refers to any polynucleotide that is introduced into a host cell by laboratory techniques, and includes polynucleotides that are removed from a host cell, subjected to laboratory manipulation, and then reintroduced into a host cell.

As used herein, "codon optimized" refers to changes in the codons of the polynucleotide encoding a protein to those preferentially used in a particular organism such that the encoded protein is efficiently expressed in the organism of interest. In some embodiments, the polynucleotides encoding the ketoreductase enzymes may be codon optimized for optimal production from the host organism selected for expression.

As used herein, "control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

As used herein, "operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

As used herein, the phrases "cofactor regeneration system" and "cofactor recycling system" refer to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

As used herein, "secondary alcohol dehydrogenase" is used herein to refer to an NAD+ or NADP+-dependent enzyme that catalyzes the conversion of a secondary alcohol (e.g., isopropyl alcohol) and NAD+ or NADP+ to a ketone and NADH or NADPH, respectively.

As used herein, "suitable reaction conditions" refer to those conditions in the biocatalytic reaction solution (e.g., ranges of enzyme loading, substrate loading, cofactor loading, temperature, pH, buffers, co-solvents, etc.) under which a ketoreductase polypeptide of the present disclosure is capable of converting a substrate compound to a product compound (e.g., conversion of compound (1) to compound (2a)). Exemplary "suitable reaction conditions" are provided in the present disclosure and illustrated by the Examples.

As used herein, "loading," such as in "compound loading," "enzyme loading," or "cofactor loading" refers to the concentration or amount of a component in a reaction mixture at the start of the reaction.

As used herein, "substrate" in the context of a biocatalyst mediated process refers to the compound or molecule acted on by the biocatalyst. For example, an exemplary substrate for the ketoreductase biocatalyst in the process disclosed herein is compound (1).

As used herein "product" in the context of a biocatalyst mediated process refers to the compound or molecule resulting from the action of the biocatalyst. For example, an exemplary product for the ketoreductase biocatalyst in the process disclosed herein is compound (2a).

As used herein, "equilibration" as used herein refers to the process resulting in a steady state concentration of chemical species in a chemical or enzymatic reaction (e.g., interconversion of two species A and B), including interconversion of stereoisomers, as determined by the forward rate constant and the reverse rate constant of the chemical or enzymatic reaction.

As used herein, "alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis, e.g., $(C_1-C_4)$alkyl refers to an alkyl of 1 to 4 carbon atoms.

As used herein, "alkenyl" refers to groups of from 2 to 12 carbon atoms inclusively, either straight or branched containing at least one double bond but optionally containing more than one double bond.

As used herein, "alkynyl" refers to groups of from 2 to 12 carbon atoms inclusively, either straight or branched containing at least one triple bond but optionally containing more than one triple bond, and additionally optionally containing one or more double bonded moieties.

As used herein, "heteroalkyl, "heteroalkenyl," and heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —$NR^\alpha$—, —PH—, —S(O)—, —S(O)2-, —S(O) $NR^\alpha$—, —$S(O)_2$ $NR^\alpha$—, and the like, including combinations thereof, where each $R^\alpha$ is independently selected from hydrogen, alkyl, heteroalkyl, cycloalkyl, heterocycloalkyl, aryl, and heteroaryl.

As used herein, "alkoxy" refers to the group —$OR^\beta$ wherein $R^\beta$ is an alkyl group is as defined above including optionally substituted alkyl groups as also defined herein.

As used herein, "aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

As used herein, "amino" refers to the group —$NH_2$. Substituted amino refers to the group —$NHR^\delta$, $NR^\delta R^\delta$, and $NR^\delta R^\delta R^\delta$, where each $R^\delta$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylsulfonylamino, furanyl-oxy-sulfamino, and the like.

As used herein, "oxo" refers to =O.

As used herein, "oxy" refers to a divalent group —O—, which may have various substituents to form different oxy groups, including ethers and esters.

As used herein, "carboxy" refers to —COOH.

As used herein, "carbonyl" refers to —C(O)—, which may have a variety of substituents to form different carbonyl groups including acids, acid halides, aldehydes, amides, esters, and ketones.

As used herein, "alkyloxycarbonyl" refers to —$C(O)OR^\varepsilon$, where $R^\varepsilon$ is an alkyl group as defined herein, which can be optionally substituted.

As used herein, "aminocarbonyl" refers to —$C(O)NH_2$. Substituted aminocarbonyl refers to —$C(O)NR^\delta R^\delta$, where the amino group $NR^\delta R^\delta$ is as defined herein.

As used herein, "halogen" and "halo" refer to fluoro, chloro, bromo and iodo.

As used herein, "hydroxy" refers to —OH.

As used herein, "cyano" refers to —CN.

As used herein, "heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

As used herein, "heteroarylalkyl" refers to an alkyl substituted with a heteroaryl (i.e., heteroaryl-alkyl- groups), preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

As used herein, "heteroarylalkenyl" refers to an alkenyl substituted with a heteroaryl (i.e., heteroaryl-alkenyl-groups), preferably having from 2 to 6 carbon atoms inclusively in the alkenyl moiety and from 5 to 12 ring atoms inclusively in the heteroaryl moiety.

As used herein, "heteroarylalkynyl" refers to an alkynyl substituted with a heteroaryl (i.e., heteroaryl-alkynyl-groups), preferably having from 2 to 6 carbon atoms inclusively in the alkynyl moiety and from 5 to 12 ring atoms inclusively in the heteroaryl moiety.

As used herein, "heterocycle," "heterocyclic," and interchangeably "heterocycloalkyl," refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

As used herein, "membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

As used herein, "optional" and "optionally" means that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included.

As used herein, "optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

As used herein, "protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups are well-known in the art. Functional groups that can have a protecting group include, but are not limited to, hydroxy, amino, and carboxy groups. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers. Other protecting groups can be found in the references noted herein.

Engineered Ketoreductase Polypeptides

Ketoreductase (KRED) or carbonyl reductase biocatalysts (EC 1.1.1.184) are useful for the synthesis of alcohols from aldehydes and ketones, and optically active secondary alcohols from the corresponding prostereoisomeric ketone substrates. KREDs may also catalyze the reverse reaction, (i.e., oxidation of an alcohol substrate to the corresponding aldehydes/ketone product). The reduction of aldehydes and ketones and the oxidation of alcohols by KREDs uses a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP+) for the oxidation reaction. NADH and NADPH serve as electron donors, while NAD+ and NADP+ serve as electron acceptors.

KREDs can be found in a wide range of bacteria and yeasts, as known in the art (See e.g., Hummel and Kula Eur. J. Biochem., 184:1-13 [1989]). Numerous KRED genes and enzyme sequences have been reported, including those of *Candida magnoliae* (Genbank Acc. No. JC7338; GI:11360538); *Candida parapsilosis* (Genbank Acc. No. BAA24528.1; GI:2815409), *Sporobolomyces salmonicolor* (Genbank Acc. No. AF160799; GI:6539734), *Lactobacillus kefir* (Genbank Acc. No. AAP94029.1; GI: 33112056), *Lactobacillus brevis* (Genbank Acc. No. 1NXQ_A; GI: 30749782), and *Thermoanaerobium brockii* (Genbank Acc. No. P14941; GI: 1771790).

The stereoselectivity of ketoreductases have been applied to the preparation of important pharmaceutical building blocks (See e.g., Broussy et al., Org. Lett., 11:305-308 [2009]). Specific applications of naturally occurring or engineered KREDs in biocatalytic processes to generate useful chemical compounds have been demonstrated for reduction of 4-chloroacetoacetate esters (See e.g., Zhou, J. Am. Chem. Soc., 105:5925-5926 [1983]; Santaniello, J. Chem. Res., (S)132-133 [1984]; U.S. Pat. Nos. 5,559,030; 5,700,670; and 5,891,685), reduction of dioxocarboxylic acids (See e.g., U.S. Pat. No. 6,399,339), reduction of tert-butyl (S)-chloro-5-hydroxy-3-oxohexanoate (See e.g., U.S. Pat. No. 6,645,746; and WO 01/40450), reduction pyrrolotriazine-based compounds (See e.g., U.S. Appln. Publ. No. 2006/

0286646); reduction of substituted acetophenones (See e.g., U.S. Pat. Nos. 6,800,477 and 8,748,143); and reduction of ketothiolanes (WO 2005/054491).

The present invention provides engineered ketoreductases capable of using the substrate compound (1), tert-butyl 2-(3-chloro-7-oxo-6,7-dihydro-5H-cyclopenta[c]pyridin-6-yl)acetate, as a substrate for the synthesis of product (2), tert-butyl 2-06S,7S)-3-chloro-7-hydroxy-6,7-dihydro-5H-cyclopenta[c]pyridin-6-yl)acetate, or corresponding structural analogs, as shown in the following reaction and FIG. 1.

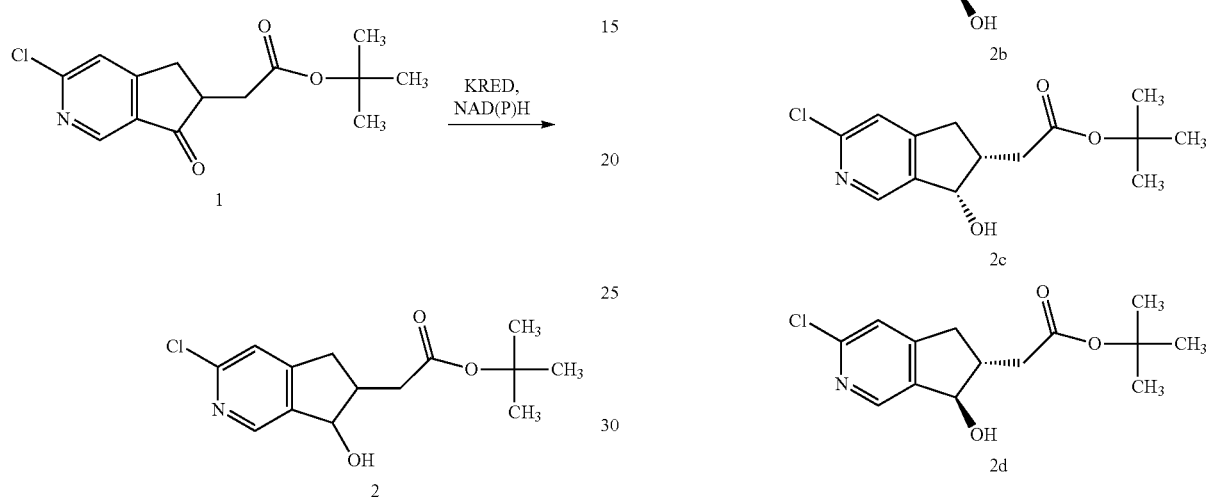

The present invention further provides improved ketoreductase enzymes and methods for using the engineered ketoreductase enzymes to synthesize chiral compounds.

Figure 2:
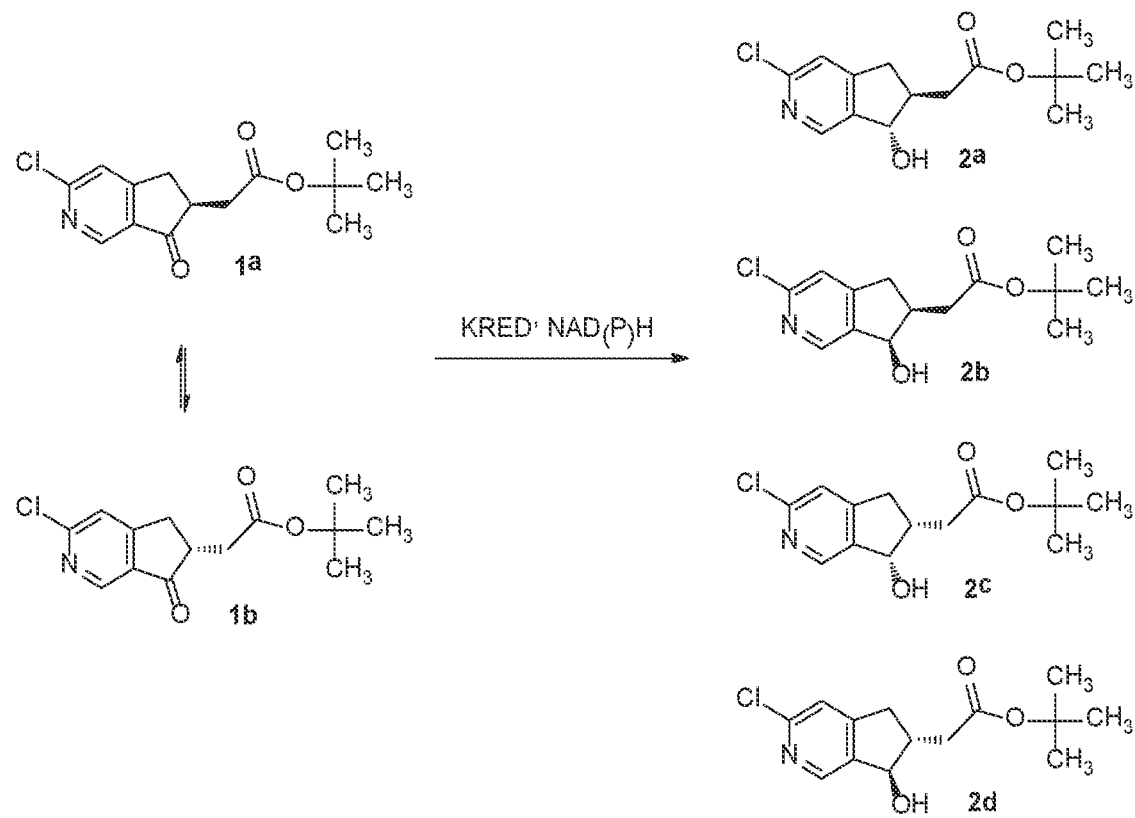
FIG. 2 provides the structures of substrate and product isomers.

Compound (1) has one chiral center and can exist in two different diastereomeric forms (1a and 1b). The epimerization process happens spontaneously at room temperature and at neutral to basic conditions. Consequently, the reaction by ketoreductase can result in at least four different stereomeric products (2a-2d), as shown in FIG. 2 and below.

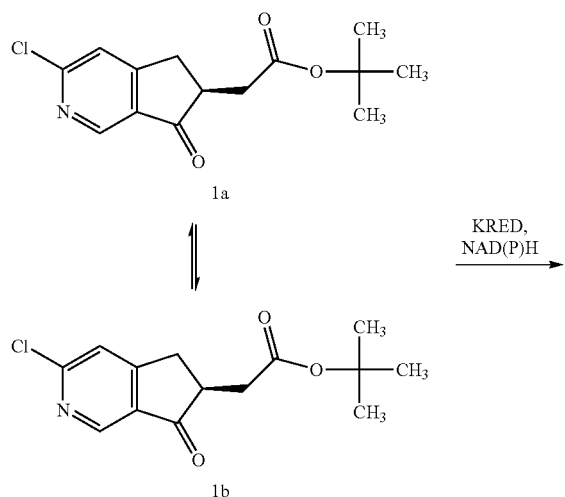

However, (2a) is the only desired product among the four stereoisomers. The evolution program used in the development of the present invention was designed to improve the selectivity of the ketoreductase for the use of substrate (1) to product (2a) with minimal amount of other side products (2b-2d). In addition, the enzyme variants were assessed with regard to their activity and stability.

The ketoreductase polypeptide of SEQ ID NO:4 was selected as the initial backbone for development of the improved enzymes provided by the present invention. This enzyme was chosen as the starting backbone as only two products (2a and 2c) were produced when it was used in the reaction; no formation of the other two products (2b and 2d) was observed, unlike the reaction products produced using the a variant enzyme (SEQ ID NO:4). As a result, selectivity values obtained in high throughput screening are calculated herein either by diastereomeric excess (d.e.), according to equation (1), or by diastereomeric ratio (d.r.), which is calculated according to equation (2), both of which are provided below. Due to the variability of d.e. and d.r. measurements over time selectivity improvements are reported as the fold improvement of d.r. over the variant enzyme (SEQ ID NO: 4).

$$[(2a\ amount)-(2c\ amount)]/[(2a\ amount)+(2c\ amount)] \quad (1)$$

$$(2a\ amount)/(2c\ amount) \quad (2)$$

Indeed, the non-naturally occurring polypeptides of the present invention are ketoreductases engineered to have improved properties as compared to the naturally occurring ketoreductase of SEQ ID NO:2 and/or the engineered ketoreductase of SEQ ID NO:4.

In some embodiments, the engineered ketoreductase polypeptides are capable of converting the substrate compound to product with an activity that is increased at least about 1.2 fold, 1.5 fold, 2 fold, 3 fold, 4 fold, 5 fold, 10 fold, 20 fold, 30 fold, 40 fold, 50 fold, or 100 fold relative to the activity of the reference polypeptide of SEQ ID NO:4 under suitable reaction conditions. In some embodiments, the engineered ketoreductase polypeptides are capable of converting the substrate compound to product with a percent conversion of at least about 40%, at least about 50%, at least about 60%, at least about 70%, at least about 80%, or at least about 90%, at least about 95%, at least about 98%, at least about 99%, in a reaction time of about 48 h, about 36 h, about 24 h, or even shorter length of time, under suitable reaction conditions.

In some embodiments, the engineered ketoreductases are capable of converting substrate compound (1) to product compound (2a) in diastereomeric excess over compound (2c). In some embodiments, the engineered ketoreductases are capable of converting compound (1) to compound (2a) in diastereomeric excess of at least 10%, 20%, 30%, 40%, 50%, 60%, 70%, 80%, 90%, or greater over compound (2c) under suitable reaction conditions.

As will be appreciated by those of skill in the art, some of the above-defined categories, unless otherwise specified, are not mutually exclusive. Thus, amino acids having side chains exhibiting two or more physico-chemical properties can be included in multiple categories. The appropriate classification of any amino acid or residue will be apparent to those of skill in the art, especially in light of the detailed disclosure provided herein.

In some embodiments, the improved engineered ketoreductase enzymes comprise deletions of the naturally occurring ketoreductase polypeptides or deletions of other engineered ketoreductase polypeptides. In some embodiments, each of the improved engineered ketoreductase enzymes described herein can comprise deletions of the polypeptides described herein. Thus, for each and every embodiment of the ketoreductase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

As described herein, the ketoreductase polypeptides of the disclosure can be in the form of fusion polypeptides in which the ketoreductases polypeptides are fused to other polypeptides, such as antibody tags (e.g., myc epitope) or purifications sequences (e.g., His tags). Thus, the ketoreductase polypeptides can be used with or without fusions to other polypeptides.

In some embodiments, the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised are apparent to those of skill in the art. These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4- carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered ketoreductase enzyme can be targeted to a specific property of the enzyme.

Polynucleotides Encoding Engineered Ketoreductases

In another aspect, the present disclosure provides polynucleotides encoding the engineered ketoreductase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in the Tables in the Examples. In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO:2 has been codon optimized for expression in *E. coli*, but otherwise encodes the naturally occurring ketoreductase of *Lactobacillus kefir*.

In some embodiments, the polynucleotide comprises a nucleotide sequence encoding a ketoreductase polypeptide with an amino acid sequence that has at least about 85%, 86%, 87%, 88%, 89%, 90%, 91%, 92%, 93%, 94%, 95%, 96%, 97%, 98%, or 99% or more sequence identity to any of the reference engineered ketoreductase polypeptides described herein, where the encoded ketoreductase polypeptide comprises an amino acid sequence in which the residue corresponding to X190 of SEQ ID NOS:4, 6, 25, 42 or 238 is not a tyrosine. In some embodiments, the polynucleotide encodes a ketoreductase polypeptide comprising an amino acid sequence in which the residue corresponding to X190 is a non-aromatic residue. In some embodiments, the polynucleotide encodes a ketoreductase polypeptide comprising an amino acid sequence in which the residue corresponding to X190 is alanine, glutamine, threonine, or proline, particularly proline. In some embodiments, the polynucleotide encodes an engineered ketoreductase polypeptide comprising an amino acid sequence selected from SEQ ID NOS:6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, and 238.

In some embodiments, the polynucleotides encoding the engineered ketoreductases are selected from SEQ ID NOS: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, and 237.

In some embodiments, the polynucleotides are capable of hybridizing under highly stringent conditions to a polynucleotide comprising SEQ ID NO:4, wherein the polynucleotide hybridizing under highly stringent conditions has (S)-selectivity in reducing or converting the substrate of structural formula (I) to the product of structural formula (II). In some embodiments, the polynucleotides hybridizing under highly stringent conditions are capable of reducing or converting the substrate of structural formula (III) to the product of structural formula (IV).

In some embodiments, the polynucleotides encode the polypeptides described herein but have about 80% or more sequence identity, about 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered ketoreductase. In some embodiments, the reference polynucleotide is selected from a polynucleotide sequence corresponding to SEQ ID NO:4.

In some embodiments, the engineered ketoreductase sequences comprise sequences that comprise positions identified to be beneficial, as described in the Examples. In some embodiments, the sequences are SEQ ID NO:239 or SEQ ID NO:240. In some further embodiments, the sequences comprise variant sequences derived from SEQ ID NO:239 or SEQ ID NO:240 (i.e., SEQ ID NO:239 or SEQ ID NO:240 is the starting sequence from which the variant sequences are developed).

An isolated polynucleotide encoding an improved ketoreductase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl. Acad. Sci. USA 75: 3727-3731 [1978]), as well as the tac promoter (See e.g., DeBoer et al., Proc. Natl Acad. Sci. USA 80: 21-25 [1983]). Additional suitable promoters are known to those in the art.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters include, but are not limited to those from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase, as well as other useful promoters for yeast host cells (See e.g., Romanos et al., Yeast 8:423-488 [1992]).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase, as well as other useful terminators for yeast host cells known in the art (See e.g., Romanos et al., supra).

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase, as well as additional useful polyadenylation sequences for yeast host cells known in the art (See e.g., Guo et al., Mol. Cell. Biol., 15:5983-5990 [1995]).

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA, as well as additional signal peptides known in the art (See e.g., Simonen et al., Microbiol. Rev., 57: 109-137 [1993]).

Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase, as well as additional useful signal peptide coding regions (See e.g., Romanos et al., 1992, supra).

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Thus, in some embodiments, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector (i.e., a vector that exists as an extrachromosomal entity), the replication of which is independent of chromosomal replication, (e.g., a plasmid, an extrachromosomal element, a minichromosome, or an artificial chromosome). The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker can be a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention can contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori or the origins of replication of plasmids pBR322, pUC19, pACYC177 (which plasmid has the P15A ori), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (See e.g., Ehrlich, Proc. Natl. Acad. Sci. USA 75:1433 [1978]).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present disclosure are commercially available. Suitable commercial expression vectors include, but are not limited to p3×FLAGTM™ expression vectors (Sigma-Aldrich), which include a CMV promoter and hGH polyadenylation site for expression in mammalian host cells and a pBR322 origin of replication and ampicillin resistance markers for amplification in *E. coli*. Other commercially available suitable expression vectors include but are not limited to the pBluescriptII SK(-) and pBK-CMV vectors (Stratagene), and plasmids derived from pBR322 (Gibco BRL), pUC (Gibco BRL), pREP4, pCEP4 (Invitrogen) or pPoly (See, Lathe et al., Gene 57:193-201 [1987]).

Host Cells for Expression of Ketoreductase Polypeptides

In another aspect, the present disclosure provides a host cell comprising a polynucleotide encoding an improved ketoreductase polypeptide of the present disclosure, the polynucleotide being operatively linked to one or more control sequences for expression of the ketoreductase enzyme in the host cell. Host cells for use in expressing the KRED polypeptides encoded by the expression vectors of the present invention are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture media and growth conditions for the above-described host cells are well known in the art.

Polynucleotides for expression of the ketoreductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

*Escherichia coli* W3110 is a host strain that finds use in the present invention, although it is not intended that the present invention be limited to this specific host strain. The expression vector was created by operatively linking a polynucleotide encoding an improved ketoreductase into the plasmid pCK110900 operatively linked to the lac promoter under control of the lacI repressor. The expression vector also contained the P15a origin of replication and the chloramphenicol resistance gene. Cells containing the subject polynucleotide in *Escherichia coli* W3110 can be isolated by subjecting the cells to chloramphenicol selection.

Methods of Generating Engineered Ketoreductase Polypeptides.

In some embodiments, to make the improved KRED polynucleotides and polypeptides of the present disclosure, the naturally-occurring ketoreductase enzyme that catalyzes the reduction reaction is obtained (or derived) from *Lactobacillus* kefir or *Lactobacillus brevis* or *Lactobacillus minor*. In some embodiments, the parent polynucleotide sequence is codon optimized to enhance expression of the ketoreductase in a specified host cell. As an illustration, the parental polynucleotide sequence encoding the wild-type KRED polypeptide of *Lactobacillus* kefir was constructed from oligonucleotides prepared based upon the known polypeptide sequence of *Lactobacillus* kefir KRED sequence available in Genbank database (Genbank accession no. AAP94029 GI:33112056). The parental polynucleotide sequence, designated as SEQ ID NO:3, was codon optimized for expression in *E. coli* and the codon-optimized polynucleotide cloned into an expression vector, placing the expression of the ketoreductase gene under the control of the lac promoter and lacI repressor gene. Clones expressing the active ketoreductase in *E. coli* were identified and the genes sequenced to confirm their identity. The sequence designated (SEQ ID NO:3) was the parent sequence utilized as the starting point for most experiments and library construction of engineered ketoreductases evolved from the *Lactobacillus* kefir ketoreductase.

The engineered ketoreductases can be obtained by subjecting the polynucleotide encoding the naturally occurring ketoreductase to mutagenesis and/or directed evolution methods, as discussed above. Mutagenesis may be performed in accordance with any of the techniques known in the art, including random and site-specific mutagenesis. Directed evolution can be performed with any of the techniques known in the art to screen for improved promoter variants including shuffling. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). The stereochemistry of the products can be ascertained by various known techniques, and as provided in the Examples. Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis (e.g., using the classical phosphoramidite method described by Beaucage et al., Tet. Lett., 22:1859-69 [1981], or the method described by Matthes et al., EMBO J., 3:801-05 [1984], as it is typically practiced in automated synthetic methods). According to the phosphoramidite method, oligonucleotides are synthesized (e.g., in an automatic DNA synthesizer), purified, annealed, ligated and cloned in appropriate vectors. In addition, essentially any nucleic acid can be obtained from any of a variety of commercial sources (e.g., The Midland Certified Reagent Company, Midland, TX, The Great American Gene Company, Ramona, CA, ExpressGen Inc. Chicago, IL, Operon Technologies Inc., Alameda, CA, and many others).

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ (Sigma-Aldrich).

Chromatographic techniques for isolation of the ketoreductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with the ketoreductase. The ketoreductase polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacillus Calmette Guerin) and *Corynebacterium parvum*.

The ketoreductases may be prepared and used in the form of cells expressing the enzymes, as crude extracts, or as isolated or purified preparations. The ketoreductases may be prepared as lyophilizates, in powder form (e.g., acetone powders), or prepared as enzyme solutions. In some embodiments, the ketoreductases can be in the form of substantially pure preparations.

In some embodiments, the ketoreductase polypeptides can be attached to a solid substrate. The substrate can be a solid phase, surface, and/or membrane. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of the substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

Methods of Using the Engineered Ketoreductase Enzymes and Compounds Prepared Therewith The ketoreductase enzymes described herein are capable of catalyzing the asymmetric reduction of the keto group in 7-oxo-5,6-dihydro-5H-cyclopenta(hetero)arene substrates, optionally substituted at one or more of the aryl positions and the 6-position and with nitrogen substitution in the aryl ring, to the corresponding substituted chiral alcohol.

In some embodiments, the ketoreductases are capable of reducing or converting the substrate compound of structural formula (I), tert-butyl 2-(3-chloro-7-oxo-5,6-dihydro-5H-cyclopenta[c]pyridin-6-yl)acetate:

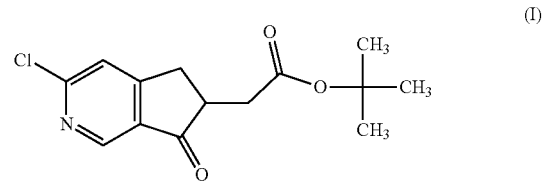 [SMILES: CC(C)(C)OC(=O)CC1Cc2cc(Cl)ncc2C1=O]

(I)

to the corresponding chiral alcohol product (tert-butyl 2-[(6S,7S)-3-chloro-7-hydroxy-6,7-dihydro-5H-cyclopenta[c]pyridin-6-yl]acetate) of structural formula (II):

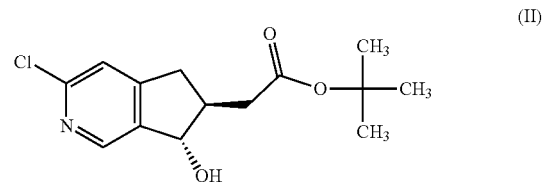 [SMILES: CC(C)(C)OC(=O)C[C@@H]1Cc2cc(Cl)ncc2[C@H]1O]

(II)

In some embodiments, the ketoreductases described herein are capable of reducing or converting 7-oxo-5,6-dihydro-5H-cyclopenta(hetero)arene compounds of structural formula (III):

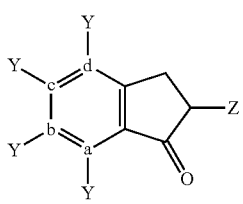

(III)

wherein a, b, c, and d are independently selected from carbon or nitrogen. Y is selected independently from H, halogen, $NH_2$, OH, alkyl, alkenyl, alkynyl, aryl, heteroaryl, alkoxy, when the associated a, b, c, or d atom is carbon. Z is independently selected from H, $(CH_2)_n$alkoxycarbonyl where n=0-6, alkyl, alkenyl, alkynyl, alkoxy, aryl, heteroaryl, to the corresponding chiral alcohol product of structural formula (IV):

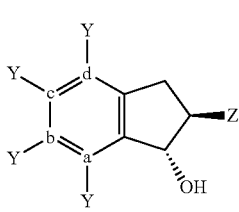

(IV)

The capability of the ketoreductases described herein to catalyze the reduction reaction of a specific further substituted 7-oxo-5,6-dihydro-5H-cyclopenta(hetero)arenes, can be determined by routine experimentation, for example by methods such as described in the Examples. However, it is not intended that the present invention be limited to these specific methods, as other methods known to those skilled in the art may find use.

In some embodiments, the ketoreductases described herein can be used in a method for reducing the 7-oxo-5,6-dihydro-5H-cyclopenta(hetero)arene substrate of formula (III) to corresponding 7-hydroxy-6,7-dihydro-5H-cyclopenta(hetero)arene compound of formula (IV), where the method comprises contacting or incubating the compound of formula (III) with a ketoreductase polypeptide described herein under reaction conditions suitable for reducing or converting the compound of formula (III) to the corresponding substituted 7-hydroxy-6,7-dihydro-5H-cyclopenta(hetero)arene compound of formula (IV). In some embodiments of this method, the substrate is reduced to the product in greater than about 10%, 20%, 30%, 40%, 50%, 60%, 70%, 80%, 90%, or greater diastereomeric excess.

In some embodiments, the ketoreductases described herein can be used in a method for reducing a tert-butyl 2-(3-chloro-7-oxo-5,6-dihydro-5H-cyclopenta[c]pyridin-6-yl)acetate substrate of formula (I) to its corresponding (S)-alcohol product, (tert-butyl 2-[(6S,7S)-3-chloro-7-hydroxy-6,7-dihydro-5H-cyclopenta[c]pyridin-6-yl]acetate), of formula (II), where the method comprises contacting or incubating substrate tert-butyl 2-(3-chloro-7-oxo-5,6-dihydro-5H-cyclopenta[c]pyridin-6-yl)acetate with a ketoreductase polypeptide described herein under reaction conditions suitable for reducing or converting tert-butyl 2-(3-chloro-7-oxo-5,6-dihydro-5H-cyclopenta[c]pyridin-6-yl)acetate to (tert-butyl 2-[(6S,7S)-3-chloro-7-hydroxy-6,7-dihydro-5H-cyclopenta[c]pyridin-6-yl]acetate). In some embodiments, the substrate is reduced to the product with greater than about 2.5 fold improved diastereomeric ratio over SEQ ID NO:4, wherein the ketoreductase polypeptide comprises an amino acid sequence based on the sequence formula of SEQ ID NOS:42, 208, 210, 212, 214, 216, 218, 220, 222, 224, 226, 228, and 238.

In some embodiments, an engineered (S)-selective ketoreductase enzyme derived from a wild-type *Lactobacillus* species ketoreductase enzyme can be used in a method to reduce acetophenone to (S)-1-phenethanol in greater than about 85%, 90%, 91%, 92%, 93%, 94%, 95%, 96%, 97%, 98%, 99%, or 99.9% or more stereomeric excess.

In some embodiments, the substrate is reduced to the product in greater than about 2.5 fold increased diastereomeric ratio over SEQ ID NO:4, wherein the ketoreductase polypeptide used in the method comprises an amino acid sequence selected from SEQ ID NO:42, 208, 210, 212, 214, 216, 218, 220, 222, 224, 226, 228, and 238. In some embodiments of this method, at least about 95% of the substrate is reduced to the product in greater than about 90% diastereomeric excess in less than 24 hours when the method is carried out with the ketoreductase polypeptide at an amount of less than about 2% by weight with respect to the amount of the tert-butyl 2-(3-chloro-7-oxo-5,6-dihydro-5H-cyclopenta[c]pyridin-6-yl)acetate substrate.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, $NADP^+$ (nicotinamide adenine dinucleotide phosphate), NADPH (the reduced form of $NADP^+$), NAD (nicotinamide adenine dinucleotide) and NADH (the reduced form of $NAD^+$). Generally, the reduced form of the cofactor is added to the reaction mixture. The reduced NAD(P)H form can be optionally regenerated from the oxidized $NAD(P)^+$ form using a cofactor regeneration system.

The term "cofactor regeneration system" refers to a set of reactants that participate in a reaction that reduces the oxidized form of the cofactor (e.g., $NADP^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from $NAD^+$ or $NADP^+$, respectively, are known in the art and may be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either $NADP^+$/NADPH or $NAD^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

The terms "glucose dehydrogenase" and "GDH" are used interchangeably herein to refer to an $NAD^+$ or $NADP^+$-dependent enzyme that catalyzes the conversion of D-glucose and $NAD^+$ or $NADP^+$ to gluconic acid and NADH or NADPH, respectively. Equation (3), below, describes the glucose dehydrogenase-catalyzed reduction of $NAD^+$ or $NADP^+$ by glucose.

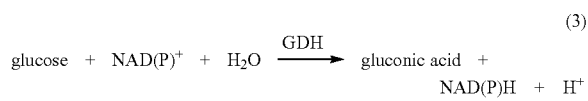

$$\text{glucose} + \text{NAD(P)}^+ + H_2O \xrightarrow{\text{GDH}} \text{gluconic acid} + \text{NAD(P)H} + H^+ \quad (3)$$

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, *Proc. Natl. Acad. Sci. USA* 80:785). The gene sequence of the *B. subtilis* GDH gene, which corresponds to Genbank Acc. No. M12276, was reported by Lampel et al., 1986, *J. Bacteriol.* 166:238-243, and in corrected form by Yamane et al., 1996, *Microbiology* 142:3047-3056 as Genbank Acc. No. D50453. Naturally occurring GDH genes also include those that encode the GDH from *B. cereus* ATCC 14579 (*Nature*, 2003, 423:87-91; Genbank Acc. No. AE017013) and *B. megaterium* (*Eur. J. Biochem.*, 1988, 174:485-490, Genbank Acc. No. X12370; *J. Ferment. Bioeng.*, 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference.

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4 of PCT publication WO 2005/018579, the disclosure of which is incorporated herein by reference. Exemplary non-naturally occurring glucose dehydrogenases are provided in PCT publication WO 2005/018579 as SEQ ID NOS: 62, 64, 66, 68, 122, 124, and 126. The polynucleotide sequences that encode them are provided in PCT publication WO 2005/018579 as SEQ ID NOS: 61, 63, 65, 67, 121, 123, and 125, respectively. All of these sequences are incorporated herein by reference. Additional non-naturally occurring glucose dehydrogenases that are suitable for use in the ketoreductase-catalyzed reduction reactions disclosed herein are provided in U.S. application publication Nos. 2005/0095619 and 2005/0153417, the disclosures of which are incorporated herein by reference.

Glucose dehydrogenases employed in the ketoreductase-catalyzed reduction reactions described herein may exhibit an activity of at least about 10 μmol/min/mg and sometimes at least about $10^2$ μmol/min/mg or about $10^3$ μmol/min/mg, up to about $10^4$ μmol/min/mg or higher in the assay described in Example 4 of PCT publication WO 2005/018579.

The ketoreductase-catalyzed reduction reactions described herein are generally carried out in a solvent. Suitable solvents include water, organic solvents (e.g., ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvent. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9 or below, usually in the range of from about 5 to about 9. In some embodiments, the reduction is carried out at a pH of about 8 or below, often in the range of from about 5 to about 8, and usually in the range of from about 6 to about 8. The reduction may also be carried out at a pH of about 7.8 or below, or 7.5 or below. Alternatively, the reduction may be carried out a neutral pH, i.e., about 7.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

When the glucose/glucose dehydrogenase cofactor regeneration system is employed, the co-production of gluconic acid (pKa=3.6), as represented in equation (3) above causes the pH of the reaction mixture to drop if the resulting aqueous gluconic acid is not otherwise neutralized.

The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a ketoreductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the co-factor regenerating system can comprises a formate dehydrogenase. The terms "formate dehydrogenase" and "FDH" are used interchangeably herein to refer to an NAD$^+$ or NADP$^+$-dependent enzyme that catalyzes the conversion of formate and NAD or NADP to carbon dioxide and NADH or NADPH, respectively. Formate dehydrogenases that are suitable for use as cofactor regenerating systems in the ketoreductase-catalyzed reduction reactions described herein include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases employed in the methods described herein, whether naturally occurring or non-naturally occurring, may exhibit an activity of at least about 1 µmol/min/mg, sometimes at least about 10 µmol/min/mg, or at least about 10$^2$ µmol/min/mg, up to about 10$^3$ µmol/min/mg or higher, and can be readily screened for activity in the assay described in Example 4 of PCT publication WO 2005/018579.

As used herein, the term "formate" refers to formate anion (HCO$_2^-$), formic acid (HCO$_2$H), and mixtures thereof. Formate may be provided in the form of a salt, typically an alkali or ammonium salt (for example, HCO$_2$Na, KHCO$_2$NH$_4$, and the like), in the form of formic acid, typically aqueous formic acid, or mixtures thereof. Formic acid is a moderate acid. In aqueous solutions within several pH units of its pKa (pKa=3.7 in water) formate is present as both HCO$_2^-$ and HCO$_2$H in equilibrium concentrations. At pH values above about pH 4, formate is predominantly present as HCO$_2^-$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like.

For pH values above about pH 5, at which formate is predominantly present as HCO$_2^-$, Equation (4) below, describes the formate dehydrogenase-catalyzed reduction of NAD$^+$ or NADP$^+$ by formate.

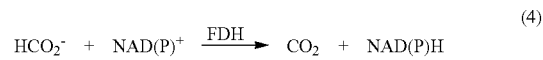

$$HCO_2^- + NAD(P)^+ \xrightarrow{FDH} CO_2 + NAD(P)H \qquad (4)$$

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., KH$_2$PO$_4$), bisulfate salts (e.g., NaHSO$_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

The terms "secondary alcohol dehydrogenase" and "sADH" are used interchangeably herein to refer to an NAD$^+$ or NADP$^+$-dependent enzyme that catalyzes the conversion of a secondary alcohol and NAD$^+$ or NADP$^+$ to a ketone and NADH or NADPH, respectively. Equation (5), below, describes the reduction of NAD$^+$ or NADP$^+$ by a secondary alcohol, illustrated by isopropanol.

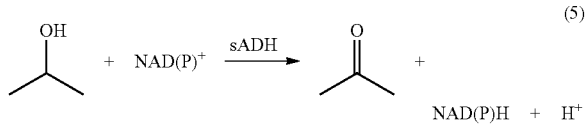

$$\text{(5)}$$

Secondary alcohol dehydrogenases that are suitable for use as cofactor regenerating systems in the ketoreductase-catalyzed reduction reactions described herein include both naturally occurring secondary alcohol dehydrogenases, as well as non-naturally occurring secondary alcohol dehydrogenases. Naturally occurring secondary alcohol dehydrogenases include known alcohol dehydrogenases from, *Thermoanerobium brockii*, *Rhodococcus etythropolis*, *Lactobacillus kefir*, and *Lactobacillus brevis*, and non-naturally occurring secondary alcohol dehydrogenases include engineered alcohol dehydrogenases derived therefrom. Secondary alcohol dehydrogenases employed in the methods described herein, whether naturally occurring or non-naturally occurring, may exhibit an activity of at least about 1 µmol/min/mg, sometimes at least about 10 µmol/min/mg, or at least about 10$^2$ µmol/min/mg, up to about 10$^3$ µmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment the secondary alcohol is isopropanol. Suitable aryl-alkyl carbinols include unsubstituted and substituted 1-arylethanols.

When a secondary alcohol and secondary alcohol dehydrogenase are employed as the cofactor regeneration system, the resulting $NAD^+$ or $NADP^+$ is reduced by the coupled oxidation of the secondary alcohol to the ketone by the secondary alcohol dehydrogenase. Some engineered ketoreductases also have activity to dehydrogenate a secondary alcohol reductant. In some embodiments using secondary alcohol as reductant, the engineered ketoreductase and the secondary alcohol dehydrogenase are the same enzyme.

In carrying out embodiments of the ketoreductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the ketoreductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the stereoselective reduction reactions described herein, the engineered ketoreductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered ketoreductase enzyme and the optional cofactor regeneration enzymes can be transformed into host cells separately or together into the same host cell. For example, in some embodiments one set of host cells can be transformed with gene(s) encoding the engineered ketoreductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered ketoreductase enzyme and the cofactor regeneration enzymes.

Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semi-solid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of ketoreductase substrate employed. The following guidelines can be used to determine the amounts of ketoreductase, cofactor, and optional cofactor regeneration system to use. Generally, keto substrates can be employed at a concentration of about 20 to 300 grams/liter using from about 50 mg to about 5 g of ketoreductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or ketoreductase utilized. In general, the reductant (e.g., glucose, formate, isopropanol) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent.

For improved mixing efficiency when an aqueous co-solvent system is used, the cofactor regeneration system, ketoreductase, and cofactor may be added and mixed into the aqueous phase first. The organic phase may then be added and mixed in, followed by addition of the ketoreductase substrate. Alternatively, the ketoreductase substrate may be premixed in the organic phase, prior to addition to the aqueous phase Suitable conditions for carrying out the ketoreductase-catalyzed reduction reactions described herein include a wide variety of conditions which can be readily optimized by routine experimentation that includes, but is not limited to, contacting the engineered ketoreductase enzyme and substrate at an experimental pH and temperature and detecting product, for example, using the methods described in the Examples provided herein.

The ketoreductase catalyzed reduction is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The reduction reaction is generally allowed to proceed until essentially complete, or near complete, reduction of substrate is obtained. Reduction of substrate to product can be monitored using known methods by detecting substrate and/or product. Suitable methods include gas chromatography, HPLC, and the like. Conversion yields of the alcohol reduction product generated in the reaction mixture are generally greater than about 50%, may also be greater than about 60%, may also be greater than about 70%, may also be greater than about 80%, may also be greater than about 90%, and are often greater than about 97%.

EXPERIMENTAL

Various features and embodiments of the disclosure are illustrated in the following representative examples, which are intended to be illustrative, and not limiting.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); ° C. (degrees Centigrade); RT (room temperature); CDS (coding sequence); DNA (deoxyribonucleic acid); RNA (ribonucleic acid); HPLC (high performance liquid chromatography); FIOPC (fold improvement over positive control); HTP (high throughput); LB (Luria broth); Sigma-Aldrich (Sigma-Aldrich, St. Louis, MO); Millipore (Millipore, Corp., Billerica MA); Difco (Difco Laboratories, BD Diagnostic Systems, Detroit, MI); Daicel (Daicel, West Chester, PA); Genetix (Genetix USA, Inc., Beaverton, OR); Molecular Devices (Molecular Devices, LLC, Sunnyvale, CA); Applied Biosystems (Applied Biosystems, part of Life Technologies, Corp., Grand Island, NY), Agilent (Agilent Technologies, Inc., Santa Clara, CA); Thermo Scientific (part of Thermo Fisher Scientific, Waltham, MA); Corning (Corning, Inc., Palo Alto, CA); and Bio-Rad (Bio-Rad Laboratories, Hercules, CA).

In some experiments, samples were analyzed by reversed phase high performance liquid chromatography (HPLC) to quantify residual substrates and products. Reactions (10 µL) were analyzed across a ChiralPak AS-3R column (100×4.6 mm, 3 µm particle size) (Daicel, West Chester, PA) at 25-50° C. eluting with 30-35% acetonitrile, 65-70% water, and 0.1% phosphoric acid at 1-1.5 ml/min. Reactants and products were quantified by their UV detection at 210 or 254 nm. In one embodiment, samples were analyzed at 30° C. with 35% acetonitrile, 65% water and 0.1% phosphoric acid at 1 ml/min. A racemic mixture of substrate eluted at 8.0 min, product 2a eluted at 4.2 min, 2c eluted at 4.6 min, 2b eluted at 5.3 min, and 2d eluted at 6.1 min.

Example 1

Ketoreductase Gene Construction and Expression Vectors

The wild-type *L. kifer* ketoreductase (KRED) encoding gene was designed for expression in *E. coli* based on the reported amino acid sequence of the ketoreductase and a codon optimization algorithm as described in Example 1 of WO2008/042876, incorporated herein by reference. The gene was synthesized using oligonucleotides composed of 42 nucleotides and cloned into expression vector pCK11 0900 (See, FIG. 3 of US Pat. Appln. Publn. No. 2006/0195947, herein incorporated by reference) under the control of a lac promoter. The expression vector also contained the P15a origin of replication and the chloramphenicol resistance gene. The activity of the wild-type ketoreductase was confirmed as described in WO2008/042876. Polynucleotides encoding engineered ketoreductases of the present disclosure were likewise cloned into vector pCK11 0900 for expression in *E. coli* W311 0. Directed evolution of the KRED gene was carried out by first selecting the parent gene (i.e., SEQ ID NOS: 4, 9, 25, 41) followed by library construction of variant genes in which positions associated with certain structural features were subjected to mutagenesis. These libraries were then plated, grown-up, and screened using HTP assays as described in Examples 2 through 7.

Example 2

Production and Analysis of Engineered KRED Polypeptides

Plasmid libraries obtained through directed evolution and containing evolved ketoreductase genes were transformed into *E. coli* W3110 and placed on Luria-Bertani (LB) agar medium containing 1% glucose and 30 µg/ml chloramphenicol (CAM). After incubation for at least 16 h at 30° C., colonies were picked using a Q-Bot® robotic colony picker (Genetix) into a 96-well shallow well microtiter plate containing 200 µL of LB, 1% glucose, and 30 µg/ml CAM. Cells were grown 18-20 h at 30° C., with shaking at 200 rpm. Twenty µL of this culture was then transferred to 360 µL of Terrific Broth (TB) and 30 µg/ml CAM. After incubation of deep well plates at 30° C. with shaking at 250 rpm for 2.5 h ($OD_{600}$ 0.6-0.8), recombinant gene expression was induced by isopropyl thioglycoside (IPTG) to a final concentration of 1 mM. The plates were then incubated at 30° C. with shaking at 250 rpm for 18-21 h.

Cell cultures were pelleted at 3500×g for 20 min, and their supernatants were discarded. Cell pellets were lysed in 300 µL of 20 mM Tris, 1 mM $MgCl_2$ pH 7.5 with 1 g/L lysozyme and 0.5 g/L polymixin B sulfate by shaking at RT for 2 h. Samples were centrifuged at 3500×g for 20 min to clarify cellular debris, and the supernatant was used to carry out the transformations described in Examples 3 through 7.

Example 3

KRED Variants of SEQ ID NO:4

*E. coli* KRED variants were generated as described in Example 1. To analyze the selectivity of the variants, 25 µL supernatant produced as described in Example 2 was added to a mixture of 50 µL substrate (4 g/L) in isopropanol and 25 µL of 4 g/L NADP in 400 mM sodium phosphate pH 9.0. Reactions were incubated at 50° C. for 1 h, and quenched via addition of 100 µL $CH_3CN$. The quenched mixture (100 µL) was added to 50 µL of 0.3% phosphoric acid, mixed briefly. Reaction samples (10 µL) were analyzed by reversed phase HPLC to quantify residual substrates and products as described above. Significantly improved variants are provided in Table 4.1, below.

TABLE 4.1

Variants With Improved 2a: 2c Selectivity Compared to SEQ ID NO: 4

|   | Amino acid Substitutions Relative | Selectivity |
|---|---|---|
| 6 | F145W; D150P | ++ |
| 8 | F249K | + |

TABLE 4.1-continued

Variants With Improved 2a: 2c Selectivity
Compared to SEQ ID NO: 4

| SEQ ID NO: | to SEQ ID NO: 4 | Improvement |
|---|---|---|
| 10 | F249R | + |
| 12 | P94G; F249K | + |
| 14 | P94G; P190W | + |
| 16 | V144G | ++ |
| 18 | V144G; F145W | ++ |

Key for Table 4.1
+++   >2.5
++    >1.8 and <2.5
+     >1.3 and <1.8

Example 4

KRED Variants of SEQ ID NO:10

*E. coli* KRED variants were generated as described in Example 1. To analyze the selectivity of the variants, 25 µL supernatant produced as escribed in Example 2 supernatant was added to 180 µL of 20 mM Tris, 1 mM $MgCl_2$ pH 7.5. The diluted supernatant (25 µL) was added to a mixture of 50 µL substrate (2 g/L) in isopropanol and 25 µL of 4 g/L NADP in 400 mM sodium phosphate pH 9.0. Reactions were incubated at 50° C. for 1 h, and quenched via addition of 100 µL $CH_3CN$. The quenched mixture (100 µL) was added to 50 µL of 0.3% phosphoric acid, mixed briefly. Reaction samples (10 µL) were analyzed by reversed phase HPLC to quantify residual substrates and products as described above. Significantly improved variants are provided in Table 5.1, below.

TABLE 5.1

Variants With Improved 2a: 2c Selectivity
Compared to SEQ ID NO: 10

| SEQ ID NO: | Amino acid Substitutions Relative to SEQ ID NO: 10 | Selectivity Improvement |
|---|---|---|
| 20 | D150W; F206Y; K211I | + |
| 22 | F145W; D150F; T153C; P190A; D198G | + |
| 24 | F145W; D150W; T153C; F206Y; K211H | + |
| 26 | F145W; D150W; T153C; K211E | + |
| 28 | F145W; P190A | + |
| 30 | F145W; T153C; K211I | + |
| 32 | F206Y; K211I | + |
| 34 | P190A; D198G; F206Y; K211H | + |
| 36 | P190A; F206Y | + |
| 38 | T153C; P190A; F206Y; K211S | + |

Key for Table 5.1
+++   >2.5
++    >1.8 and <2.5
+     >1.3 and <1.8

Example 5

KRED Variants of SEQ ID NO:26

*E. coli* KRED variants were generated as described in Example 1. To analyze the selectivity of the variants, 25 µL supernatant produced as described in Example 2 was added to a mixture of 50 µL substrate (1 g/L) in isopropanol and 25 µL of 0.4 g/L NADP in 400 mM sodium phosphate pH 9.0. Reactions were incubated at 50° C. for 2.5 h, and quenched via addition of 100 µL $CH_3CN$. The quenched mixture (100 µL) was added to 50 µL of 0.3% phosphoric acid, mixed briefly. Reaction samples (10 NL) were analyzed by reversed phase HPLC to quantify residual substrates and products as described above. Significantly improved variants are provided in Table 6.1, below.

TABLE 6.1

Variants With Improved 2a: 2c 1 Selectivity
Compared to SEQ ID NO: 26

| SEQ ID NO: | Amino acid Substitutions Relative to SEQ ID NO: 26 | Selectivity Improvement |
|---|---|---|
| 40 | C153T; R209M | ++ |
| 42 | P94M; C153T; Y199E | +++ |
| 44 | T212E | ++ |
| 46 | C153T; G201N; T212G | ++ |
| 48 | T212H | ++ |
| 50 | P190Q | ++ |
| 52 | C153H; A175T | ++ |
| 54 | T212R | ++ |
| 56 | R209I | + |
| 58 | R209F | ++ |
| 60 | P213M | ++ |
| 62 | P213D | ++ |
| 64 | R209E | ++ |
| 66 | C153T; A202H | + |
| 68 | R209W | + |
| 70 | P213R | ++ |
| 72 | P213K | + |
| 74 | P213E | + |
| 76 | C153T; S207D | + |
| 78 | A202H | + |
| 80 | P213T | + |
| 82 | R209T | + |
| 84 | P94Q | + |
| 86 | A202F | + |
| 88 | C153T; P213H | + |
| 90 | R209V | + |
| 92 | C153T; A202Y | + |
| 94 | C153T; M196N | + |
| 96 | P213N | + |
| 98 | E211P | + |
| 100 | S207D | + |
| 102 | P213G | + |
| 104 | C153H | + |
| 106 | A202Y | + |
| 108 | R209G | + |
| 110 | T210L | + |
| 112 | C153T; S207G | + |
| 114 | C153T; E203L | + |
| 116 | C153T; T210P | + |
| 118 | T212G | + |
| 120 | M196K | + |
| 122 | I217N | + |
| 124 | I147L; A202Y | + |
| 126 | S207Y | + |
| 128 | A202R | + |
| 130 | R209Y | + |
| 132 | C153T; F206H | + |
| 134 | P190L; M196I | + |
| 136 | C153T; F206W | + |
| 138 | C153T; E203W | + |

Key for Table 6.1
+++   >2.5
++    >1.8 and <2.5
+     >1.3 and <1.8

Example 6

KRED Variants of SEQ ID NO:42

E. coli KRED variants were generated as described in Example 1. To analyze the selectivity of the variants, 30 μL supernatant produced as described in example 2 was added to a mixture of 75 μL substrate (20 g/L) in isopropanol and 45 μL of 0.33 g/L NADP in 333 mM sodium phosphate pH 8.0. Reactions were incubated at 30° C. for 1 h, and quenched via addition of 100 μL CH$_3$CN. The quenched mixture (100 μL) was added to 50 μL of 0.3% phosphoric acid, mixed briefly. Reaction samples (10 μL) were analyzed by reversed phase HPLC to quantify residual substrates and products as described above. Significantly improved variants are provided in Table 7.1, below.

TABLE 7.1

Samples With Improved 2a: 2c Selectivity Compared to SEQ ID NO: 42

| SEQ ID NO: | Amino acid Substitutions Relative to SEQ ID NO: 42 | Selectivity Improvement |
|---|---|---|
| 140 | P190L; M196N; I217H | + |
| 142 | T102D; W150D | + |
| 144 | P190T; T212N | + |
| 146 | T212N; Q252W | + |
| 148 | R209G | ++ |
| 150 | L110E | ++ |
| 152 | M196N | ++ |
| 154 | T212A; T250G | ++ |
| 156 | G149S; W150D; E203W | ++ |
| 158 | D197Y; Q252W | ++ |
| 160 | T212A; Q252W | ++ |
| 162 | N114G; M196H | ++ |
| 164 | W150D; E203G | ++ |
| 166 | M196Q | ++ |
| 168 | M196H; T212A | ++ |
| 170 | T212P | ++ |
| 172 | M94Q; T212H | ++ |
| 174 | G149S; W150D | ++ |
| 176 | T212N; T250G | ++ |
| 178 | M196H; D197Y | ++ |
| 180 | D197Y; T250G; Q252W | ++ |
| 182 | T212A; T250G; Q252W | ++ |
| 184 | M205T; S207V; T212A; Q252W | ++ |
| 186 | M94Q; P213G | ++ |
| 188 | L110E; T212V | ++ |
| 190 | W150D; A158V | +++ |
| 192 | W150D; A158V; D198S | +++ |
| 194 | T153P; T212P | +++ |
| 196 | W150D; D198S; E203W | +++ |
| 198 | P213M | +++ |
| 200 | W150D; D198S; E203L | +++ |
| 202 | W150D | +++ |
| 204 | T212V; P213N | +++ |
| 206 | T212R | +++ |
| 208 | P213E | +++ |
| 210 | M196H | +++ |
| 212 | P213T | +++ |
| 214 | P213G | +++ |
| 216 | T212E; P213G | +++ |
| 218 | L110W; P213N | +++ |
| 220 | P213N | +++ |
| 222 | T212G; P213N | +++ |
| 224 | T212H; P213K | +++ |
| 226 | P213K | +++ |
| 228 | T212R; P213G | +++ |
| 230 | A68V | + |
| 232 | G135K | |

TABLE 7.1-continued

Samples With Improved 2a: 2c Selectivity Compared to SEQ ID NO: 42

| | | |
|---|---|---|
| 234 | D233T | |
| 236 | D233Q | |
| 238 | D173L; R249G | +++ |

Key for Table 7.2
+++  >2.5
++   >1.8 and <2.5
+    >1.3 and <1.8

Example 7

Production of Engineered Polypeptides (Shake Flask Scale Production of KREDs) and Performance Validation Plasmid libraries obtained through directed evolution and containing evolved ketoreductase genes were transformed into E. coli W3110 and placed on Luria-Bertani (LB) agar medium containing 1% glucose and 30 μg/ml chloramphenicol (CAM). After incubation for at least 16 h at 30° C., colonies were picked into 50 mL of LB, 1% glucose, and 30 μg/ml CAM. Cells were grown 18-20 h at 30° C., with shaking at 250 rpm. This culture was then transferred into Terrific Broth (TB) and 30 μg/ml CAM at a final OD$_{600}$ of 0.2 and a final volume of 250 mL. After incubation of the flasks at 30° C. with shaking at 250 rpm for 2.5 h (OD$_{600}$ 0.6-0.8), recombinant gene expression was induced by isopropyl thioglycoside (IPTG) to a final concentration of 1 mM. The flask was then incubated at 30° C. with shaking at 250 rpm for 18-21 h. Cells were pelleted at 3500×g for 20 min, and the supernatant was discarded. The cell pellet was washed 3× in 30 mL ice cold 50 mM sodium phosphate pH 7.5, resuspended in 12 ml of the same buffer, and lysed using a cell disruptor at 18-20 kpsi. Lysates were clarified at 10000×g for 30 min, and clarified supernatants were lyophilized to an off white powder.

To evaluate the final compound under process like conditions, 500 μL of isopropanol was added to 50 mg of substrate followed by 500 μL of 200 mM sodium phosphate pH 8.0, 0.2 g/L NADP, and 1 g/L of lyophilized powder of SEQ ID NO:238 generated as described above. Reactions were heated to 50° C. with shaking at 950 rpm for 24 h resulting in 95% conversion of substrate to product and a 92% diastereomeric excess of 2a to 2c. Reaction samples were analyzed by reversed phase HPLC to quantify residual substrates and products as described above.

While various specific embodiments have been illustrated and described, it will be appreciated that various changes can be made without departing from the spirit and scope of the invention(s).

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed is:

1. An engineered polypeptide comprising an amino acid sequence with at least 95% sequence identity to SEQ ID NO: 240, wherein the residue corresponding to X150 is a tryptophan, the residue corresponding to X173 is a non-polar or aliphatic residue, the residue corresponding to X211 is an aromatic, acidic, or polar residue, and wherein the residue corresponding to X249 is glycine and wherein said polypeptide has ketoreductase activity with at least 2-fold greater selectivity to the chiral compound 2a relative to chiral compound 2c as compared to SEQ ID NO:2.

2. The engineered polypeptide of claim 1, wherein said amino acid sequence further comprises at least one of the following:
   the residue corresponding to X68 is a non-polar, or aliphatic residue;
   the residue corresponding to X94 is a polar, or non-polar residue;
   the residue corresponding to X102 is an acidic residue;
   the residue corresponding to X110 is an acidic, or aromatic residue;
   the residue corresponding to X114 is a non-polar residue;
   the residue corresponding to X135 is a basic residue;
   the residue corresponding to X144 is a non-polar, or aromatic residue;
   the residue corresponding to X145 is an aromatic residue;
   the residue corresponding to X147 is a non-polar, or aliphatic residue;
   the residue corresponding to X149 is a polar residue;
   the residue corresponding to X153 is a polar, or aromatic residue;
   the residue corresponding to X158 is a non-polar, or aliphatic residue;
   the residue corresponding to X175 is a polar residue;
   the residue corresponding to X190 is an aromatic, aliphatic, non-polar, or polar residue;
   the residue corresponding to X196 is an aromatic, polar, basic, non-polar, or aliphatic residue;
   the residue corresponding to X197 is an aromatic residue;
   the residue corresponding to X198 is a non-polar, polar residue;
   the residue corresponding to X199 is an acidic residue;

the residue corresponding to X201 is a polar residue;
the residue corresponding to X202 is an aromatic, or basic residue;
the residue corresponding to X203 is an aromatic, non-polar, or aliphatic residue;
the residue corresponding to X205 is a polar residue;
the residue corresponding to X206 is an aromatic residue;
the residue corresponding to X207 is an aromatic, acidic, non-polar, or aliphatic residue;
the residue corresponding to X209 is an aromatic, acidic, non-polar, polar, or aliphatic residue;
the residue corresponding to X210 is a non-polar, or aliphatic residue;
the residue corresponding to X212 is an aromatic, basic, non-polar, aliphatic, or acidic residue;
the residue corresponding to X213 is an aromatic, basic, acidic, polar, non-polar, or aliphatic residue;
the residue corresponding to X217 is a polar, or aromatic residue;
the residue corresponding to X233 is a polar residue;
the residue corresponding to X250 is a non-polar residue; and
the residue corresponding to X252 is an aromatic residue.

3. The engineered polypeptide of claim 1, comprising at least one substitution selected from X68V, X94G/M/Q, X102D, X110E/W, X114G, X135K, X144G/W, X145W, X147L, X149S, X153H/P/T/V/C, X158V, X173L, X175T, X196H/I/K/N/Q, X196I, X196K/N/Q, X197Y, X198G/S, X199E, X201N, X202F/H/R/Y, X203G/L/W, X205T, X206H/W/Y, X207D/G/V/Y, X209E/F/G/I/M/T/V/W, X210L/P, X211E/H/P/S, X212A/E/G/H/N/P/R/V, X213D/E/G/H/K/M/N/R, X217H/N, X233Q/T, X250G, and X252W.

4. The engineered polypeptide of claim 1, comprising a substitution at position X190 as compared to SEQ ID NO: 2.

5. The engineered polypeptide of claim 4, wherein the substitution at position X190 is selected from P, A, T, or Q.

6. An engineered polypeptide of claim 1 having ketoreductase activity, wherein the polypeptide comprises SEQ ID NO: 240.

* * * * *

SEQUENCE LISTING

<160> NUMBER OF SEQ ID NOS: 246

<210> SEQ ID NO 1
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 1

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagta ttgaggggtt cgtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat ggcgaaccg     660 aatgacatcg catggatctg tgtgtacctg gcatctgacg aatcgaaatt tgcgacgggt     720
gcagaatttg tggtcgacgg cgggtatacc gcacagtga                           759
```

<210> SEQ ID NO 2
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 2

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160
```

```
Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Tyr Ile Lys
        180                 185                 190

Thr Pro Leu Val Asp Asp Leu Glu Gly Ala Glu Glu Met Met Ser Gln
    195                 200                 205

Arg Thr Lys Thr Pro Met Gly His Ile Gly Glu Pro Asn Asp Ile Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

```
<210> SEQ ID NO 3
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 3
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa agcgttgaa     300 gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgttcgggat tgtaggcgac cgactaccg gggcatactg tgcttccaag     480
ggggcggtac gtatcatgtc gaaaagcgca gcgctggatt gcgcactgaa ggactacgat    540
gtgcgtgtca acacagtaca tccgggcccc atcaagaccc cgatgatgga tgattatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggttcacc gcacagtga                          759
```

```
<210> SEQ ID NO 4
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 4

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60
```

```
Ser Asp Glu Ala Gly Trp Pro Lys Leu Phe Asp Thr Thr Glu Glu Ala
 65                  70                  75                  80

Phe Gly Pro Val Thr Thr Val Val Asn Asn Ala Gly Ile Pro Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250

<210> SEQ ID NO 5
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 5
atgaccgatc gtctgaaggg caaagtagcc atcgtaaccg cgggacacaa aggtatcggt      60
ttggcaatcg ccgataaatt tgtagaggag ggtgcgaaag tagttattac tggtcgtcgt     120
gcggatgtag tgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300 gacactacca cggaggaatg gcgtaaactg ctgtccgtta atctggatgg tgttttttc      360 ggcacccgtc tgggcattca gcgcatgaaa ataaaggct tgggcgctag catcatcaat      420
atgagcagtg tgtggggat tgtaggcccg ccgactaccg ggcatactg tgcttccaag       480 ggggcggtac gtatcatgtc gaaaagcgca gcgctggatt gcgcactgaa ggactacgat     540
gtgcgtgtca acacagtaca tccggggccc atcaagaccc cgatgatgga tgattatgaa     600
ggtgctgagg aaatgttttc acagcgtacg aaaaacccta tgggtcacat tggcgaaccg     660
aatgacatcg catgggtctg tgtgtacctg gcatctgacg aatcgaaatt tgcgacgggt     720
gcagaatttg tggtcgacgg cgggttcacc gcacagtga                           759

<210> SEQ ID NO 6
<211> LENGTH: 252
<212> TYPE: PRT
<213> ORGANISM: Artificial Sequence
<220> FEATURE:
```

<223> OTHER INFORMATION: Aldo-keto reductase variant from Lactobacillus kefiri

<400> SEQUENCE: 6

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Pro Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Tyr Glu Gly Ala Glu Met Phe Ser Gln
        195                 200                 205
Arg Thr Lys Thr Pro Met Gly His Ile Gly Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Phe Thr Ala Gln
                245                 250
```

<210> SEQ ID NO 7
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 7

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgttcgggat tgtaggcgac ccgactaccg gggcatactg tgcttccaag     480
```

```
gggggcggtac gtatcatgtc gaaaagcgca gcgctggatt gcgcactgaa ggactacgat      540
gtgcgtgtca acacagtaca tccgggcccc atcaagaccc cgatgatgga tgattatgaa      600
ggtgctgagg aaatgttttc acagcgtacg aaaaccccta tgggtcacat tggcgaaccg      660
aatgacatcg catgggtctg tgtgtacctg gcatctgacg aatcgaaatt tgcgacgggt      720
gcagaatttg tggtcgacgg cgggaaaacc gcacagtga                             759
```

```
<210> SEQ ID NO 8
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 8
```

| | | | | | | | | | | | | | | |
|---|---|---|---|---|---|---|---|---|---|---|---|---|---|---|
| Met | Thr | Asp | Arg | Leu | Lys | Gly | Lys | Val | Ala | Ile | Val | Thr | Gly | Gly | Thr |
| 1 | | | | 5 | | | | | 10 | | | | | 15 | |

Gln Gly Ile Gly Leu Ala Ile Ala Asp Lys Phe Val Glu Glu Gly Ala
         20                  25                  30

Lys Val Val Ile Thr Gly Arg Arg Ala Asp Val Gly Glu Lys Ala Ala
     35                  40                  45

Lys Ser Ile Gly Gly Thr Asp Val Ile Arg Phe Val Gln His Asp Val
 50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Lys Thr Ala Gln
                245                 250

```
<210> SEQ ID NO 9
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri
```

```
<400> SEQUENCE: 9
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcaggattc cggtggtaa aagcgttgaa         300 gacactacca cggaggaatg gcgtaaactg ctgtccgtta atctggatgg tgttttttc        360 ggcacccgtc tgggcattca gcgcatgaaa aataaaggct gggcgctag catcatcaat       420 atgagcagtg tgttcgggat gtaggcgac ccgactaccg gggcatactg tgcttccaag        480
ggggcggtac gtatcatgtc gaaaagcgca gcgctggatt gcgcactgaa ggactacgat       540
gtgcgtgtca acacagtaca tccgggcccc atcaagaccc cgatgatgga tgattatgaa       600
ggtgctgagg aaatgttttc acagcgtacg aaaaccccta tgggtcacat tggcgaaccg       660
aatgacatcg catgggtctg tgtgtacctg gcatctgacg aatcgaaatt tgcgacgggt       720
gcagaatttg tggtcgacgg cgggaggacc gcacagtaa                              759
```

<210> SEQ ID NO 10
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 10

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205
```

Arg Thr Lys Thr Pro Met Gly His Ile Gly Glu Pro Asn Asp Ile Ala
            210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
            245                 250

<210> SEQ ID NO 11
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 11
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattg gcgtggttaa aagcgttgaa     300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgttcgggat tgtaggcgac ccgactaccg ggcatactg tgcttccaag     480 ggggcggtac gtatcatgtc gaaaagcgca gcgctggatt gcgcactgaa ggactacgat     540
gtgcgtgtca acacagtaca tccgggcccc atcaagaccc cgatgatgga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggaaaacc gcacagtga                           759

<210> SEQ ID NO 12
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 12

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

```
Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Lys Thr Ala Gln
                245                 250
```

<210> SEQ ID NO 13
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 13

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattg gcgtggttaa aagcgttgaa     300
gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagtg tgttcgggat tgtaggcgac ccgactaccg gggcatactg tgcttccaag     480
ggggcggtac gtatcatgtc gaaaagcgca gcgctggatt gcgcactgaa ggactacgat     540
gtgcgtgtca acacagtaca tccgggctgg atcaagaccc cgatgatgga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggttcacc gcacagtga                            759
```

<210> SEQ ID NO 14
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 14

```
Met Thr Asp Arg Leu Lys Gly Lys Val Ala Ile Val Thr Gly Gly Thr
1               5                   10                  15
```

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
 50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Gly Val Val
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Trp Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250

<210> SEQ ID NO 15
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 15
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcaggattcc ggtggttaa aagcgttgaa        300 gacactacca cggaggaatg gcgtaaactg ctgtccgtta atctggatgg tgtttttttc       360
ggcacccgtc tgggcattca gcgcatgaaa aataaaggct gggcgctag catcatcaat       420 atgagcagtg gcttcgggat tgtaggcgac ccgactaccg gggcatactg tgcttccaag       480
ggggcggtac gtatcatgtc gaaaagcgca gcgctggatt gcgcactgaa ggactacgat       540
gtgcgtgtca acacagtaca tccgggcccc atcaagaccc cgatgatgga tgattatgaa       600
ggtgctgagg aaatgttttc acagcgtacg aaaaccccta tgggtcacat tggcgaaccg       660

```
aatgacatcg catgggtctg tgtgtacctg gcatctgacg aatcgaaatt tgcgacgggt    720
gcagaatttg tggtcgacgg cgggttcacc gcacagtga                          759
```

<210> SEQ ID NO 16
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 16

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Gly
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 17
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 17

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
```

```
cagcacgatg tatccgatga agcaggctgg cctaaactgt tcgacaccac cgaggaggca    240
ttcggcccgg ttacgaccgt agtgaacaat gcagggattc cggtggttaa aagcgttgaa    300
gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg gctgggggat tgtaggcgac ccgactaccg gggcatactg tgcttccaag    480
ggggcggtac gtatcatgtc gaaaagcgca gcgctggatt gcgcactgaa ggactacgat    540
gtgcgtgtca acacagtaca tccgggcccc atcaagaccc cgatgatgga tgattatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggttcacc gcacagtga                          759
```

<210> SEQ ID NO 18
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri
<400> SEQUENCE: 18

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Gly
    130                 135                 140

Trp Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 19
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 19

```
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa aagcgttgaa    300
gacactacca cggaggaatg gcgtaaactg ctgtccgtta atctggatgg tgtttttttc    360
ggcacccgtc tgggcattca gcgcatgaaa aataaaggct gggcgctag catcatcaat    420
atgagcagtg ttttttgggat tgtaggctgg ccgactaccg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgtattc acagcgtacg ataacccta tgggtcacat ggcgaaccg     660
aatgacatcg catgggtctg tgtgtacctg gcatctgacg aatcgaaatt tgcgacgggt    720
gcagaatttg tggtcgacgg cgggagaacc gcacagtaa                           759
```

<210> SEQ ID NO 20
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 20

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Phe Gly Ile Val Gly Trp Pro Thr Thr Gly Ala Tyr Cys Ala Ser Lys
145                 150                 155                 160
```

```
Gly Ala Val Arg Ile Met Ser Lys Ser Ala Leu Asp Cys Ala Leu
            165                 170                 175

Lys Asp Tyr Asp Val Arg Val Asn Thr Val His Pro Gly Pro Ile Lys
        180                 185                 190

Thr Pro Met Met Asp Asp Tyr Glu Gly Ala Glu Met Tyr Ser Gln
        195                 200                 205

Arg Thr Ile Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 21
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 21
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattcc ggtggttaa aagcgttgaa      300 gacactacca cggaggaatg gcgtaaactg ctgtccgtta atctggatgg tgtttttttc     360
ggcacccgtc tgggcattca gcgcatgaaa aataaaggct gggcgctag catcatcaat     420 atgagcagtg tgtggggat gtaggctttt ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcgcg atcaagaccc cgatgatgga tgggtatgaa     600
ggtgctgagg aaatgttttc acagcgtacg aagacccca tgggtcacat tggcgaaccg      660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 22
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 22

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60
```

```
Ser Asp Glu Ala Gly Trp Pro Lys Leu Phe Asp Thr Thr Glu Glu Ala
 65                  70                  75                  80

Phe Gly Pro Val Thr Thr Val Val Asn Asn Ala Gly Ile Pro Val Val
                 85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Phe Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Met Met Asp Gly Tyr Glu Gly Ala Glu Glu Met Phe Ser Gln
            195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 23
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 23
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat cgctttgtc      180 cagcacgatg tatccgatga agcaggctgg cctaaactgt tcgacaccac cgaggaggca     240
ttcggcccgg ttacgaccgt agtgaacaat gcaggattc cggtggtaa aagcgttgaa       300 gacactacca cggaggaatg cgtaaactg ctgtccgtta atctggatgg tgtttttttc      360
ggcacccgtc tgggcattca gcgcatgaaa aataaaggct gggcgctag catcatcaat     420 atgagcagtg tgtggggat gtaggctgg ccgacttgcg gggcatactg tgcttccaag       480
ggggcggtac gtatcatgtc gaaaagcgca gcgctggatt gcgcactgaa ggactacgat     540
gtgcgtgtca acacagtaca tccgggcccc atcaagaccc cgatgatgga tgattatgaa    600
ggtgctgagg aaatgtattc acagcgtacg cacaccccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                          759

<210> SEQ ID NO 24
<211> LENGTH: 252
<212> TYPE: PRT
<213> ORGANISM: Artificial Sequence
```

<220> FEATURE:
<223> OTHER INFORMATION: Aldo-keto reductase variant from Lactobacillus kefiri

<400> SEQUENCE: 24

```
Met Thr Asp Arg Leu Lys Gly Lys Val Ala Ile Val Thr Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Lys Ala Ala
            35                  40                  45

Lys Ser Ile Gly Gly Thr Asp Val Ile Arg Phe Val Gln His Asp Val
50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Pro Val Val
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Tyr Ser Gln
            195                 200                 205

Arg Thr His Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 25
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 25

```
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa agcgttgaa     300 gacactacca cggaggaatg gcgtaaactg ctgtccgtta atctggatgg tgttttttc     360 ggcacccgtc tgggcattca gcgcatgaaa aataaaggct gggcgctag catcatcaat    420
```

```
atgagcagtg tgtgggggat gtaggctgg ccgacttgcg gggcatactg tgcttccaag      480
ggggcggtac gtatcatgtc gaaaagcgca gcgctggatt gcgcactgaa ggactacgat      540
gtgcgtgtca acacagtaca tccgggcccg atcaagaccc cgatgatgga tgattatgaa      600
ggtgctgagg aaatgttttc acagcgtacg gagacccta tgggtcacat ggcgaaccg       660 aatgacatcg catgggtctg tgtgtacctg gcatctgacg aatcgaaatt tgcgacgggt      720
gcagaatttg tggtcgacgg cgggaggacc gcacagtaa                            759
```

<210> SEQ ID NO 26
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri
<400> SEQUENCE: 26

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Pro Val Val
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
    195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 27
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 27

```
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcagggattc cggtggttaa agcgttgaa        300 gacactacca cggaggaatg gcgtaaactg ctgtccgtta atctggatgg tgttttttc        360 ggcacccgtc tgggcattca gcgcatgaaa aataaaggct gggcgctag catcatcaat        420 atgagcagtg tgtgggggat tgtaggcgat ccgactacag gggcatactg tgcttccaag       480
ggggcggtac gtatcatgtc gaaaagcgca gcgctggatt gcgcactgaa ggactacgat       540
gtgcgtgtca acacagtaca tccgggcgcg atcaagaccc cgatgatgga tgattatgaa       600
ggtgctgagg aaatgttttc acagcgtacg aaaaccccta tgggtcacat ggcgaaccg        660 aatgacatcg catgggtctg tgtgtacctg gcatctgacg aatcgaaatt tgcgacgggt       720
gcagaatttg tggtcgacgg cgggaggacc gcacagtaa                              759
```

<210> SEQ ID NO 28
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 28

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Met Met Asp Asp Tyr Glu Gly Ala Glu Glu Met Phe Ser Gln
        195                 200                 205
```

```
Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 29
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 29
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300 gacactacca cggaggaatg gcgtaaactg ctgtccgtta atctggatgg tgttttttc     360 ggcacccgtc tgggcattca cgcatgaaa aataaaggct ggcgctag catcatcaat      420 atgagcagtg tgtgggggat gtaggcgat ccgacttgcg gggcatactg tgcttccaag      480
ggggcggtac gtatcatgtc gaaaagcgca gcgctggatt gcgcactgaa ggactacgat     540
gtgcgtgtca acacagtaca tccgggcccc atcaagaccc cgatgatgga tgattatgaa     600
ggtgctgagg aaatgttttc acagcgtacg attaccccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                           759

<210> SEQ ID NO 30
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 30

Met Thr Asp Arg Leu Lys Gly Lys Val Ala Ile Val Thr Gly Gly Thr
1                   5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110
```

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
        130                 135                 140

Trp Gly Ile Val Gly Asp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Ile Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 31
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 31
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt cgacaccac cgaggaggca    240 ttcggcccgg ttacgaccgt agtgaacaat gcaggattc cggtggtaa aagcgttgaa     300 gacactacca cggaggaatg gcgtaaactg ctgtccgtta tctggatgg tgttttttc     360 ggcacccgtc tgggcattca gcgcatgaaa aataaaggct tgggcgctag catcatcaat    420
atgagcagtg tgttcgggat tgtaggcgat ccgactaccg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgtattc acagcgtacg ataaccccta tgggtcacat tggcgaaccg    660
aatgacatcg catgggtctg tgtgtacctg gcatctgacg aatcgaaatt tgcgacgggt    720
gcagaatttg tggtcgacgg cgggagaacc gcacagtaa                          759

<210> SEQ ID NO 32
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 32

Met Thr Asp Arg Leu Lys Gly Lys Val Ala Ile Val Thr Gly Gly Thr
1               5                   10                  15

```
Gln Gly Ile Gly Leu Ala Ile Ala Asp Lys Phe Val Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Phe Gly Ile Val Gly Asp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Tyr Glu Gly Ala Glu Met Tyr Ser Gln
        195                 200                 205
Arg Thr Ile Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250
```

<210> SEQ ID NO 33
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 33

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa aagcgttgaa     300
gacactacca cggaggaatg gcgtaaactg ctgtccgtta atctggatgg tgttttcttc     360
ggcacccgtc tgggcattca gcgcatgaaa aataaaggct gggcgctag catcatcaat     420
atgagcagtg tgttcgggat tgtaggcgac ccgactacag gggcatactg tgcttccaag     480
ggggcggtac gtatcatgtc gaaaagcgca gcgctggatt gcgcactgaa ggactacgat     540
gtgcgtgtca acacagtaca tccgggcgcg atcaagaccc cgatgatgga tgggtatgaa     600
ggtgctgagg aaatgtattc acagcgtacg cacaccccta tgggtcacat tggcgaaccg     660
```

```
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 34
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 34

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Met Met Asp Gly Tyr Glu Gly Ala Glu Met Tyr Ser Gln
        195                 200                 205

Arg Thr His Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 35
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 35

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
```

-continued

```
gcggatgtag gtgaaaaggc cgccaaatca atcggcggca ctgatgttat tcgctttgtc      180
cagcacgatg tatccgatga agcaggctgg cctaaactgt tcgacaccac cgaggaggca      240
ttcggcccgg ttacgaccgt agtgaacaat gcagggattc cggtggttaa aagcgttgaa      300
gacactacca cggaggaatg gcgtaaactg ctgtccgtta atctggatgg tgttttttc       360 ggcacccgtc tgggcattca gcgcatgaaa aataaaggct gggcgctag catcatcaat      420 atgagcagtg tgttcgggat tgtaggcgac ccgactaccg gggcatactg tgcttccaag      480
ggggcggtac gtatcatgtc gaaaagcgca gcgctggatt gcgcactgaa ggactacgat      540
gtgcgtgtca acacagtaca tccgggcgcg atcaagaccc cgatgatgga tgattatgaa      600
ggtgctgagg aaatgtattc acagcgtacg aaaacccta tgggtcacat tggcgaaccg       660
aatgacatcg catgggtctg tgtgtacctg catctgacg aatcgaaatt tgcgacgggt       720
gcagaatttg tggtcgacgg cgggaggacc gcacagtaa                            759
```

<210> SEQ ID NO 36
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 36

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Met Met Asp Asp Tyr Glu Gly Ala Glu Glu Met Tyr Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 37
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 37

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattc cggtggttaa aagcgttgaa      300
gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagtg tgttcgggat tgtaggcgat ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcgcg atcaagaccc cgatgatgga tgattatgaa     600
ggtgctgagg aaatgtattc acagcgtacg tctacccta tgggtcacat ggcgaaccg      660 aatgacatcg catgggtctg tgtgtacctg gcatctgacg aatcgaaatt tgcgacgggt     720
gcagaatttg tggtcgacgg cgggaggacc gcacagtaa                             759
```

<210> SEQ ID NO 38
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 38

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Cys Gly Ala Tyr Cys Ala Ser Lys
145                 150                 155                 160
```

```
Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Ala Ile Lys
        180                 185                 190

Thr Pro Met Met Asp Asp Tyr Glu Gly Ala Glu Glu Met Tyr Ser Gln
    195                 200                 205

Arg Thr Ser Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 39
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 39

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa aagcgttgaa     300
gacactacca cggaggaatg gcgtaaactg ctgtccgtta atctggatgg tgttttttc     360
ggcacccgtc tgggcattca gcgcatgaaa aataaaggct gggcgctag catcatcaat     420
atgagcagtg tgtggggat tgtaggctgg ccgactacag gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagatgacg gagacccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 40
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 40

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60
```

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Met Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 41
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 41
atgaccgatc gtctgaaggg caaagtagcc atcgtaaccg cgggacacaa aggtatcggt        60
ttggcaatcg ccgataaatt tgtagaggag ggtgcgaaag tagttattac tggtcgtcgt       120
gcggatgtag gtgaaaaggc cgccaaatca atcgcggca ctgatgttat tcgctttgtc        180
cagcacgatg tatccgatga agcaggctgg cctaaactgt tcgacaccac cgaggaggca       240
ttcggcccgg ttacgaccgt agtgaacaat gcaggattat ggtggttaa aagcgttgaa        300 gacactacca cggaggaatg gcgtaaactg ctgtccgtta atctggatgg tgtttttttc       360
ggcacccgtc tgggcattca gcgcatgaaa aataaaggct gggcgctag catcatcaat        420 atgagcagtg tgtgggggat tgtaggctgg ccgactacag gggcatactg tgcttccaag       480
ggggcggtac gtatcatgtc gaaaagcgca gcgctggatt gcgcactgaa ggactacgat       540
gtgcgtgtca acacagtaca tccgggcccg atcaagaccc cgatgatgga tgatgaagaa       600
ggtgctgagg aaatgttttc acagcgtacg gagaccccta tgggtcacat tggcgaaccg       660
aatgacatcg catgggtctg tgtgtacctg gcatctgacg aatcgaaatt tgcgacgggt       720
gcagaatttg tggtcgacgg cgggaggacc gcacagtaa                              759

<210> SEQ ID NO 42
<211> LENGTH: 252
<212> TYPE: PRT
<213> ORGANISM: Artificial Sequence

```
<220> FEATURE:
<223> OTHER INFORMATION: Aldo-keto reductase variant from Lactobacillus
      kefiri

<400> SEQUENCE: 42

Met Thr Asp Arg Leu Lys Gly Lys Val Ala Ile Val Thr Gly Thr
1               5                   10                  15

Gln Gly Ile Gly Leu Ala Ile Ala Asp Lys Phe Val Glu Glu Gly Ala
            20                  25                  30

Lys Val Ile Thr Gly Arg Arg Ala Asp Val Gly Lys Ala Ala
            35                  40                  45

Lys Ser Ile Gly Gly Thr Asp Val Ile Arg Phe Val Gln His Asp Val
50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Met Val Val
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
            195                 200                 205

Arg Thr Glu Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 43
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 43
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa agcgttgaa     300 gacactacca cggaggaatg gcgtaaactg ctgtccgtta atctggatgg tgttttttc    360 ggcacccgtc tgggcattca gcgcatgaaa aataaaggct tgggcgctag catcatcaat    420
```

```
atgagcagtg tgtgggggat gtaggctgg ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagcgtacg gaggaaccta tgggtcacat ggcgaaccg    660 aatgacatcg catgggtctg tgtgtacctg gcatctgacg aatcgaaatt tgcgacgggt    720
gcagaatttg tggtcgacgg cgggaggacc gcacagtaa                           759
```

\<210\> SEQ ID NO 44
\<211\> LENGTH: 252
\<212\> TYPE: PRT
\<213\> ORGANISM: Artificial Sequence
\<220\> FEATURE:
\<223\> OTHER INFORMATION: Aldo-keto reductase variant from Lactobacillus kefiri

\<400\> SEQUENCE: 44

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Glu Glu Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

\<210\> SEQ ID NO 45
\<211\> LENGTH: 759
\<212\> TYPE: DNA
\<213\> ORGANISM: Artificial Sequence

```
<220> FEATURE:
<223> OTHER INFORMATION: Aldo-keto reductase variant from Lactobacillus
      kefiri

<400> SEQUENCE: 45
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattc cggtggttaa aagcgttgaa      300
gacactacca cggaggaatg gcgtaaactg ctgtccgtta atctggatgg tgttttttc     360 ggcacccgtc tgggcattca gcgcatgaaa aataaaggct gggcgctag catcatcaat      420 atgagcagtg tgtggggat gtaggctgg ccgactacag gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
aatgctgagg aaatgttttc acagcgtacg gagggtccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 46
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 46

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190
```

Thr Pro Met Met Asp Asp Tyr Glu Asn Ala Glu Glu Met Phe Ser Gln
        195                 200                 205

Arg Thr Glu Gly Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 47
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 47
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattc cggtggtaa aagcgttgaa     300 gacactacca cggaggaatg gcgtaaactg ctgtccgtta tctggatgg tgtttttttc     360 ggcacccgtc tgggcattca gcgcatgaaa ataaaggct tgggcgctag catcatcaat     420
atgagcagtg tgtggggat gtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagcgtacg gagcatccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                           759

<210> SEQ ID NO 48
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 48

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

```
Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
            195                 200                 205

Arg Thr Glu His Pro Met Gly His Ile Gly Glu Pro Asn Asp Ile Ala
            210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 49
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 49

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa     300 gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgtgggggat tgtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggccaa atcaagaccc cgatgatgga tgattatgaa     600
ggtgctgagg aaatgttttc acagcgtacg gagaccccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 50
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 50

| | | | | | | | | | | | | | | |
|---|---|---|---|---|---|---|---|---|---|---|---|---|---|---|
| Met | Thr | Asp | Arg | Leu | Lys | Gly | Lys | Val | Ala | Ile | Val | Thr | Gly | Thr |
| 1 | | | | 5 | | | | | 10 | | | | | 15 |
| Gln | Gly | Ile | Gly | Leu | Ala | Ile | Ala | Asp | Lys | Phe | Val | Glu | Glu | Gly |
| | | | 20 | | | | | 25 | | | | | 30 | |
| Lys | Val | Val | Ile | Thr | Gly | Arg | Arg | Ala | Asp | Val | Gly | Glu | Lys | Ala |
| | | | | 35 | | | | | 40 | | | | | 45 |
| Lys | Ser | Ile | Gly | Gly | Thr | Asp | Val | Ile | Arg | Phe | Val | Gln | His | Asp |
| | | | 50 | | | | | 55 | | | | | 60 | |

Ala Lys Ser Ile Gly Gly Thr Asp Val Ile Arg Phe Val Gln His Asp Val
    50              55                  60

Ser Asp Glu Ala Gly Trp Pro Lys Leu Phe Asp Thr Thr Glu Glu Ala
65              70                  75                  80

Phe Gly Pro Val Thr Thr Val Asn Asn Ala Gly Ile Pro Val Val
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Gln Ile Lys
                180                 185                 190

Thr Pro Met Met Asp Asp Tyr Glu Gly Ala Glu Glu Met Phe Ser Gln
                195                 200                 205

Arg Thr Glu Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 51
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 51

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattcc cggtggttaa aagcgttgaa     300
gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagtg tgtgggggat tgtaggctgg ccgactcatg gggcatactg tgcttccaag     480
ggggcggtac gtatcatgtc gaaaagcgca gcgctggatt gcacactgaa ggactacgat     540
```

```
gtgcgtgtca acacagtaca tccgggcccg atcaagaccc cgatgatgga tgattatgaa    600
ggtgctgagg aaatgttttc acagcgtacg gagacccta tgggtcacat tggcgaaccg     660
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 52
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 52

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr His Gly Ala Tyr Cys Ala Ser Lys
145                 150                 155                 160

Gly Ala Val Arg Ile Met Ser Lys Ser Ala Ala Leu Asp Cys Thr Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 53
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 53

```
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcagggattc cggtggtaa aagcgttgaa        300 gacactacca cggaggaatg gcgtaaactg ctgtccgtta atctggatgg tgttttttc        360 ggcacccgtc tgggcattca gcgcatgaaa aataaaggct gggcgctag catcatcaat       420 atgagcagtg tgtgggggat gtaggctgg ccgacttgcg gggcatactg tgcttccaag        480
ggggcggtac gtatcatgtc gaaaagcgca gcgctggatt gcgcactgaa ggactacgat       540
gtgcgtgtca acacagtaca tccgggcccg atcaagaccc cgatgatgga tgattatgaa       600
ggtgctgagg aaatgttttc acagcgtacg gagcgtccta tgggtcacat ggcgaaccg        660 aatgacatcg catgggtctg tgtgtacctg gcatctgacg aatcgaaatt tgcgacgggt       720
gcagaatttg tggtcgacgg cgggaggacc gcacagtaa                              759
```

<210> SEQ ID NO 54
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 54

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205
```

```
Arg Thr Glu Arg Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 55
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 55
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagtg tgtggggat gtaggctgg ccgacttgcg gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagattacg gagaccccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 56
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 56

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110
```

-continued

```
Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
        130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Ile Thr Glu Thr Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 57
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 57

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt cgacaccac cgaggaggca    240
ttcggcccgg ttacgaccgt agtgaacaat gcagggattc cggtggtaa aagcgttgaa    300
gacactacca cggaggaatg gcgtaaactg ctgtccgtta atctggatgg tgttttttc    360
ggcacccgtc tgggcattca gcgcatgaaa aataaaggct ggggcgctag catcatcaat    420
atgagcagtg tgtgggggat gtaggctgg ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagtttacg gagaccccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                            759
```

<210> SEQ ID NO 58
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 58

```
Met Thr Asp Arg Leu Lys Gly Lys Val Ala Ile Val Thr Gly Gly Thr
1               5                   10                  15
```

```
Gln Gly Ile Gly Leu Ala Ile Ala Asp Lys Phe Val Glu Glu Gly Ala
         20                  25                  30

Lys Val Val Ile Thr Gly Arg Arg Ala Asp Val Gly Glu Lys Ala Ala
     35                  40                  45

Lys Ser Ile Gly Gly Thr Asp Val Ile Arg Phe Val Gln His Asp Val
 50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
             85                  90                  95

Lys Ser Val Glu Asp Thr Thr Thr Glu Glu Trp Arg Lys Leu Leu Ser
        100                 105                 110

Val Asn Leu Asp Gly Val Phe Phe Gly Thr Arg Leu Gly Ile Gln Arg
    115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Phe Thr Glu Thr Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 59
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 59
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcagggattc cggtggttaa aagcgttgaa   300
gacactacca cggaggaatg gcgtaaactg ctgtccgtta atctggatgg tgttttttc    360 ggcacccgtc tgggcattca gcgcatgaaa aataaaggct gggcgctag catcatcaat   420 atgagcagtg tgtggggat tgtaggctgg ccgacttgcg gggcatactg tgcttccaag   480
ggggcggtac gtatcatgtc gaaaagcgca gcgctggatt gcgcactgaa ggactacgat   540
gtgcgtgtca acacagtaca tccgggcccg atcaagaccc cgatgatgga tgattatgaa   600
ggtgctgagg aaatgttttc acagcgtacg gagaccatga tgggtcacat tggcgaaccg   660
```

-continued

```
aatgacatcg catgggtctg tgtgtacctg gcatctgacg aatcgaaatt tgcgacgggt      720
gcagaatttg tggtcgacgg cgggaggacc gcacagtaa                             759
```

<210> SEQ ID NO 60
<211> LENGTH: 252
<212> TYPE: PRT
<213> ORGANISM: Artificial Sequence
<220> FEATURE:
<223> OTHER INFORMATION: Aldo-keto reductase variant from Lactobacillus
    kefiri

<400> SEQUENCE: 60

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Glu Thr Met Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 61
<211> LENGTH: 759
<212> TYPE: DNA
<213> ORGANISM: Artificial Sequence
<220> FEATURE:
<223> OTHER INFORMATION: Aldo-keto reductase variant from Lactobacillus
    kefiri

<400> SEQUENCE: 61

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
```

-continued

```
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa aagcgttgaa    300
gacactacca cggaggaatg gcgtaaactg ctgtccgtta atctggatgg tgttttttc     360 ggcacccgtc tgggcattca gcgcatgaaa aataaaggct gggcgctag catcatcaat    420 atgagcagtg tgtgggggat tgtaggctgg ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagcgtacg gagaccgata tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 62
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 62

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Glu Thr Asp Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Arg Thr Ala Gln
            245                 250

<210> SEQ ID NO 63
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 63

```
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcaggattc cggtggttaa aagcgttgaa    300
gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg tgtgggggat gtaggctgg ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acaggaaacg gagacccta tgggtcacat ggcgaaccg    660 aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 64
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 64

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
            195                 200                 205

Glu Thr Glu Thr Pro Met Gly His Ile Gly Glu Pro Asn Asp Ile Ala
            210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 65
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 65
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt cgacaccac cgaggaggca    240 ttcggcccgg ttacgaccgt agtgaacaat gcagggattc cggtggttaa agcgttgaa    300 gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg tgtggggat tgtaggctgg ccgactacag gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtcatgagg aaatgttttc acagcgtacg gagaccccta tgggtcacat ggcgaaccg    660 aatgacatcg catgggtctg tgtgtacctg gcatctgacg aatcgaaatt tgcgacgggt    720
gcagaatttg tggtcgacgg cgggaggacc gcacagtaa                          759

<210> SEQ ID NO 66
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 66

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
 50                  55                  60

Ser Asp Glu Ala Gly Trp Pro Lys Leu Phe Asp Thr Thr Glu Glu Ala
 65                  70                  75                  80

Phe Gly Pro Val Thr Thr Val Val Asn Asn Ala Gly Ile Pro Val Val
                 85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp Tyr Glu Gly His Glu Glu Met Phe Ser Gln
                195                 200                 205

Arg Thr Glu Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 67
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 67
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa aagcgttgaa     300
gacactacca cggaggaatg gcgtaaactg ctgtccgtta atctggatgg tgtttttttc     360
ggcacccgtc tgggcattca gcgcatgaaa aataaaggct gggcgctag catcatcaat     420 atgagcagtg tgtggggat tgtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagtggacg gagaccccta tgggtcacat ggcgaaccg     660 aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 68

<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 68

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Trp Pro Thr Cys Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Tyr Glu Gly Ala Glu Met Phe Ser Gln
        195                 200                 205
Trp Thr Glu Thr Pro Met Gly His Ile Gly Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250
```

<210> SEQ ID NO 69
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 69

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300 gacactacca cggaggaatg gcgtaaactg ctgtccgtta atctggatgg tgttttttc      360
```

```
ggcacccgtc tgggcattca gcgcatgaaa aataaaggct tgggcgctag catcatcaat    420
atgagcagtg tgtggggat tgtaggctgg ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagcgtacg gagacccgta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 70
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 70

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Glu Thr Arg Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 71
<211> LENGTH: 759
<212> TYPE: DNA
<213> ORGANISM: Artificial Sequence

```
<220> FEATURE:
<223> OTHER INFORMATION: Aldo-keto reductase variant from Lactobacillus
      kefiri

<400> SEQUENCE: 71
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa aagcgttgaa    300
gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg tgtggggat gtaggctgg ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagcgtacg gagaccaaaa tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                           759

<210> SEQ ID NO 72
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 72

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190
```

```
Thr Pro Met Met Asp Asp Tyr Glu Gly Ala Glu Met Phe Ser Gln
        195                 200                 205

Arg Thr Glu Thr Lys Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 73
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 73
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattcc ggtggttaa aagcgttgaa      300 gacactacca cggaggaatg gcgtaaactg ctgtccgtta atctggatgg tgttttttc      360 ggcacccgtc tgggcattca gcgcatgaaa ataaaggct tgggcgctag catcatcaat     420
atgagcagtg tgtggggat tgtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagcgtacg gagaccgaaa tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 74
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 74

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95
```

```
Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
            195                 200                 205

Arg Thr Glu Thr Glu Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 75
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 75
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa     300 gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgtggggat tgtaggctgg ccgactacag gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgtttga tcagcgtacg gagaccccta tggtcacat ggcgaaccg      660 aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 76
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri
```

<400> SEQUENCE: 76

| | | | | | | | | | | | | | | | |
|---|---|---|---|---|---|---|---|---|---|---|---|---|---|---|---|
|Met|Thr|Asp|Arg|Leu|Lys|Gly|Lys|Val|Ala|Ile|Val|Thr|Gly|Gly|Thr|
|1| | | |5| | | | |10| | | | |15| |
|Gln|Gly|Ile|Gly|Leu|Ala|Ile|Ala|Asp|Lys|Phe|Val|Glu|Glu|Gly|Ala|
| | | |20| | | | |25| | | | |30| | |
|Lys|Val|Val|Ile|Thr|Gly|Arg|Arg|Ala|Asp|Val|Gly|Glu|Lys|Ala|Ala|
| | |35| | | | |40| | | | |45| | | |
|Lys|Ser|Ile|Gly|Gly|Thr|Asp|Val|Ile|Arg|Phe|Val|Gln|His|Asp|Val|
| |50| | | | |55| | | | |60| | | | |
|Ser|Asp|Glu|Ala|Gly|Trp|Pro|Lys|Leu|Phe|Asp|Thr|Thr|Glu|Glu|Ala|
|65| | | | |70| | | | |75| | | | |80|
|Phe|Gly|Pro|Val|Thr|Thr|Val|Asn|Asn|Ala|Gly|Ile|Pro|Val|Val|
| | | | |85| | | | |90| | | | |95| |
|Lys|Ser|Val|Glu|Asp|Thr|Thr|Glu|Glu|Trp|Arg|Lys|Leu|Leu|Ser|
| | | |100| | | | |105| | | | |110| | |
|Val|Asn|Leu|Asp|Gly|Val|Phe|Phe|Gly|Thr|Arg|Leu|Gly|Ile|Gln|Arg|
| | |115| | | | |120| | | | |125| | | |
|Met|Lys|Asn|Lys|Gly|Leu|Gly|Ala|Ser|Ile|Ile|Asn|Met|Ser|Ser|Val|
| |130| | | | |135| | | | |140| | | | |
|Trp|Gly|Ile|Val|Gly|Trp|Pro|Thr|Thr|Gly|Ala|Tyr|Cys|Ala|Ser|Lys|
|145| | | | |150| | | | |155| | | | |160|
|Gly|Ala|Val|Arg|Ile|Met|Ser|Lys|Ser|Ala|Ala|Leu|Asp|Cys|Ala|Leu|
| | | | |165| | | | |170| | | | |175| |
|Lys|Asp|Tyr|Asp|Val|Arg|Val|Asn|Thr|Val|His|Pro|Gly|Pro|Ile|Lys|
| | | |180| | | | |185| | | | |190| | |
|Thr|Pro|Met|Met|Asp|Asp|Tyr|Glu|Gly|Ala|Glu|Glu|Met|Phe|Asp|Gln|
| | |195| | | | |200| | | | |205| | | |
|Arg|Thr|Glu|Thr|Pro|Met|Gly|His|Ile|Gly|Glu|Pro|Asn|Asp|Ile|Ala|
| |210| | | | |215| | | | |220| | | | |
|Trp|Val|Cys|Val|Tyr|Leu|Ala|Ser|Asp|Glu|Ser|Lys|Phe|Ala|Thr|Gly|
|225| | | | |230| | | | |235| | | | |240|
|Ala|Glu|Phe|Val|Val|Asp|Gly|Gly|Arg|Thr|Ala|Gln|
| | | | |245| | | | |250| | | | | | |

<210> SEQ ID NO 77
<211> LENGTH: 759
<212> TYPE: DNA
<213> ORGANISM: Artificial Sequence
<220> FEATURE:
<223> OTHER INFORMATION: Aldo-keto reductase variant from Lactobacillus
   kefiri

<400> SEQUENCE: 77

| | |
|---|---|
|atgaccgatc gtctgaaggg caaagtagcc atcgtaaccg gcgggacaca aggtatcggt|60|
|ttggcaatcg ccgataaatt tgtagaggag ggtgcgaaag tagttattac tggtcgtcgt|120|
|gcggatgtag gtgaaaaggc cgccaaatca atcggcggca ctgatgttat tcgctttgtc|180|
|cagcacgatg tatccgatga agcaggctgg cctaaactgt tcgacaccac cgaggaggca|240|
|ttcggcccgg ttacgaccgt agtgaacaat gcaggattcc cggtggttaa aagcgttgaa|300|
|gacactacca cggaggaatg gcgtaaactg ctgtccgtta atctggatgg tgttttttc|360|
|ggcacccgtc tgggcattca gcgcatgaaa aataaaggct gggcgctag catcatcaat|420|
|atgagcagtg tgtggggat gtaggctgg ccgacttgcg gggcatactg tgcttccaag|480|
|ggggcggtac gtatcatgtc gaaaagcgca gcgctggatt gcgcactgaa ggactacgat|540|

```
gtgcgtgtca acacagtaca tccgggcccg atcaagaccc cgatgatgga tgattatgaa    600
ggtcatgagg aaatgttttc acagcgtacg gagacccctc tgggtcacat ggcgaaccg    660 aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 78
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 78

```
Met Thr Asp Arg Leu Lys Gly Lys Val Ala Ile Val Thr Gly Gly Thr
 1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly His Glu Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 79
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 79

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgtgggggat gtaggctgg ccgacttgcg gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagcgtacg gagaccacaa tgggtcacat ggcgaaccg      660
aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 80
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 80

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205
```

```
Arg Thr Glu Thr Thr Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250
```

<210> SEQ ID NO 81
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 81

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcagggattc cggtggttaa agcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagtg tgtgggggat gtaggctggc ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagacaacg gagaccccta tgggtcacat ggcgaaccg    660
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 82
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 82

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
```

```
Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp Tyr Glu Gly Ala Glu Glu Met Phe Ser Gln
            195                 200                 205

Thr Thr Glu Thr Pro Met Gly His Ile Gly Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 83
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 83
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt cgacaccac cgaggaggca   240 ttcggcccgg ttacgaccgt agtgaacaat gcagggattc aagtggttaa aagcgttgaa   300
gacactacca cggaggaatg gcgtaaactg ctgtccgtta tctggatgg tgttttttc   360 ggcacccgtc tgggcattca gcgcatgaaa aataaaggct gggcgctag catcatcaat   420 atgagcagtg tgtgggggat gtaggctgg ccgacttgcg gggcatactg tgcttccaag   480
ggggcggtac gtatcatgtc gaaaagcgca gcgctggatt gcgcactgaa ggactacgat   540
gtgcgtgtca acacagtaca tccgggcccg atcaagaccc cgatgatgga tgattatgaa   600
ggtgctgagg aaatgttttc acagcgtacg agacccccta tgggtcacat tggcgaaccg   660
aatgacatcg catgggtctg tgtgtacctg gcatctgacg aatcgaaatt tgcgacgggt   720
gcagaatttg tggtcgacgg cgggaggacc gcacagtaa                         759

<210> SEQ ID NO 84
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 84

Met Thr Asp Arg Leu Lys Gly Lys Val Ala Ile Val Thr Gly Gly Thr
1               5                   10                  15
```

Gln Gly Ile Gly Leu Ala Ile Ala Asp Lys Phe Val Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Gln Val Val
                    85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                    165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Glu Thr Pro Met Gly His Ile Gly Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                    245                 250

<210> SEQ ID NO 85
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 85
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcagggattc aggtggttaa aagcgttgaa   300
gacactacca cggaggaatg gcgtaaactg ctgtccgtta atctggatgg tgttttttc    360 ggcacccgtc tgggcattca gcgcatgaaa aataaaggct gggcgctag catcatcaat   420 atgagcagtg tgtggggat gtaggctgg ccgacttgcg ggcatactg tgcttccaag    480 ggggcggtac gtatcatgtc gaaaagcgca gcgctggatt gcgcactgaa ggactacgat   540
gtgcgtgtca acacagtaca tccgggcccg atcaagaccc cgatgatgga tgattatgaa   600
ggttttgagg aaatgttttc acagcgtacg agacccccta tgggtcacat tggcgaaccg   660

```
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 86
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 86

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Phe Glu Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 87
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 87

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
```

```
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa agcgttgaa     300 gacactacca cggaggaatg gcgtaaactg ctgtccgtta atctggatgg tgttttttc     360 ggcacccgtc tgggcattca gcgcatgaaa aataaaggct gggcgctag  catcatcaat    420 atgagcagtg tgtggggat tgtaggctgg ccgactacag gggcatactg tgcttccaag     480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagcgtacg gagacccata tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 88
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 88

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Glu Thr His Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Arg Thr Ala Gln
                245                 250

<210> SEQ ID NO 89
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 89

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattc cggtggttaa aagcgttgaa     300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgtggggat gtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acaggttacg gagaccccta tgggtcacat ggcgaaccg     660 aatgacatcg catgggtctg tgtgtacctg gcatctgacg aatcgaaatt tgcgacgggt     720
gcagaatttg tggtcgacgg cgggaggacc gcacagtaa                             759
```

<210> SEQ ID NO 90
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 90

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Pro Ile Lys
        180                 185                 190

Thr Pro Met Met Asp Asp Tyr Glu Gly Ala Glu Met Phe Ser Gln
    195                 200                 205

Val Thr Glu Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
            245                 250

<210> SEQ ID NO 91
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 91

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa agcgttgaa     300 gacactacca cggaggaatg gcgtaaactg ctgtccgtta atctggatgg tgttttttc     360 ggcacccgtc tgggcattca gcgcatgaaa aataaaggct tgggcgctag catcatcaat    420
atgagcagtg tgtgggggat tgtaggctgg ccgactacag gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggttatgagg aaatgttttc acagcgtacg gagaccccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 92
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 92

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

```
Lys Ser Ile Gly Gly Thr Asp Val Ile Arg Phe Val Gln His Asp Val
 50                  55                  60

Ser Asp Glu Ala Gly Trp Pro Lys Leu Phe Asp Thr Thr Glu Glu Ala
 65                  70                  75                  80

Phe Gly Pro Val Thr Thr Val Val Asn Asn Ala Gly Ile Pro Val Val
                 85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp Tyr Glu Gly Tyr Glu Glu Met Phe Ser Gln
                195                 200                 205

Arg Thr Glu Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 93
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 93

```
atgaccgatc gtctgaaggg caaagtagcc atcgtaaccg cgggacacaa aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300
gacactacca cggaggaatg cgtaaactg ctgtccgtta atctggatgg tgttttttc       360
ggcacccgtc tgggcattca gcgcatgaaa aataaaggct gggcgctag catcatcaat      420
atgagcagtg tgtggggat tgtaggctgg ccgactacag gcatactg tgcttccaag        480
ggggcggtac gtatcatgtc gaaaagcgca gcgctggatt gcgcactgaa ggactacgat     540
gtgcgtgtca acacagtaca tccgggcccg atcaagaccc cgatgaatga tgattatgaa     600
ggtgctgagg aaatgttttc acagcgtacg gagacccta tggtcacat ggcgaaccg        660
aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 94

<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 94

```
Met Thr Asp Arg Leu Lys Gly Lys Val Ala Ile Val Thr Gly Gly Thr
1               5                  10                   15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Trp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Asn Asp Asp Tyr Glu Gly Ala Glu Met Phe Ser Gln
        195                 200                 205
Arg Thr Glu Thr Pro Met Gly His Ile Gly Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250
```

<210> SEQ ID NO 95
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 95

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattcc ggtggttaa aagcgttgaa      300 gacactacca cggaggaatg gcgtaaactg ctgtccgtta atctggatgg tgttttttc      360
```

```
ggcacccgtc tgggcattca gcgcatgaaa aataaaggct tgggcgctag catcatcaat    420
atgagcagtg tgtgggggat tgtaggctgg ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagcgtacg gagaccaata tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 96
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri
<400> SEQUENCE: 96

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Glu Thr Asn Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 97
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 97

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcaggattc cggtggttaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagtg tgtggggat gtaggctgg ccgacttgcg gggcatactg tgcttccaag   480
ggggcggtac gtatcatgtc gaaaagcgca gcgctggatt gcgcactgaa ggactacgat   540
gtgcgtgtca acacagtaca tccgggcccg atcaagaccc cgatgatgga tgattatgaa   600
ggtgctgagg aaatgttttc acagcgtacg ccaaccccta tgggtcacat ggcgaaccg    660
aatgacatcg catgggtctg tgtgtacctg gcatctgacg aatcgaaatt tgcgacgggt   720
gcagaatttg tggtcgacgg cgggaggacc gcacagtaa                          759
```

<210> SEQ ID NO 98
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 98

```
Met Thr Asp Arg Leu Lys Gly Lys Val Ala Ile Val Thr Gly Gly Thr
1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190
```

```
Thr Pro Met Met Asp Asp Tyr Glu Gly Ala Glu Met Phe Ser Gln
        195                 200                 205

Arg Thr Pro Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 99
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 99
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattcc ggtggttaa aagcgttgaa      300 gacactacca cggaggaatg gcgtaaactg ctgtccgtta atctggatgg tgttttttc      360 ggcacccgtc tgggcattca gcgcatgaaa ataaaggct tgggcgctag catcatcaat      420
atgagcagtg tgtggggat tgtaggctgg ccgacttgcg gggcatactg tgcttccaag      480
ggggcggtac gtatcatgtc gaaaagcgca gcgctggatt gcgcactgaa ggactacgat      540
gtgcgtgtca acacagtaca tccgggcccg atcaagaccc cgatgatgga tgattatgaa      600
ggtgctgagg aaatgtttga tcagcgtacg gagacccta tgggtcacat tggcgaaccg      660
aatgacatcg catgggtctg tgtgtacctg gcatctgacg aatcgaaatt tgcgacgggt      720
gcagaatttg tggtcgacgg cgggaggacc gcacagtaa                            759

<210> SEQ ID NO 100
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 100

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95
```

```
Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Asp Gln
            195                 200                 205

Arg Thr Glu Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 101
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 101

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa aagcgttgaa     300
gacactacca cggaggaatg gcgtaaactg ctgtccgtta atctggatgg tgttttcttc     360
ggcacccgtc tgggcattca gcgcatgaaa aataaaggct gggcgctag catcatcaat     420 atgagcagtg tgtgggggat tgtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagcgtacg gagaccggta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 102
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 102

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Pro Val Val
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Glu Thr Gly Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 103
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 103
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattc cggtggttaa aagcgttgaa      300
gacactacca cggaggaatg gcgtaaactg ctgtccgtta atctggatgg tgtttttttc     360
ggcacccgtc tgggcattca gcgcatgaaa aataaaggct gggcgctag catcatcaat     420 atgagcagtg tgtggggat tgtaggctgg ccgactcatg gggcatactg tgcttccaag     480
ggggcggtac gtatcatgtc gaaaagcgca gcgctggatt gcgcactgaa ggactacgat     540

```
gtgcgtgtca acacagtaca tccgggcccg atcaagaccc cgatgatgga tgattatgaa    600
ggtgctgagg aaatgttttc acagcgtacg gagacccta tgggtcacat tggcgaaccg     660
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 104
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 104

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr His Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
    195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 105
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 105

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgtgggggat gtaggctgg ccgacttgcg gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggttatgagg aaatgttttc acagcgtacg gagacccta tgggtcacat ggcgaaccg       660
aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 106
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 106

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Trp Pro Thr Cys Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Tyr Glu Gly Tyr Glu Glu Met Phe Ser Gln
            195                 200                 205
```

```
Arg Thr Glu Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250

<210> SEQ ID NO 107
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 107
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag  catcatcaat     420 atgagcagtg tgtgggggat gtaggctgg ccgacttgcg gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagggtacg gagacccccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                             759

<210> SEQ ID NO 108
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 108

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110
```

```
Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Gly Thr Glu Thr Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 109
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 109
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattc cggtggttaa aagcgttgaa     300
gacactacca cggaggaatg gcgtaaactg ctgtccgtta atctggatgg tgtttttttc     360
ggcacccgtc tgggcattca gcgcatgaaa aataaaggct gggcgctag catcatcaat     420 atgagcagtg tgtgggggat gtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagcgtttg gagaccccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                           759

<210> SEQ ID NO 110
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 110

Met Thr Asp Arg Leu Lys Gly Lys Val Ala Ile Val Thr Gly Gly Thr
1               5                   10                  15
```

```
Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Leu Glu Thr Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 111
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 111
atgaccgatc gtctgaaggg caaagtagcc atcgtaaccg cgggacacaa aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa agcgttgaa    300 gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg tgtgggggat gtaggctgg ccgactacag gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgtttgg tcagcgtacg agacccccta tgggtcacat tggcgaaccg    660
```

```
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 112
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 112

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Gly Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 113
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 113

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt    120
```

-continued

```
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa aagcgttgaa    300
gacactacca cggaggaatg gcgtaaactg ctgtccgtta atctggatgg tgttttttc     360 ggcacccgtc tgggcattca gcgcatgaaa aataaaggct gggcgctag catcatcaat    420 atgagcagtg tgtgggggat tgtaggctgg ccgactacag gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctttgg aaatgttttc acagcgtacg gagacccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 114
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 114

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Trp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Tyr Glu Gly Ala Leu Glu Met Phe Ser Gln
        195                 200                 205
Arg Thr Glu Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
```

Ala Glu Phe Val Val Asp Gly Gly Arg Thr Ala Gln
            245                 250

<210> SEQ ID NO 115
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 115

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat cgctttgtc    180 cagcacgatg tatccgatga agcaggctgg cctaaactgt tcgacaccac cgaggaggca   240
ttcggcccgg ttacgaccgt agtgaacaat gcaggattc cggtggttaa aagcgttgaa    300
gacactacca cggaggaatg gcgtaaactg ctgtccgtta atctggatgg tgtttttttc    360
ggcacccgtc tgggcattca gcgcatgaaa aataaaggct gggcgctag catcatcaat    420 atgagcagtg tgtgggggat gtaggctgg ccgactacag gggcatactg tgcttccaag    480
ggggcggtac gtatcatgtc gaaaagcgca gcgctggatt gcgcactgaa ggactacgat   540
gtgcgtgtca acacagtaca tccgggcccg atcaagaccc cgatgatgga tgattatgaa   600
ggtgctgagg aaatgttttc acagcgtcca gagacccta tgggtcacat ggcgaaccg    660 aatgacatcg catgggtctg tgtgtacctg gcatctgacg aatcgaaatt tgcgacgggt   720
gcagaatttg tggtcgacgg cgggaggacc gcacagtaa                          759
```

<210> SEQ ID NO 116
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 116

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

```
Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Pro Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 117
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 117

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagtg tgtggggat tgtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgttttc acagcgtacg gagggtccta tgggtcacat ggcgaaccg     660 aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 118
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 118

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45
```

Lys Ser Ile Gly Gly Thr Asp Val Ile Arg Phe Val Gln His Asp Val
50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp Tyr Glu Gly Ala Glu Met Phe Ser Gln
                195                 200                 205

Arg Thr Glu Gly Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 119
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 119
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagtg tgtggggat tgtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgaaaga tgattatgaa     600
ggtgctgagg aaatgttttc acagcgtacg gagaccccta tgggtcacat ggcgaaccg     660 aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 120

<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 120

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Trp Pro Thr Cys Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Lys Asp Asp Tyr Glu Gly Ala Glu Met Phe Ser Gln
        195                 200                 205
Arg Thr Glu Thr Pro Met Gly His Ile Gly Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250
```

<210> SEQ ID NO 121
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 121

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattc cggtggttaa aagcgttgaa      300
gacactacca cggaggaatg gcgtaaactg ctgtccgtta atctggatgg tgttttttc      360
```

```
ggcacccgtc tgggcattca gcgcatgaaa aataaaggct tgggcgctag catcatcaat    420
atgagcagtg tgtggggggat tgtaggctgg ccgacttgcg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgctgagg aaatgttttc acagcgtacg gagacccccta tgggtcacaa tggcgaaccg    660
aatgacatcg catgggtctg tgtgtacctg gcatctgacg aatcgaaatt tgcgacgggt    720
gcagaatttg tggtcgacgg cgggaggacc gcacagtaa                            759
```

```
<210> SEQ ID NO 122
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 122
```

| | | | | | | | | | | | | | | |
|---|---|---|---|---|---|---|---|---|---|---|---|---|---|---|
| Met | Thr | Asp | Arg | Leu | Lys | Gly | Lys | Val | Ala | Ile | Val | Thr | Gly | Gly | Thr |
| 1 | | | | 5 | | | | | 10 | | | | | 15 | |

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Glu Thr Pro Met Gly His Asn Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

```
<210> SEQ ID NO 123
<211> LENGTH: 759
<212> TYPE: DNA
<213> ORGANISM: Artificial Sequence
```

```
<220> FEATURE:
<223> OTHER INFORMATION: Aldo-keto reductase variant from Lactobacillus
      kefiri

<400> SEQUENCE: 123
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcagggattc cggtggttaa aagcgttgaa       300
gacactacca cggaggaatg gcgtaaactg ctgtccgtta atctggatgg tgttttttc        360 ggcacccgtc tgggcattca gcgcatgaaa aataaaggct gggcgctag catcatcaat        420 atgagcagtg tgtgggggct gtaggctgg ccgacttgcg gggcatactg tgcttccaag        480
ggggcggtac gtatcatgtc gaaaagcgca gcgctggatt gcgcactgaa ggactacgat       540
gtgcgtgtca acacagtaca tccgggcccg atcaagaccc cgatgatgga tgattatgaa       600
ggttatgagg aaatgttttc acagcgtacg gagacccta tgggtcacat tggcgaaccg        660
aatgacatcg catgggtctg tgtgtacctg gcatctgacg aatcgaaatt tgcgacgggt       720
gcagaatttg tggtcgacgg cgggaggacc gcacagtaa                              759

<210> SEQ ID NO 124
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 124

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Leu Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190
```

```
Thr Pro Met Met Asp Asp Tyr Glu Gly Tyr Glu Met Phe Ser Gln
            195                 200                 205

Arg Thr Glu Thr Pro Met Gly His Ile Gly Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 125
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 125
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattcc ggtggttaaa agcgttgaa     300 gacactacca cggaggaatg gcgtaaactg ctgtccgtta atctggatgg tgttttttc     360 ggcacccgtc tgggcattca gcgcatgaaa ataaaggct tgggcgctag catcatcaat     420
atgagcagtg tgtggggat tgtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgtttta tcagcgtacg gagaccccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 126
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 126

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95
```

```
Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Tyr Gln
            195                 200                 205

Arg Thr Glu Thr Pro Met Gly His Ile Gly Glu Pro Asn Asp Ile Ala
            210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 127
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 127

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300
gacactacca cggaggaatg gcgtaaactg ctgtccgtta atctggatgg tgttttttc      360
ggcacccgtc tgggcattca gcgcatgaaa aataaaggct tgggcgctag catcatcaat     420
atgagcagtg tgtgggggat tgtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtcgtgagg aaatgtttc acagcgtacg gagacccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 128
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 128

Met Thr Asp Arg Leu Lys Gly Lys Val Ala Ile Val Thr Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Arg Glu Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 129
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 129
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattcc ggtggttaa aagcgttgaa      300 gacactacca cggaggaatg cgtaaactg ctgtccgtta atctggatgg tgttttttc       360 ggcacccgtc tgggcattca gcgcatgaaa aataaaggct gggcgctag catcatcaat     420 atgagcagtg tgtggggat tgtaggctgg ccgacttgcg gggcatactg tgcttccaag     480
ggggcggtac gtatcatgtc gaaaagcgca gcgctggatt gcgcactgaa ggactacgat     540

```
gtgcgtgtca acacagtaca tccgggcccg atcaagaccc cgatgatgga tgattatgaa    600
ggtgctgagg aaatgttttc acagtatacg gagaccccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 130
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 130

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Tyr Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 131
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 131

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgtgggggat gtaggctgg ccgactacag gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgcattc acagcgtacg gagacccta tgggtcacat ggcgaaccg      660
aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 132
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 132

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met His Ser Gln
        195                 200                 205
```

```
Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 133
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 133

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa agcgttgaa      300
gacactacca cggaggaatg gcgtaaactg ctgtccgtta atctggatgg tgttttttc     360
ggcacccgtc tgggcattca gcgcatgaaa aataaaggct gggcgctag catcatcaat     420
atgagcagtg tgtgggggat gtaggctgg ccgacttgcg gggcatactg tgcttccaag     480
ggggcggtac gtatcatgtc gaaaagcgca gcgctggatt gcgcactgaa ggactacgat     540
gtgcgtgtca acacagtaca tccgggcctt atcaagaccc cgatgattga tgattatgaa     600
ggtgctgagg aaatgttttc acagcgtacg gagacccccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 134
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 134

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110
```

```
Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Cys Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Leu Ile Lys
            180                 185                 190

Thr Pro Met Ile Asp Asp Tyr Glu Gly Ala Glu Glu Met Phe Ser Gln
        195                 200                 205

Arg Thr Glu Thr Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 135
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 135
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattct cggtggtaaa agcgttgaa      300 gacactacca cggaggaatg gcgtaaactg ctgtccgtta atctggatgg tgttttttc      360 ggcaccccgtc tgggcattca gcgcatgaaa aataaaggct tgggcgctag catcatcaat    420
atgagcagtg tgtgggggat tgtaggctgg ccgactacag gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgattatgaa     600
ggtgctgagg aaatgtggtc acagcgtacg gagacccta tgggtcacat tggcgaaccg      660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 136
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 136

Met Thr Asp Arg Leu Lys Gly Lys Val Ala Ile Val Thr Gly Gly Thr
1               5                   10                  15
```

```
Gln Gly Ile Gly Leu Ala Ile Ala Asp Lys Phe Val Glu Gly Ala
             20                  25                  30

Lys Val Val Ile Thr Gly Arg Arg Ala Asp Val Gly Glu Lys Ala Ala
         35                  40                  45

Lys Ser Ile Gly Gly Thr Asp Val Ile Arg Phe Val Gln His Asp Val
     50                  55                  60

Ser Asp Glu Ala Gly Trp Pro Lys Leu Phe Asp Thr Thr Glu Glu Ala
 65                  70                  75                  80

Phe Gly Pro Val Thr Thr Val Val Asn Asn Ala Gly Ile Pro Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Trp Ser Gln
        195                 200                 205

Arg Thr Glu Thr Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 137
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 137
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcagggattc cggtggttaa agcgttgaa     300 gacactacca cggaggaatg gcgtaaactg ctgtccgtta atctggatgg tgttttttc     360 ggcacccgtc tgggcattca gcgcatgaaa aataaaggct gggcgctag catcatcaat    420 atgagcagtg tgtgggggat gtaggctgg ccgactacag gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgattatgaa    600
ggtgcttggg aaatgttttc acagcgtacg gagacccccta tgggtcacat tggcgaaccg    660
```

```
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 138
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 138

```
Met Thr Asp Arg Leu Lys Gly Lys Val Ala Ile Val Thr Gly Gly Thr
1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Trp Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 139
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 139

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
```

```
gcggatgtag gtgaaaaggc cgccaaatca atcggcggca ctgatgttat tcgctttgtc      180
cagcacgatg tatccgatga agcaggctgg cctaaactgt tcgacaccac cgaggaggca      240
ttcggcccgg ttacgaccgt agtgaacaat gcaggggatta tggtggttaa aagcgttgaa      300
gacactacca cggaggaatg gcgtaaactg ctgtccgtta atctggatgg tgttttttc       360 ggcacccgtc tgggcattca gcgcatgaaa aataaaggct tgggcgctag catcatcaat      420
atgagcagtg tgtgggggat tgtaggctgg ccgactacag gggcatactg tgcttccaag      480
ggggcggtac gtatcatgtc gaaaagcgca gcgctggatt gcgcactgaa ggactacgat      540
gtgcgtgtca acacagtaca tccgggcctt atcaagaccc cgatgaatga tgatgaagaa      600
ggtgctgagg aaatgttttc acagcgtacg gagacccta tgggtcacca cggcgaaccg       660
aatgacatcg catgggtctg tgtgtacctg gcatctgacg aatcgaaatt tgcgacgggt      720
gcagaatttg tggtcgacgg cgggaggacc gcacagtaa                              759
```

<210> SEQ ID NO 140
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 140

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Leu Ile Lys
            180                 185                 190

Thr Pro Met Asn Asp Asp Glu Glu Gly Ala Glu Met Phe Ser Gln
        195                 200                 205

Arg Thr Glu Thr Pro Met Gly His His Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Arg Thr Ala Gln
            245                 250

<210> SEQ ID NO 141
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 141

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattag tggtggttaa agcgttgaa     300 gacgacacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgtgggggat gtaggcgat ccgactacag gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gagacccta tgggtcacat ggcgaaccg     660 aatgacatcg catgggtctg tgtgtacctg gcatctgacg aatcgaaatt tgcgacgggt     720
gcagaatttg tggtcgacgg cgggaggacc gcacagtaa                          759
```

<210> SEQ ID NO 142
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 142

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

```
Trp Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 143
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 143

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt cgacaccac cgaggaggca     240
ttcggcccgg ttacgaccgt agtgaacaat gcagggatta tggtggttaa aagcgttgaa     300
gacactacca cggaggaatg gcgtaaactg ctgtccgtta atctggatgg tgttttttc     360
ggcacccgtc tgggcattca gcgcatgaaa aataaaggct tgggcgctag catcatcaat     420
atgagcagtg tgtggggat tgtaggctgg ccgactacag gggcatactg tgcttccaag     480
gggcggtac gtatcatgtc gaaaagcgca gcgctggatt gcgcactgaa ggactacgat     540
gtgcgtgtca acacagtaca tccgggcacg atcaagaccc cgatgatgga tgatgaagaa     600
ggtgctgagg aaatgttttc acagcgtacg gagaatccta tgggtcacat ggcgaaccg     660
aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 144
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 144

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45
```

```
Lys Ser Ile Gly Gly Thr Asp Val Ile Arg Phe Val Gln His Asp Val
 50                  55                  60

Ser Asp Glu Ala Gly Trp Pro Lys Leu Phe Asp Thr Thr Glu Glu Ala
 65                  70                  75                  80

Phe Gly Pro Val Thr Thr Val Val Asn Asn Ala Gly Ile Met Val Val
                 85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Val
                130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Thr Ile Lys
                180                 185                 190

Thr Pro Met Met Asp Asp Glu Glu Gly Ala Glu Met Phe Ser Gln
                195                 200                 205

Arg Thr Glu Asn Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

```
<210> SEQ ID NO 145
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 145
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcagggatta tggtggttaa aagcgttgaa   300
gacactacca cggaggaatg gcgtaaactg ctgtccgtta atctggatgg tgttttttc    360 ggcacccgtc tgggcattca gcgcatgaaa aataaaggct gggcgctag catcatcaat   420 atgagcagtg tgtggggat gtaggctgg ccgactacag gggcatactg tgcttccaag    480
ggggcggtac gtatcatgtc gaaaagcgca gcgctggatt gcgcactgaa ggactacgat   540
gtgcgtgtca acacagtaca tccgggcccg atcaagaccc cgatgatgga tgatgaagaa   600
ggtgctgagg aaatgttttc acagcgtacg gagaatccta tgggtcacat ggcgaaccg    660 aatgacatcg catgggtctg tgtgtacctg gcatctgacg aatcgaaatt tgcgacgggt   720
gcagaatttg tggtcgacgg cgggaggaca gcatggtaa                          759

<210> SEQ ID NO 146
```

<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 146

Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Met Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Trp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Glu Glu Gly Ala Glu Met Phe Ser Gln
        195                 200                 205
Arg Thr Glu Asn Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Trp
                245                 250

<210> SEQ ID NO 147
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 147
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggggatta tggtggttaa agcgttgaa     300 gacactacca cggaggaatg cgtaaactg ctgtccgtta atctggatgg tgttttttc      360

```
ggcacccgtc tgggcattca gcgcatgaaa aataaaggct tgggcgctag catcatcaat    420
atgagcagtg tgtggggat tgtaggctgg ccgactacag gggcatactg tgcttccaag     480
ggggcggtac gtatcatgtc gaaaagcgca gcgctggatt gcgcactgaa ggactacgat    540
gtgcgtgtca acacagtaca tccgggccct atcaagaccc cgatgatgga tgatgaagaa    600
ggtgctgagg aaatgttttc acagggaacg gagacccta tgggtcacat tggcgaaccg     660
aatgacatcg catgggtctg tgtgtacctg gcatctgacg aatcgaaatt tgcgacgggt    720
gcagaatttg tggtcgacgg cgggaggacc gcacagtaa                            759
```

```
<210> SEQ ID NO 148
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 148
```

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Gly Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

```
<210> SEQ ID NO 149
<211> LENGTH: 759
<212> TYPE: DNA
<213> ORGANISM: Artificial Sequence
```

```
<220> FEATURE:
<223> OTHER INFORMATION: Aldo-keto reductase variant from Lactobacillus
      kefiri

<400> SEQUENCE: 149
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcaggdatta tggtggttaa aagcgttgaa       300
gacactacca cggaggaatg gcgtaaagaa ctgtccgtta atctggatgg tgttttttc        360 ggcacccgtc tgggcattca gcgcatgaaa aataaaggct gggcgctag catcatcaat        420 atgagcagtg tgtgggggat gtaggctgg ccgactactg gggcatactg tgcttccaag        480
ggggcggtac gtatcatgtc gaaaagcgca gcgctggatt gcgcactgaa ggactacgat       540
gtgcgtgtca acacagtaca tccgggcccg atcaagaccc cgatgatgga tgatgaagaa       600
ggtgctgagg aaatgttttc acagcgtacg gagacaccta tgggtcacat cggcgaaccg       660
aatgacatcg catgggtctg tgtgtacctg gcatctgacg aatcgaaatt tgcgacgggt       720
gcagaatttg tggtcgacgg cgggaggacc gcacagtaa                              759

<210> SEQ ID NO 150
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 150

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Glu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190
```

Thr Pro Met Met Asp Asp Glu Glu Gly Ala Glu Met Phe Ser Gln
            195                 200                 205

Arg Thr Glu Thr Pro Met Gly His Ile Gly Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 151
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 151
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcaggattat ggtggttaa aagcgttgaa        300 gacactacca cggaggaatg gcgtaaactg ctgtccgtta atctggatgg tgttttttc        360 ggcacccgtc tgggcattca gcgcatgaaa ataaaggct tgggcgctag catcatcaat        420
atgagcagtg tgtgggggat tgtaggctgg ccgactacag gggcatactg tgcttccaag       480
ggggcggtac gtatcatgtc gaaaagcgca gcgctggatt gcgcactgaa ggactacgat       540
gtgcgtgtca acacagtaca tccgggcccg atcaagaccc cgatgaacga tgatgaagaa       600
ggtgctgagg aaatgttttc acagcgtacg gagaccccta tgggtcacat tggcgaaccg       660
aatgacatcg catgggtctg tgtgtacctg gcatctgacg aatcgaaatt tgcgacgggt       720
gcagaatttg tggtcgacgg cgggaggacc gcacagtaa                              759

<210> SEQ ID NO 152
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 152

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

```
Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Asn Asp Asp Glu Glu Gly Ala Glu Met Phe Ser Gln
            195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 153
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 153

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggatta tggtggttaa aagcgttgaa     300
gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagtg tgtgggggat tgtaggctgg ccgactacag gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gaggcaccta tgggtcacat tggcgaaccg     660
aatgacatcg catgggtctg tgtgtacctg gcatctgacg aatcgaaatt tgcgacgggt     720
gcagaatttg tggtcgacgg cgggagggc gcacagtaa                             759
```

<210> SEQ ID NO 154
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 154

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Val Val Asn Asn Ala Gly Ile Met Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
130                 135                 140
Trp Gly Ile Val Gly Trp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Glu Glu Gly Ala Glu Glu Met Phe Ser Gln
        195                 200                 205
Arg Thr Glu Ala Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Gly Ala Gln
                245                 250
```

<210> SEQ ID NO 155
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 155

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat ggtggttaa aagcgttgaa      300
gacactacca cggaggaatg cgtaaactg ctgtccgtta atctggatgg tgtttttttc      360
ggcacccgtc tgggcattca gcgcatgaaa aataaaggct gggcgctag catcatcaat      420
atgagcagtg tgtggggat tgtaagcgat ccgactacag ggcatactg tgcgtccaag      480
ggggcggtac gtatcatgtc gaaaagcgca gcgctggatt gcgcactgaa ggactacgat      540
```

-continued

```
gtgcgtgtca acacagtaca tccgggcccg atcaagaccc cgatgatgga tgacgaagaa    600
ggtgcttggg aaatgttttc acagcgtacg gagacccta tgggtcacat tggcgaaccg     660
aatgacatcg catgggtctg tgtgtacctg gcatctgacg aatcgaaatt tgcgacgggt    720
gcagaatttg tggtcgacgg cgggaggacc gcacagtaa                            759
```

<210> SEQ ID NO 156
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 156

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Ser Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Trp Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 157
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 157

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat ggtggttaa aagcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgtgggggat gtaggctgg ccgactacag gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgta tgatgaagaa     600
ggtgctgagg aaatgttttc acagcgtacg gagaccccta tgggtcacat ggcgaaccg     660
aatgacatcg catgggtctg tgtgtacctg gcatctgacg aatcgaaatt tgcgacgggt     720
gcagaatttg tggtcgacgg cgggaggaca gcatggtaa                            759
```

<210> SEQ ID NO 158
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 158

```
Met Thr Asp Arg Leu Lys Gly Lys Val Ala Ile Val Thr Gly Gly Thr
1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Tyr Asp Glu Glu Gly Ala Glu Glu Met Phe Ser Gln
        195                 200                 205
```

```
Arg Thr Glu Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Trp
                245                 250

<210> SEQ ID NO 159
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 159
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggatta tggtggttaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagtg tgtgggggat gtaggctgg ccgactacag gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gaggcaccta tgggtcacat tggcgaaccg     660
aatgacatcg catgggtctg tgtgtacctg gcatctgacg aatcgaaatt tgcgacgggt     720
gcagaatttg tggtcgacgg cgggaggaca gcatggtaa                           759

<210> SEQ ID NO 160
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 160

Met Thr Asp Arg Leu Lys Gly Lys Val Ala Ile Val Thr Gly Gly Thr
1                5                  10                 15

Gln Gly Ile Gly Leu Ala Ile Ala Asp Lys Phe Val Glu Glu Gly Ala
                20                  25                 30

Lys Val Val Ile Thr Gly Arg Arg Ala Asp Val Gly Glu Lys Ala Ala
            35                  40                 45

Lys Ser Ile Gly Gly Thr Asp Val Ile Arg Phe Val Gln His Asp Val
        50                  55                 60

Ser Asp Glu Ala Gly Trp Pro Lys Leu Phe Asp Thr Thr Glu Glu Ala
65                  70                  75                 80

Phe Gly Pro Val Thr Thr Val Val Asn Asn Ala Gly Ile Met Val Val
                85                  90                 95

Lys Ser Val Glu Asp Thr Thr Thr Glu Glu Trp Arg Lys Leu Leu Ser
            100                 105                110
```

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Val
        130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Gly Ala Glu Met Phe Ser Gln
        195                 200                 205

Arg Thr Glu Ala Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Trp
                245                 250

<210> SEQ ID NO 161
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 161

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt cgacaccac cgaggaggca     240
ttcggcccgg ttacgaccgt agtgaacaat gcaggatta tggtggtaa aagcgttgaa      300
gacactacca cggaggaatg gcgtaaactg ctgtccgttg gtctggatgg tgttttttc     360
ggcacccgtc tgggcattca gcgcatgaaa aataaaggct gggcgctag catcatcaat     420
atgagcagtg tgtggggat gtaggctgg ccgactacag gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgcatga tgatgaagaa     600
ggtgctgagg aaatgttttc acagcgtacg gagaccccta tgggtcacat tggcgaaccg     660
aatgacatcg catgggtctg tgtgtacctg gcatctgacg aatcgaaatt tgcgacgggt     720
gcagaatttg tggtcgacgg cgggaggaca gcacagtaa                            759
```

<210> SEQ ID NO 162
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 162

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Gly Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met His Asp Asp Glu Glu Gly Ala Glu Met Phe Ser Gln
        195                 200                 205

Arg Thr Glu Thr Pro Met Gly His Ile Gly Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 163
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 163
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcagggatta tggtggttaa aagcgttgaa   300
gacactacca cggaggaatg gcgtaaactg ctgtccgtta atctggatgg tgttttttc    360 ggcacccgtc tgggcattca gcgcatgaaa aataaaggct gggcgctag catcatcaat   420 atgagcagtg tgtggggat tgtaggcgat ccgactacag gggcatactg tgcgtccaag   480
gggcgcgtac gtatcatgtc gaaaagcgca gcgctggatt gcgcactgaa ggactacgat   540
gtgcgtgtca acacagtaca tccgggcccg atcaagaccc cgatgatgga tgacgaagaa   600
ggtgctgggg aaatgttttc acagcgtacg gagacccta tgggtcacat tggcgaaccg   660

```
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 164
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 164

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Met Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Asp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Glu Glu Gly Ala Gly Glu Met Phe Ser Gln
        195                 200                 205
Arg Thr Glu Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250
```

<210> SEQ ID NO 165
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 165

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
```

```
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcaggatta tggtggttaa agcgttgaa     300 gacactacca cggaggaatg gcgtaaattg ctgtccgtta atctggatgg tgttttttc    360 ggcacccgtc tgggcattca gcgcatgaaa aataaaggct gggcgctag catcatcaat    420 atgagcagtg tgtggggat tgtaggctgg ccgactactg gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgcagga tgatgaagaa    600
ggtgctgagg aaatgttttc acagcgtacg gagacccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 166
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri <400> SEQUENCE: 166

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Gln Asp Asp Glu Glu Gly Ala Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Arg Thr Ala Gln
            245                 250

<210> SEQ ID NO 167
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 167

```
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcaggattag tggtggttaa aagcgttgaa    300
gacactacca cggaggaatg gcgtaaactg ctgtccgtta atctggatgg tgttttttc     360 ggcacccgtc tgggcattca gcgcatgaaa aataaaggct gggcgctag catcatcaat    420 atgagcagtg tttgggggat gtaggctgg ccgactacag gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgcatga tgatgaagaa    600
ggtgctgagg aaatgttttc acagcgtacg gaggcaccta tgggtcacat ggcgaaccg     660 aatgacatcg catgggtctg tgtgtacctg gcatctgacg aatcgaaatt tgcgacgggt    720
gcagaatttg tggtcgacgg cgggaggaca gcacagtaa                          759
```

<210> SEQ ID NO 168
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 168

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

```
Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met His Asp Asp Glu Glu Gly Ala Glu Met Phe Ser Gln
        195                 200                 205

Arg Thr Glu Ala Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 169
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 169

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt cgacaccac cgaggaggca      240 ttcggcccgg ttacgaccgt agtgaacaat gcaggggatta tggtggttaa aagcgttgaa    300
gacactacca cggaggaatg cgtaaactg ctgtccgtta atctggatgg tgttttttc       360 ggcacccgtc tgggcattca gcgcatgaaa aataaaggct tgggcgctag catcatcaat    420
atgagcagtg tgtgggggat tgtaggctgg ccgactacag gggcatactg tgcttccaag    480
gggcgggtac gtatcatgtc gaaaagcgca gcgctggatt gcgcactgaa ggactacgat    540
gtgcgtgtca acacagtaca tccgggcccg atcaagaccc cgatgatgga tgatgaagaa    600
ggtgctgagg aaatgttttc acagcgtacg gagccaccta tgggtcacat ggcgaaccg     660 aatgacatcg catgggtctg tgtgtacctg gcatctgacg aatcgaaatt tgcgacgggt   720
gcagaatttg tggtcgacgg cgggaggacc gcacagtaa                           759
```

<210> SEQ ID NO 170
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 170

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45
```

```
Lys Ser Ile Gly Gly Thr Asp Val Ile Arg Phe Val Gln His Asp Val
 50                  55                  60

Ser Asp Glu Ala Gly Trp Pro Lys Leu Phe Asp Thr Thr Glu Glu Ala
 65                  70                  75                  80

Phe Gly Pro Val Thr Val Val Asn Asn Ala Gly Ile Met Val Val
                 85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Val
        130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp Glu Glu Gly Ala Glu Met Phe Ser Gln
                195                 200                 205

Arg Thr Glu Pro Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

```
<210> SEQ ID NO 171
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 171
atgaccgatc gtctgaaggg caaagtagcc atcgtaaccg cgggacacaa aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat cgctttgtc     180 cagcacgatg tatccgatga agcaggctgg cctaaactgt cgacaccac cgaggaggca     240 ttcggcccgg ttacgaccgt agtgaacaat gcaggggattc aagtggttaa agcgttgaa    300 gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgtggggat gtaggctgg ccgactacag ggcatactg tgcttccaag       480 ggggcggtac gtatcatgtc gaaaagcgca gcgctggatt gcgcactgaa ggactacgat    540
gtgcgtgtca acacagtaca tccgggcccg atcaagaccc cgatgatgga tgatgaagaa    600
ggtgctgagg aaatgttttc acagcgtacg gaacacccga tgggtcacat tggcgaaccg   660
aatgacatcg catgggtctg tgtgtacctg gcatctgacg aatcgaaatt tgcgacgggt    720
gcagaatttg tggtcgacgg cgggaggacc gcacagtaa                            759
```

```
<210> SEQ ID NO 172
```

<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 172

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Gln Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu His Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 173
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 173
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggggatta tggtggttaa aagcgttgaa     300
gacactacca cggaggaatg cgtaaactg ctgtccgtta atctggatgg tgttttttc      360

```
ggcacccgtc tgggcattca gcgcatgaaa aataaaggct tgggcgctag catcatcaat    420
atgagcagtg tgtggggat tgtaagcgat ccgactacag gggcatactg tgcgtccaag     480
ggggcggtac gtatcatgtc gaaaagcgca gcgctggatt gcgcactgaa ggactacgat    540
gtgcgtgtca acacagtaca tccgggcccg atcaagaccc cgatgatgga tgatgaagaa    600
ggtgctgagg aaatgttttc acagcgtacg gagacccta tgggtcacat tggcgaaccg     660
aatgacatcg catgggtctg tgtgtacctg gcatctgacg aatcgaaatt tgcgacgggt    720
gcagaatttg tggtcgacgg cgggaggacc gcacagtaa                            759
```

```
<210> SEQ ID NO 174
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 174
```

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Ser Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

```
<210> SEQ ID NO 175
<211> LENGTH: 759
<212> TYPE: DNA
<213> ORGANISM: Artificial Sequence
```

<220> FEATURE:
<223> OTHER INFORMATION: Aldo-keto reductase variant from Lactobacillus kefiri

<400> SEQUENCE: 175

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcaggattag tggtggttaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagtg tttgggggat gtaggctgg ccgactacag gggcatactg tgcttccaag   480
ggggcggtac gtatcatgtc gaaaagcgca gcgctggatt gcgcactgaa ggactacgat   540
gtgcgtgtca acacagtaca tccgggcccg atcaagaccc cgatgatgga tgatgaagaa   600
ggtgctgagg aaatgttttc acagcgtacg gagaatccta tgggtcacat tggcgaaccg   660
aatgacatcg catgggtctg tgtgtacctg gcatctgacg aatcgaaatt tgcgacgggt   720
gcagaatttg tggtcgacgg cgggaggggc gcacagtaa                          759
```

<210> SEQ ID NO 176
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 176

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190
```

```
Thr Pro Met Met Asp Asp Glu Glu Gly Ala Glu Met Phe Ser Gln
        195                 200                 205

Arg Thr Glu Asn Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Gly Ala Gln
                245                 250

<210> SEQ ID NO 177
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 177
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat ggtggttaa aagcgttgaa      300 gacactacca cggaggaatg gcgtaaactg ctgtccgtta tctggatgg tgtttttttc      360 ggcacccgtc tgggcattca gcgcatgaaa ataaaggct tgggcgctag catcatcaat      420
atgagcagtg tgtggggat tgtaggctgg ccgactacag gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgcatta tgatgaagaa     600
ggtgctgagg aaatgttttc acagcgtacg gagacccta tgggtcacat tggcgaaccg      660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 178
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 178

Met Thr Asp Arg Leu Lys Gly Lys Val Ala Ile Val Thr Gly Gly Thr
1               5                  10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95
```

```
Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met His Tyr Asp Glu Glu Gly Ala Glu Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 179
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 179

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggggatta tggtggttaa aagcgttgaa     300
gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagtg tgtggggat tgtaggctgg ccgactacag gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgta tgatgaagaa     600
ggtgctgagg aaatgttttc acagcgtacg gagaccccta tgggtcacat ggcgaaccg     660 aatgacatcg catgggtctg tgtgtacctg gcatctgacg aatcgaaatt tgcgacgggt     720
gcagaatttg tggtcgacgg cgggaggggc gcatggtaa                           759
```

<210> SEQ ID NO 180
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 180

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Asn Asn Ala Gly Ile Met Val Val
                85                  90                  95
Lys Ser Val Glu Asp Thr Thr Thr Glu Glu Trp Arg Lys Leu Leu Ser
                100                 105                 110
Val Asn Leu Asp Gly Val Phe Phe Gly Thr Arg Leu Gly Ile Gln Arg
            115                 120                 125
Met Lys Asn Lys Gly Leu Gly Ala Ser Ile Ile Asn Met Ser Ser Val
130                 135                 140
Trp Gly Ile Val Gly Trp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Tyr Asp Glu Glu Gly Ala Glu Glu Met Phe Ser Gln
        195                 200                 205
Arg Thr Glu Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Gly Ala Trp
                245                 250
```

<210> SEQ ID NO 181
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 181

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattag tggtggttaa agcgttgaa      300
gacactacca cggaggaatg cgtaaactg ctgtccgtta atctggatgg tgttttttc       360
ggcacccgtc tgggcattca gcgcatgaaa aataaaggct gggcgctag catcatcaat     420
atgagcagtg tttgggggat tgtaggctgg ccgactacag ggcatactg tgcttccaag     480
ggggcggtac gtatcatgtc gaaaagcgca gcgctggatt gcgcactgaa ggactacgat     540
```

```
gtgcgtgtca acacagtaca tccgggcccg atcaagaccc cgatgatgga tgatgaagaa    600
ggtgctgagg aaatgttttc acagcgtacg gaggcaccta tgggtcacat tggcgaaccg    660
aatgacatcg catgggtctg tgtgtacctg gcatctgacg aatcgaaatt tgcgacgggt    720
gcagaatttg tggtcgacgg cgggagggggc gcatggtaa                          759
```

<210> SEQ ID NO 182
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 182

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Ala Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Gly Ala Trp
                245                 250
```

<210> SEQ ID NO 183
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 183

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat ggtggttaa aagcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat     420
atgagcagtg tgtgggggat gtaggctgg ccgactacag gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaacatttgt tcagcgtacg gaggcaccta tgggtcacat ggcgaaccg      660
aatgacatcg catgggtctg tgtgtacctg gcatctgacg aatcgaaatt tgcgacgggt     720
gcagaatttg tggtcgacgg cgggaggaca gcatggtaa                            759
```

<210> SEQ ID NO 184
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 184

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Glu Thr Phe Val Gln
        195                 200                 205
```

```
Arg Thr Glu Ala Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Trp
                245                 250
```

<210> SEQ ID NO 185
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 185

```
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcagggattc aagtggttaa agcgttgaa        300
gacactacca cggaggaatg gcgtaaactg ctgtccgtta atctggatgg tgttttttc        360
ggcacccgtc tgggcattca gcgcatgaaa aataaaggct gggcgctag catcatcaat        420
atgagcagtg tgtgggggat gtaggctgg ccgactaccg gggcatactg tgcttccaag        480
ggggcggtac gtatcatgtc gaaaagcgca gcgctggatt gcgcactgaa ggactacgat       540
gtgcgtgtca acacagtaca tccgggcccg atcaagaccc cgatgatgga tgatgaagaa       600
ggtgctgagg aaatgttttc acagcgtacg gaaactggta tgggtcacat tggcgaaccg       660
aatgacatcg catgggtctg tgtgtacctg catctgacg aatcgaaatt tgcgacgggt        720
gcagaatttg tggtcgacgg cgggaggacc gcacagtaa                              759
```

<210> SEQ ID NO 186
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 186

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Gln Val Val
                85                  90                  95
Lys Ser Val Glu Asp Thr Thr Thr Glu Glu Trp Arg Lys Leu Leu Ser
            100                 105                 110
```

```
Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Gly Ala Glu Met Phe Ser Gln
        195                 200                 205

Arg Thr Glu Thr Gly Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 187
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 187

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcaggattat ggtggttaa aagcgttgaa   300
gacactacca cggaggaatg gcgtaaagaa ctgtccgtta atctggatgg tgtttttttc   360
ggcacccgtc tgggcattca gcgcatgaaa aataaaggct gggcgctag catcatcaat   420
atgagcagtg tgtggggat gtaggctgg ccgactactg gggcatactg tgcttccaag   480
ggggcggtac gtatcatgtc gaaaagcgca gcgctggatt gcgcactgaa ggactacgat   540
gtgcgtgtca acacagtaca tccgggcccg atcaagaccc cgatgatgga tgatgaagaa   600
ggtgctgagg aaatgttttc acagcgtacg gaggtcccta tgggtcacat cggcgaaccg   660
aatgacatcg catgggtctg tgtgtacctg gcatctgacg aatcgaaatt tgcgacgggt   720
gcagaatttg tggtcgacgg cgggaggacc gcacagtaa                          759
```

<210> SEQ ID NO 188
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 188

```
Met Thr Asp Arg Leu Lys Gly Lys Val Ala Ile Val Thr Gly Gly Thr
1               5                  10                  15
```

Gln Gly Ile Gly Leu Ala Ile Ala Asp Lys Phe Val Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Glu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Val Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 189
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 189
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcaggattat ggtggttaa aagcgttgaa    300 gacactacca cggaggaatg gcgtaaactg ctgtccgtta atctggatgg tgtttttttc   360
ggcacccgtc tgggcattca gcgcatgaaa aataaaggct gggcgctag catcatcaat   420 atgagcagtg tgtgggggat gtaggcgat ccgactacag gggcatactg tgtgtccaag   480
ggggcggtac gtatcatgtc gaaaagcgca gcgctggatt gcgcactgaa ggactacgat   540
gtgcgtgtca acacagtaca tccgggcccg atcaagaccc cgatgatgga tgatgaagaa   600
ggtgctgagg aaatgttttc acagcgtacg gagacccta tgggtcacat tggcgaaccg   660

```
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 190
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 190

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Asp Pro Thr Thr Gly Ala Tyr Cys Val Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 191
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 191

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
```

```
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgaccgt agtgaacaat gcaggatta tggtggttaa aagcgttgaa     300
gacactacca cggaggaatg gcgtaaactg ctgtccgtta atctggatgg tgttttttc     360 ggcacccgtc tgggcattca gcgcatgaaa aataaaggct tgggcgctag catcatcaat    420
atgagcagtg tgtgggggat tgtaggcgat ccgactacag gggcatactg tgtgtccaag    480
ggggcggtac gtatcatgtc gaaaagcgca gcgctggatt gcgcactgaa ggactacgat    540
gtgcgtgtca acacagtaca tccgggcccg atcaagaccc cgatgatgga ttcggaagaa    600
ggtgctgagg aaatgttttc acagcgtacg gagacccccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 192
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 192

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
        130                 135                 140

Trp Gly Ile Val Gly Asp Pro Thr Thr Gly Ala Tyr Cys Val Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Glu Glu Gly Ala Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Arg Thr Ala Gln
            245                 250

<210> SEQ ID NO 193
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 193

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat ggtggttaa aagcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagtg tgtggggat gtaggctgg ccgactcccg gggcatactg tgcttccaag      480
ggggcggtac gtatcatgtc gaaaagcgca gcgctggatt gcgcactgaa ggactacgat     540
gtgcgtgtca acacagtaca tccgggccca atcaagaccc cgatgatgga tgatgaagaa     600
ggtgctgagg aaatgttttc acagcgtacg gagccccta tgggtcacat ggcgaaccg      660 aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 194
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 194

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

-continued

```
Trp Gly Ile Val Gly Trp Pro Thr Pro Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Pro Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 195
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 195

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt cgacaccac cgaggaggca     240 ttcggcccgg ttacgaccgt agtgaacaat gcagggatta tggtggttaa aagcgttgaa     300
gacactacca cggaggaatg gcgtaaactg ctgtccgtta atctggatgg tgtttttttc     360
ggcacccgtc tgggcattca gcgcatgaaa aataaaggct tgggcgctag catcatcaat     420
atgagcagtg tgtgggggat tgtaggcgat ccgactacag gggcatactg tgcttccaag     480 gggggcggtac gtatcatgtc gaaaagcgca gcgctggatt gcgcactgaa ggactacgat     540
gtgcgtgtca acacagtaca tccgggcccg atcaagaccc cgatgatgga ttcggaagaa     600
ggtgctgggg aaatgttttc acagcgtacg gagaccccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 196
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 196

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45
```

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Glu Glu Gly Ala Trp Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 197
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 197
atgaccgatc gtctgaaggg caaagtagcc atcgtaaccg cgggacaca aggtatcggt      60 ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggatta tggtggttaa aagcgttgaa     300
gacactacca cggaggaatg cgtaaattg ctgtccgtta atctggatgg tgtttttttc     360
ggcacccgtc tgggcattca gcgcatgaaa ataaaggct tgggcgctag catcatcaat     420
atgagcagtg tgtggggat tgtaggctgg ccgactactg ggcatactg tgcttccaag     480 ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gagacaatga tgggtcacat cggcgaaccg     660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 198

-continued

<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 198

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Thr Met Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 199
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 199
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcaggggatta tggtggttaa agcgttgaa   300 gacactacca cggaggaatg gcgtaaactg ctgtccgtta atctggatgg tgttttttc   360

```
ggcacccgtc tgggcattca gcgcatgaaa aataaaggct tgggcgctag catcatcaat    420
atgagcagtg tgtggggat tgtaggcgat ccgactacag gggcatactg tgcgtccaag    480
ggggcggtac gtatcatgtc gaaaagcgca gcgctggatt gcgcactgaa ggactacgat    540
gtgcgtgtca acacagtaca tccgggcccg atcaagaccc cgatgatgga ttcggaagaa    600
ggtgctttgg aaatgttttc acagcgtacg agaccccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                         759
```

<210> SEQ ID NO 200
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 200

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Glu Glu Gly Ala Leu Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 201
<211> LENGTH: 759
<212> TYPE: DNA
<213> ORGANISM: Artificial Sequence

```
<220> FEATURE:
<223> OTHER INFORMATION: Aldo-keto reductase variant from Lactobacillus
      kefiri

<400> SEQUENCE: 201
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcaggattat ggtggttaa aagcgttgaa    300 gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg tgtggggat gtaggcgat ccgactacag gggcatactg tgcttccaag    480
ggggcggtac gtatcatgtc gaaaagcgca gcgctggatt gcgcactgaa ggactacgat    540
gtgcgtgtca acacagtaca tccgggcccg atcaagaccc cgatgatgga tgacgaagaa    600
ggtgctgagg aaatgttttc acagcgtacg gagaccccta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                           759

<210> SEQ ID NO 202
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 202

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190
```

```
Thr Pro Met Met Asp Asp Glu Glu Gly Ala Glu Met Phe Ser Gln
            195                 200                 205

Arg Thr Glu Thr Pro Met Gly His Ile Gly Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 203
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 203

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat tggtggttaa agcgttgaa     300
gacactacca cggaggaatg gcgtaaattg ctgtccgtta atctggatgg tgttttttc     360
ggcacccgtc tgggcattca gcgcatgaaa ataaaggct tgggcgctag catcatcaat     420
atgagcagtg tgtgggggat tgtaggctgg ccgactactg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gaggtcaata tgggtcacat cggcgaaccg     660
aatgacatcg catgggtctg tgtgtacctg gcatctgacg aatcgaaatt tgcgacgggt     720
gcagaatttg tggtcgacgg cgggaggacc gcacagtaa                              759
```

<210> SEQ ID NO 204
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 204

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95
```

```
Lys Ser Val Glu Asp Thr Thr Thr Glu Glu Trp Arg Lys Leu Leu Ser
             100                 105                 110

Val Asn Leu Asp Gly Val Phe Phe Gly Thr Arg Leu Gly Ile Gln Arg
             115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
             165                 170                 175

Lys Asp Tyr Asp Val Arg Val Asn Thr Val His Pro Gly Pro Ile Lys
             180                 185                 190

Thr Pro Met Met Asp Asp Glu Glu Gly Ala Glu Met Phe Ser Gln
             195                 200                 205

Arg Thr Glu Val Asn Met Gly His Ile Gly Glu Pro Asn Asp Ile Ala
             210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
             245                 250
```

<210> SEQ ID NO 205
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 205

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggatta tggtggttaa aagcgttgaa     300
gacactacca cggaggaatg gcgtaaactg ctgtccgtta atctggatgg tgttttttttc    360
ggcacccgtc tgggcattca gcgcatgaaa aataaaggct tgggcgctag catcatcaat     420
atgagcagtg tgtgggggat tgtaggctgg ccgactaccg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gaacgcccga tggtcacat ggcgaaccg      660
aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 206
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 206

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Met Val Val
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Glu Met Phe Ser Gln
        195                 200                 205

Arg Thr Glu Arg Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 207
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 207
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat ggtggttaa aagcgttgaa      300 gacactacca cggaggaatg gcgtaaattg ctgtccgtta atctggatgg tgtttttttc     360
ggcacccgtc tgggcattca gcgcatgaaa aataaaggct gggcgctag catcatcaat     420 atgagcagtg tgtggggat tgtaggctgg ccgactactg ggcatactg tgcttccaag      480 ggggcggtac gtatcatgtc gaaagcgca gcgctggatt gcgcactgaa ggactacgat      540

```
gtgcgtgtca acacagtaca tccgggcccg atcaagaccc cgatgatgga tgatgaagaa    600
ggtgctgagg aaatgttttc acagcgtacg gagacagaga tgggtcacat cggcgaaccg    660
aatgacatcg catgggtctg tgtgtacctg gcatctgacg aatcgaaatt tgcgacgggt    720
gcagaatttg tggtcgacgg cgggaggacc gcacagtaa                           759
```

<210> SEQ ID NO 208
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 208

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Thr Glu Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 209
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 209

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat ggtggttaa aagcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgtggggat gtaggctgg ccgactacag gggcatactg tgcttccaag      480
ggggcggtac gtatcatgtc gaaaagcgca gcgctggatt gcgcactgaa ggactacgat     540
gtgcgtgtca acacagtaca tccgggcccg atcaagaccc cgatgcatga tgatgaagaa     600
ggtgctgagg aaatgttttc acagcgtacg gagacccccta tgggtcacat ggcgaaccg     660
aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 210
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 210

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Met Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Trp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met His Asp Asp Glu Glu Gly Ala Glu Glu Met Phe Ser Gln
        195                 200                 205
```

```
Arg Thr Glu Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250

<210> SEQ ID NO 211
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 211
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggatta tggtggttaa agcgttgaa      300 gacactacca cggaggaatg gcgtaaattg ctgtccgtta atctggatgg tgttttttc     360 ggcacccgtc tgggcattca gcgcatgaaa aataaaggct gggcgctag catcatcaat     420 atgagcagtg tgtgggggat gtaggctggc cgactactg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gagacaacga tgggtcacat cggcgaaccg     660
aatgacatcg catgggtctg tgtgtacctg gcatctgacg aatcgaaatt tgcgacgggt     720
gccgaatttg tggtcgacgg cgggaggacc gcacagtaa                           759

<210> SEQ ID NO 212
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 212

Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Met Val Val
                85                  90                  95
Lys Ser Val Glu Asp Thr Thr Thr Glu Glu Trp Arg Lys Leu Leu Ser
            100                 105                 110
```

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Gly Ala Glu Met Phe Ser Gln
        195                 200                 205

Arg Thr Glu Thr Thr Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 213
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 213
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcaggatta tggtggtaa aagcgttgaa   300 gacactacca cggaggaatg gcgtaaactg ctgtccgtta atctggatgg tgttttttc    360 ggcacccgtc tgggcattca gcgcatgaaa aataaaggct ggcgctag catcatcaat     420 atgagcagtg tgtggggat gtaggctgg ccgactaccg gggcatactg tgcttccaag   480
ggggcggtac gtatcatgtc gaaaagcgca gcgctggatt gcgcactgaa ggactacgat    540
gtgcgtgtca acacagtaca tccgggcccg atcaagaccc cgatgatgga tgatgaagaa    600
ggtgctgagg aaatgttttc acagcgtacg gaaactggta tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                          759

<210> SEQ ID NO 214
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 214

Met Thr Asp Arg Leu Lys Gly Lys Val Ala Ile Val Thr Gly Gly Thr
1               5                   10                  15

| | | | | | | | | | | |
|---|---|---|---|---|---|---|---|---|---|---|
|Gln|Gly|Ile|Gly|Leu|Ala|Ile|Ala|Asp|Lys|Phe|Val|Glu|Glu|Gly|Ala|
| | |20| | | |25| | | |30| | | | | |

Lys Val Val Ile Thr Gly Arg Arg Ala Asp Val Gly Glu Lys Ala Ala
                35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65              70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp Glu Glu Gly Ala Glu Met Phe Ser Gln
                195                 200                 205

Arg Thr Glu Thr Gly Met Gly His Ile Gly Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 215
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 215
atgaccgatc gtctgaaggg caaagtagcc atcgtaaccg gcgggacaca aggtatcggt       60
ttggcaatcg ccgataaatt tgtagaggag ggtgcgaaag tagttattac tggtcgtcgt      120
gcggatgtag gtgaaaaggc cgccaaatca atcggcggca ctgatgttat tcgctttgtc      180
cagcacgatg tatccgatga agcaggctgg cctaaactgt tcgacaccac cgaggaggca      240
ttcggcccgg ttacgaccgt agtgaacaat gcagggatta tggtggttaa aagcgttgaa      300
gacactacca cggaggaatg gcgtaaactg ctgtccgtta atctggatgg tgtttttttc      360
ggcacccgtc tgggcattca gcgcatgaaa aataaaggct gggcgctag catcatcaat      420 atgagcagtg tgtggggat gtaggctgg ccgactacag gggcatactg tgcttccaag      480
ggggcggtac gtatcatgtc gaaaagcgca gcgctggatt gcgcactgaa ggactacgat      540
gtgcgtgtca acacagtaca tccgggcccg atcaagaccc cgatgatgga tgatgaagaa      600
ggtgctgagg aaatgttttc acagcgtacg gaagaaggta tgggtcacat tggcgaaccg      660

```
aatgacatcg catgggtctg tgtgtacctg gcatctgacg aatcgaaatt tgcgacgggt    720
gcagaatttg tggtcgacgg cgggaggacc gcacagtaa                          759
```

<210> SEQ ID NO 216
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 216

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Glu Gly Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 217
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 217

```
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
```

-continued

```
gcggatgtag gtgaaaaggc cgccaaatca atcggcggca ctgatgttat tcgctttgtc      180
cagcacgatg tatccgatga agcaggctgg cctaaactgt tcgacaccac cgaggaggca      240
ttcggcccgg ttacgaccgt agtgaacaat gcaggattat ggtggttaa aagcgttgaa       300 gacactacca cggaggaatg gcgtaaatgg ctgtccgtta atctggatgg tgttttttc       360 ggcacccgtc tgggcattca gcgcatgaaa aataaaggct gggcgctag catcatcaat      420 atgagcagtg tgtggggat tgtaggctgg ccgactactg gggcatactg tgcttccaag      480
ggggcggtac gtatcatgtc gaaaagcgca gcgctggatt gcgcactgaa ggactacgat     540
gtgcgtgtca acacagtaca tccggggccg atcaagaccc cgatgatgga tgatgaagaa     600
ggtgctgagg aaatgttttc acagcgtacg gagacaaata tgggtcacat cggcgaaccg     660
aatgacatcg catgggtctg tgtgtacctg gcatctgacg aatcgaaatt tgcgacgggt     720
gcagaatttg tggtcgacgg cgggaggacc gcacagtaa                            759
```

<210> SEQ ID NO 218
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 218

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Trp Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
            195                 200                 205

Arg Thr Glu Thr Asn Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Arg Thr Ala Gln
            245                 250

<210> SEQ ID NO 219
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 219

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat cgctttgtc      180 cagcacgatg tatccgatga agcaggctgg cctaaactgt tcgacaccac cgaggaggca     240
ttcggcccgg ttacgaccgt agtgaacaat gcaggattag tggtggttaa aagcgttgaa     300
gacactacca cggaggaatg gcgtaaattg ctgtccgtta atctggatgg tgttttttc     360 ggcacccgtc tgggcattca gcgcatgaaa aataaaggct gggcgctag catcatcaat     420 atgagcagtg tgtgggggat gtaggctgg ccgactactg gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gagacaaata tgggtcacat cggcgaaccg     660
aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 220
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 220

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

```
Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Glu Met Phe Ser Gln
        195                 200                 205

Arg Thr Glu Thr Asn Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

<210> SEQ ID NO 221
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 221

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggatta tggtggttaa agcgttgaa      300 gacactacca cggaggaatg gcgtaaattg ctgtccgtta atctggatgg tgttttttc      360 ggcacccgtc tgggcattca gcgcatgaaa aataaaggct gggcgctag catcatcaat     420 atgagcagtg tgtggggat tgtaggctgg ccgactacag gggcatactg tgcttccaag     480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttctc ccagcgtacg gagggcaata tgggtcacat cggcgaaccg     660
aatgacatcg catgggtctg tgtgtacctg gcatctgacg aatcgaaatt tgcgacgggt     720
gcagaatttg tggtcgacgg cgggaggacc gcacagtaa                           759
```

<210> SEQ ID NO 222
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 222

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45
```

```
Lys Ser Ile Gly Gly Thr Asp Val Ile Arg Phe Val Gln His Asp Val
 50                  55                  60

Ser Asp Glu Ala Gly Trp Pro Lys Leu Phe Asp Thr Thr Glu Glu Ala
 65                  70                  75                  80

Phe Gly Pro Val Thr Thr Val Val Asn Asn Ala Gly Ile Met Val Val
                 85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Val
                130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp Glu Glu Gly Ala Glu Met Phe Ser Gln
                195                 200                 205

Arg Thr Glu Gly Asn Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 223
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 223
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat cgctttgtc    180 cagcacgatg tatccgatga agcaggctgg cctaaactgt tcgacaccac cgaggagca    240 ttcggcccgg ttacgaccgt agtgaacaat gcagggatta tggtggttaa aagcgttgaa   300
gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg tgtggggat gtaggctgg ccgactacag ggcatactg tgcttccaag     480 ggggcggtac gtatcatgtc gaaaagcgca gcgctggatt gcgcactgaa ggactacgat   540
gtgcgtgtca acacagtaca tccgggcccg atcaagaccc cgatgatgga tgatgaagaa   600
ggtgctgagg aaatgttttc acagcgtacg gaacacaaga tgggtcacat ggcgaaccg    660 aatgacatcg catgggtctg tgtgtacctg gcatctgacg aatcgaaatt tgcgacgggt   720
gcagaatttg tggtcgacgg cgggaggacc gcacagtaa                          759

<210> SEQ ID NO 224
```

<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 224

```
Met Thr Asp Arg Leu Lys Gly Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Met Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Trp Gly Ile Val Gly Trp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Asp Glu Glu Gly Ala Glu Met Phe Ser Gln
        195                 200                 205
Arg Thr Glu His Lys Met Gly His Ile Gly Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Arg Thr Ala Gln
                245                 250
```

<210> SEQ ID NO 225
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 225

| | | |
|---|---|---|
| atgaccgatc gtctgaaggg caaagtagcc atcgtaaccg gcgggacaca aggtatcggt | 60 |
| ttggcaatcg ccgataaatt tgtagaggag ggtgcgaaag tagttattac tggtcgtcgt | 120 |
| gcggatgtag gtgaaaaggc cgccaaatca atcggcggca ctgatgttat tcgctttgtc | 180 |
| cagcacgatg tatccgatga agcaggctgg cctaaactgt tcgacaccac cgaggaggca | 240 |
| ttcggcccgg ttacgaccgt agtgaacaat gcaggggatta tggtggttaa agcgttgaa | 300 |
| gacactacca cggaggaatg gcgtaaactg ctgtccgtta atctggatgg tgttttttc | 360 |

```
ggcacccgtc tgggcattca gcgcatgaaa aataaaggct tgggcgctag catcatcaat    420
atgagcagtg tgtggggat tgtaggctgg ccgactaccg gggcatactg tgcttccaag     480
ggggcggtac gtatcatgtc gaaaagcgca gcgctggatt gcgcactgaa ggactacgat    540
gtgcgtgtca acacagtaca tccgggcccg atcaagaccc cgatgatgga tgatgaagaa    600
ggtgctgagg aaatgttttc acagcgtacg gaaactaaga tgggtcacat tggcgaaccg    660
aatgacatcg catgggtctg tgtgtacctg gcatctgacg aatcgaaatt tgcgacgggt    720
gcagaatttg tggtcgacgg cgggaggacc gcacagtaa                           759
```

```
<210> SEQ ID NO 226
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 226
```

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Thr Lys Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250
```

```
<210> SEQ ID NO 227
<211> LENGTH: 759
<212> TYPE: DNA
<213> ORGANISM: Artificial Sequence
```

```
<220> FEATURE:
<223> OTHER INFORMATION: Aldo-keto reductase variant from Lactobacillus
      kefiri

<400> SEQUENCE: 227
atgaccgatc gtctgaaggg caaagtagcc atcgtaaccg gcgggacaca aggtatcggt        60
ttggcaatcg ccgataaatt tgtagaggag ggtgcgaaag tagttattac tggtcgtcgt       120
gcggatgtag gtgaaaaggc cgccaaatca atcggcggca ctgatgttat tcgctttgtc       180
cagcacgatg tatccgatga agcaggctgg cctaaactgt tcgacaccac cgaggaggca       240
ttcggcccgg ttacgaccgt agtgaacaat gcaggattat ggtggttaa aagcgttgaa        300 gacactacca cggaggaatg gcgtaaactg ctgtccgtta atctggatgg tgttttttc        360 ggcacccgtc tgggcattca gcgcatgaaa aataaaggct gggcgctag catcatcaat       420 atgagcagtg tgtggggat gtaggctgg ccgactaccg gggcatactg tgcttccaag        480
ggggcggtac gtatcatgtc gaaaagcgca gcgctggatt gcgcactgaa ggactacgat       540
gtgcgtgtca acacagtaca tccgggcccg atcaagaccc cgatgatgga tgatgaagaa       600
ggtgctgagg aaatgttttc acagcgtacg aacgcggta tgggtcacat tggcgaaccg         660
aatgacatcg catgggtctg tgtgtacctg gcatctgacg aatcgaaatt tgcgacgggt       720
gcagaatttg tggtcgacgg cgggaggacc gcacagtaa                              759

<210> SEQ ID NO 228
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 228

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190
```

```
Thr Pro Met Met Asp Asp Glu Glu Gly Ala Glu Met Phe Ser Gln
            195                 200                 205

Arg Thr Glu Arg Gly Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 229
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 229
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agttggctgg cctaaactgt tcgacaccac cgaggaggca     240
ttcggcccgg ttacgaccgt agtgaacaat gcaggattta tggtggttaa agcgttgaa     300 gacactacca cggaggaatg gcgtaaactg ctgtccgtta atctggatgg tgttttttc     360 ggcacccgtc tgggcattca gcgcatgaaa ataaaggct tgggcgctag catcatcaat     420
atgagcagtg tgtggggat tgtaggctgg ccgactacag gggcatactg tgcttccaag     480 gggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gagacccta tgggtcacat tggcgaaccg     660
aatgacatcg catgggtctg tgtgtacctg gcatctgacg aatcgaaatt tgcgacgggt     720
gcagaatttg tggtcgacgg cgggaggacc gcacagtaa                            759

<210> SEQ ID NO 230
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 230

Met Thr Asp Arg Leu Lys Gly Lys Val Ala Ile Val Thr Gly Gly Thr
1                   5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Val Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95
```

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Glu Met Phe Ser Gln
            195                 200                 205

Arg Thr Glu Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 231
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 231
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcagggatta tggtggttaa agcgttgaa    300 gacactacca cggaggaatg gcgtaaactg ctgtccgtta atctggatgg tgtttttttc   360
ggcacccgtc tgggcattca gcgcatgaaa aataaaggct gaaagctag catcatcaat   420 atgagcagtg tgtgggggat gtaggctgg ccgactacag gggcatactg tgcttccaag    480
ggggcggtac gtatcatgtc gaaaagcgca gcgctggatt gcgcactgaa ggactacgat   540
gtgcgtgtca acacagtaca tccgggcccg atcaagaccc cgatgatgga tgatgaagaa   600
ggtgctgagg aaatgttttc acagcgtacg gagacccta tgggtcacat ggcgaaccg    660 aatgacatcg catgggtctg tgtgtacctg gcatctgacg aatcgaaatt tgcgacgggt   720
gcagaatttg tggtcgacgg cgggaggacc gcacagtaa                          759

<210> SEQ ID NO 232
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 232

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Asn Asn Ala Gly Ile Met Val Val
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Lys Ala Ser Ile Ile Asn Met Ser Ser Val
130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Arg Thr Ala Gln
                245                 250

<210> SEQ ID NO 233
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 233
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattat ggtggttaa aagcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagtg tgtgggggat tgtaggctgg ccgactacag gggcatactg tgcttccaag     480
ggggcggtac gtatcatgtc gaaaagcgca gcgctggatt gcgcactgaa ggactacgat     540

```
gtgcgtgtca acacagtaca tccgggcccg atcaagaccc cgatgatgga tgatgaagaa    600
ggtgctgagg aaatgttttc acagcgtacg gagacccta tgggtcacat ggcgaaccg    660 aatgacatcg catgggtctg tgtgtacctg gcatctacag aatcgaaatt tgcgacgggt    720
gcagaatttg tggtcgacgg cgggaggacc gcacagtaa                           759
```

<210> SEQ ID NO 234
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 234

```
Met Thr Asp Arg Leu Lys Gly Lys Val Ala Ile Val Thr Gly Gly Thr
 1               5                  10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Glu Ala
    65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
               100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
        130                 135                 140

Trp Gly Ile Val Gly Trp Pro Thr Thr Gly Ala Tyr Cys Ala Ser Lys
    145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Met Phe Ser Gln
        195                 200                 205

Arg Thr Glu Thr Pro Met Gly His Ile Gly Glu Pro Asn Asp Ile Ala
    210                 215                 220

Trp Val Cys Val Tyr Leu Ala Ser Thr Glu Ser Lys Phe Ala Thr Gly
    225                 230                 235                 240

Ala Glu Phe Val Val Asp Gly Gly Arg Thr Ala Gln
                245                 250
```

<210> SEQ ID NO 235
<211> LENGTH: 759
<212> TYPE: DNA
<213> ORGANISM: Artificial Sequence
<220> FEATURE:
<223> OTHER INFORMATION: Aldo-keto reductase variant from Lactobacillus kefiri

<400> SEQUENCE: 235

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcaggattta tggtggttaa aagcgttgaa     300
gacactacca cggaggaatg gcgtaaactg ctgtccgtta atctggatgg tgtttttttc     360
ggcacccgtc tgggcattca gcgcatgaaa aataaaggct gggcgctag catcatcaat      420
atgagcagtg tgtggggat gtaggctgg ccgactacag gggcatactg tgcttccaag       480
ggggcggtac gtatcatgtc gaaaagcgca gcgctggatt gcgcactgaa ggactacgat     540
gtgcgtgtca acacagtaca tccgggcccg atcaagaccc cgatgatgga tgatgaagaa     600
ggtgctgagg aaatgttttc acagcgtacg gagacccta tgggtcacat ggcgaaccg       660
aatgacatcg catgggtctg tgtgtacctg gcatctcaag aatcgaaatt tgcgacgggt     720
gcagaatttg tggtcgacgg cgggaggacc gcacagtaa                            759
```

<210> SEQ ID NO 236
<211> LENGTH: 252
<212> TYPE: PRT
<213> ORGANISM: Artificial Sequence
<220> FEATURE:
<223> OTHER INFORMATION: Aldo-keto reductase variant from Lactobacillus kefiri

<400> SEQUENCE: 236

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Glu Met Phe Ser Gln
        195                 200                 205
```

Arg Thr Glu Thr Pro Met Gly His Ile Gly Glu Pro Asn Asp Ile Ala
    210                 215                 220

Trp Val Cys Val Tyr Leu Ala Ser Gln Glu Ser Lys Phe Ala Thr Gly
225                 230                 235                 240

Ala Glu Phe Val Val Asp Gly Gly Arg Thr Ala Gln
                245                 250

<210> SEQ ID NO 237
<211> LENGTH: 759
<212> TYPE: DNA
<213> ORGANISM: Artificial Sequence
<220> FEATURE:
<223> OTHER INFORMATION: Aldo-keto reductase variant from Lactobacillus
      kefiri

<400> SEQUENCE: 237
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcagggatta tggtggttaa agcgttgaa   300 gacactacca cggaggaatg gcgtaaactg ctgtccgtta atctggatgg tgttttttc   360 ggcacccgtc tgggcattca gcgcatgaaa aataaaggct gggcgctag catcatcaat   420 atgagcagtg tgtggggat gtaggctgg ccgactacag gggcatactg tgcttccaag   480
ggggcggtac gtatcatgtc gaaaagcgca gcgctgcttt gcgcactgaa ggactacgat   540
gtgcgtgtca acacagtaca tccgggcccg atcaagaccc cgatgatgga tgatgaagaa   600
ggtgctgagg aaatgttttc acagcgtacg agaccccta tgggtcacat tggcgaaccg   660
aatgacatcg catgggtctg tgtgtacctg gcatctgacg aatcgaaatt tgcgacgggt   720
gcagaatttg tggtcgacgg cggggggacc gcacagtaa                          759

<210> SEQ ID NO 238
<211> LENGTH: 252
<212> TYPE: PRT
<213> ORGANISM: Artificial Sequence
<220> FEATURE:
<223> OTHER INFORMATION: Aldo-keto reductase variant from Lactobacillus
      kefiri

<400> SEQUENCE: 238

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Met Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
        130                 135                 140

Trp Gly Ile Val Gly Trp Pro Thr Thr Gly Ala Tyr Cys Ala Ser Lys
145                 150                 155                 160

Gly Ala Val Arg Ile Met Ser Lys Ser Ala Leu Leu Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Glu Glu Gly Ala Glu Glu Met Phe Ser Gln
        195                 200                 205

Arg Thr Glu Thr Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Gly Thr Ala Gln
                245                 250

```
<210> SEQ ID NO 239
<211> LENGTH: 252
<212> TYPE: PRT
<213> ORGANISM: Artificial Sequence
<220> FEATURE:
<223> OTHER INFORMATION: Synthetic engineered aldo-keto reductase
      variant
<220> FEATURE:
<221> NAME/KEY: MISC_FEATURE
<222> LOCATION: (17)..(17)
<223> OTHER INFORMATION: Xaa is a polar residue
<220> FEATURE:
<221> NAME/KEY: MISC_FEATURE
<222> LOCATION: (40)..(40)
<223> OTHER INFORMATION: Xaa is a basic residue
<220> FEATURE:
<221> NAME/KEY: MISC_FEATURE
<222> LOCATION: (64)..(64)
<223> OTHER INFORMATION: Xaa is an aliphatic residue
<220> FEATURE:
<221> NAME/KEY: MISC_FEATURE
<222> LOCATION: (68)..(68)
<223> OTHER INFORMATION: Xaa is a non-polar or aliphatic residue
<220> FEATURE:
<221> NAME/KEY: MISC_FEATURE
<222> LOCATION: (71)..(71)
<223> OTHER INFORMATION: Xaa is a non-polar residue
<220> FEATURE:
<221> NAME/KEY: MISC_FEATURE
<222> LOCATION: (94)..(94)
<223> OTHER INFORMATION: Xaa is a polar, aliphatic, or non-polar residue
<220> FEATURE:
<221> NAME/KEY: MISC_FEATURE
<222> LOCATION: (96)..(96)
<223> OTHER INFORMATION: Xaa is an aliphatic residue
<220> FEATURE:
<221> NAME/KEY: MISC_FEATURE
<222> LOCATION: (102)..(102)
<223> OTHER INFORMATION: Xaa is an acidic or polar residue
<220> FEATURE:
<221> NAME/KEY: MISC_FEATURE
<222> LOCATION: (110)..(110)
<223> OTHER INFORMATION: Xaa is an acidic or aromatic residue
<220> FEATURE:
<221> NAME/KEY: MISC_FEATURE
<222> LOCATION: (114)..(114)
<223> OTHER INFORMATION: Xaa is a non-polar residue
<220> FEATURE:
<221> NAME/KEY: MISC_FEATURE
<222> LOCATION: (135)..(135)
```

```
<223> OTHER INFORMATION: Xaa is a basic residue
<220> FEATURE:
<221> NAME/KEY: MISC_FEATURE
<222> LOCATION: (144)..(144)
<223> OTHER INFORMATION: Xaa is a non-polar residue
<220> FEATURE:
<221> NAME/KEY: MISC_FEATURE
<222> LOCATION: (145)..(145)
<223> OTHER INFORMATION: Xaa is an aromatic residue
<220> FEATURE:
<221> NAME/KEY: MISC_FEATURE
<222> LOCATION: (147)..(147)
<223> OTHER INFORMATION: Xaa is a non-polar or aliphatic residue
<220> FEATURE:
<221> NAME/KEY: MISC_FEATURE
<222> LOCATION: (149)..(149)
<223> OTHER INFORMATION: Xaa is a polar residue
<220> FEATURE:
<221> NAME/KEY: MISC_FEATURE
<222> LOCATION: (150)..(150)
<223> OTHER INFORMATION: Xaa is an aromatic or acidic residue
<220> FEATURE:
<221> NAME/KEY: MISC_FEATURE
<222> LOCATION: (153)..(153)
<223> OTHER INFORMATION: Xaa is a polar or aromatic residue
<220> FEATURE:
<221> NAME/KEY: MISC_FEATURE
<222> LOCATION: (157)..(157)
<223> OTHER INFORMATION: Xaa is a non-polar residue
<220> FEATURE:
<221> NAME/KEY: MISC_FEATURE
<222> LOCATION: (158)..(158)
<223> OTHER INFORMATION: Xaa is a non-polar or aliphatic residue
<220> FEATURE:
<221> NAME/KEY: MISC_FEATURE
<222> LOCATION: (173)..(173)
<223> OTHER INFORMATION: Xaa is a non-polar or aliphatic residue
<220> FEATURE:
<221> NAME/KEY: MISC_FEATURE
<222> LOCATION: (175)..(175)
<223> OTHER INFORMATION: Xaa is a polar residue
<220> FEATURE:
<221> NAME/KEY: MISC_FEATURE
<222> LOCATION: (190)..(190)
<223> OTHER INFORMATION: Xaa is a polar, aliphatic, aromatic, or
      non-polar residue
<220> FEATURE:
<221> NAME/KEY: MISC_FEATURE
<222> LOCATION: (195)..(195)
<223> OTHER INFORMATION: Xaa is a non-polar residue
<220> FEATURE:
<221> NAME/KEY: MISC_FEATURE
<222> LOCATION: (196)..(196)
<223> OTHER INFORMATION: Xaa is a polar, basic, non-polar, aromatic, or
      aliphatic residue
<220> FEATURE:
<221> NAME/KEY: MISC_FEATURE
<222> LOCATION: (197)..(197)
<223> OTHER INFORMATION: Xaa is an aromatic residue
<220> FEATURE:
<221> NAME/KEY: MISC_FEATURE
<222> LOCATION: (198)..(198)
<223> OTHER INFORMATION: Xaa is a polar or non-polar residue
<220> FEATURE:
<221> NAME/KEY: MISC_FEATURE
<222> LOCATION: (199)..(199)
<223> OTHER INFORMATION: Xaa is an acidic residue
<220> FEATURE:
<221> NAME/KEY: MISC_FEATURE
<222> LOCATION: (201)..(201)
<223> OTHER INFORMATION: Xaa is a polar residue
<220> FEATURE:
<221> NAME/KEY: MISC_FEATURE
<222> LOCATION: (202)..(202)
<223> OTHER INFORMATION: Xaa is a aromatic or basic residue
<220> FEATURE:
<221> NAME/KEY: MISC_FEATURE
<222> LOCATION: (203)..(203)
<223> OTHER INFORMATION: Xaa is a non-polar, aromatic, aliphatic residue
```

```
<220> FEATURE:
<221> NAME/KEY: MISC_FEATURE
<222> LOCATION: (205)..(205)
<223> OTHER INFORMATION: Xaa is a polar residue
<220> FEATURE:
<221> NAME/KEY: MISC_FEATURE
<222> LOCATION: (206)..(206)
<223> OTHER INFORMATION: Xaa is an aromatic residue
<220> FEATURE:
<221> NAME/KEY: MISC_FEATURE
<222> LOCATION: (207)..(207)
<223> OTHER INFORMATION: Xaa is a non-polar, aromatic, acidic, or
      aliphatic residue
<220> FEATURE:
<221> NAME/KEY: MISC_FEATURE
<222> LOCATION: (209)..(209)
<223> OTHER INFORMATION: Xaa is an aromatic, acidic, non-polar, polar,
      or aliphatic residue
<220> FEATURE:
<221> NAME/KEY: MISC_FEATURE
<222> LOCATION: (210)..(210)
<223> OTHER INFORMATION: Xaa is a non-polar or aliphatic residue
<220> FEATURE:
<221> NAME/KEY: MISC_FEATURE
<222> LOCATION: (211)..(211)
<223> OTHER INFORMATION: Xaa is an aromatic, acidic, aliphatic, polar,
      or non-polar residue
<220> FEATURE:
<221> NAME/KEY: MISC_FEATURE
<222> LOCATION: (212)..(212)
<223> OTHER INFORMATION: Xaa is a non-polar, aliphatic, acidic, basic,
      or aromatic residue
<220> FEATURE:
<221> NAME/KEY: MISC_FEATURE
<222> LOCATION: (213)..(213)
<223> OTHER INFORMATION: Xaa is an aromatic, basic, acidic, polar,
      non-polar, or aliphatic residue
<220> FEATURE:
<221> NAME/KEY: MISC_FEATURE
<222> LOCATION: (217)..(217)
<223> OTHER INFORMATION: Xaa is a polar or aromatic residue
<220> FEATURE:
<221> NAME/KEY: MISC_FEATURE
<222> LOCATION: (226)..(226)
<223> OTHER INFORMATION: Xaa is an aliphatic residue
<220> FEATURE:
<221> NAME/KEY: MISC_FEATURE
<222> LOCATION: (233)..(233)
<223> OTHER INFORMATION: Xaa is a polar residue
<220> FEATURE:
<221> NAME/KEY: MISC_FEATURE
<222> LOCATION: (249)..(249)
<223> OTHER INFORMATION: Xaa is a non-polar or basic residue
<220> FEATURE:
<221> NAME/KEY: MISC_FEATURE
<222> LOCATION: (250)..(250)
<223> OTHER INFORMATION: Xaa is a non-polar residue
<220> FEATURE:
<221> NAME/KEY: MISC_FEATURE
<222> LOCATION: (252)..(252)
<223> OTHER INFORMATION: Xaa is an aromatic residue

<400> SEQUENCE: 239

Met Thr Asp Arg Leu Lys Gly Lys Val Ala Ile Val Thr Gly Gly Thr
1               5                   10                  15

Xaa Gly Ile Gly Leu Ala Ile Ala Asp Lys Phe Val Glu Glu Gly Ala
            20                  25                  30

Lys Val Val Ile Thr Gly Arg Xaa Ala Asp Val Gly Glu Lys Ala Ala
        35                  40                  45

Lys Ser Ile Gly Gly Thr Asp Val Ile Arg Phe Val Gln His Asp Xaa
    50                  55                  60

Ser Asp Glu Xaa Gly Trp Xaa Lys Leu Phe Asp Thr Thr Glu Glu Ala
65                  70                  75                  80
```

```
Phe Gly Pro Val Thr Thr Val Val Asn Asn Ala Gly Ile Xaa Val Xaa
                    85                  90                  95

Lys Ser Val Glu Asp Xaa Thr Thr Glu Glu Trp Arg Lys Xaa Leu Ser
            100                 105                 110

Val Xaa Leu Asp Gly Val Phe Phe Gly Thr Arg Leu Gly Ile Gln Arg
        115                 120                 125

Met Lys Asn Lys Gly Leu Xaa Ala Ser Ile Ile Asn Met Ser Ser Xaa
    130                 135                 140

Xaa Gly Xaa Val Xaa Xaa Pro Thr Xaa Gly Ala Tyr Xaa Xaa Ser Lys
145                 150                 155                 160

Gly Ala Val Arg Ile Met Ser Lys Ser Ala Ala Leu Xaa Cys Xaa Leu
                165                 170                 175

Lys Asp Tyr Asp Val Arg Val Asn Thr Val His Pro Gly Xaa Ile Lys
            180                 185                 190

Thr Pro Xaa Xaa Xaa Xaa Xaa Glu Xaa Xaa Xaa Glu Xaa Xaa Xaa Gln
        195                 200                 205

Xaa Xaa Xaa Xaa Xaa Met Gly His Xaa Gly Pro Asn Asp Ile Ala
    210                 215                 220

Trp Xaa Cys Val Tyr Leu Ala Ser Xaa Glu Ser Lys Phe Ala Thr Gly
225                 230                 235                 240

Ala Glu Phe Val Val Asp Gly Gly Xaa Xaa Ala Xaa
                245                 250

<210> SEQ ID NO 240
<211> LENGTH: 252
<212> TYPE: PRT
<213> ORGANISM: Artificial Sequences
<220> FEATURE:
<223> OTHER INFORMATION: Synthetic engineered aldo-keto reductase
      variant
<220> FEATURE:
<221> NAME/KEY: MISC_FEATURE
<222> LOCATION: (17)..(17)
<223> OTHER INFORMATION: Xaa is a polar or aliphatic residue
<220> FEATURE:
<221> NAME/KEY: MISC_FEATURE
<222> LOCATION: (40)..(40)
<223> OTHER INFORMATION: Xaa is a basic or aromatic residue
<220> FEATURE:
<221> NAME/KEY: MISC_FEATURE
<222> LOCATION: (64)..(64)
<223> OTHER INFORMATION: Xaa is an aliphatic residue
<220> FEATURE:
<221> NAME/KEY: MISC_FEATURE
<222> LOCATION: (68)..(68)
<223> OTHER INFORMATION: Xaa is a non-polar or aliphatic residue
<220> FEATURE:
<221> NAME/KEY: MISC_FEATURE
<222> LOCATION: (71)..(71)
<223> OTHER INFORMATION: Xaa is a non-polar or polar residue
<220> FEATURE:
<221> NAME/KEY: MISC_FEATURE
<222> LOCATION: (94)..(94)
<223> OTHER INFORMATION: Xaa is a polar, aliphatic, or non-polar residue
<220> FEATURE:
<221> NAME/KEY: MISC_FEATURE
<222> LOCATION: (96)..(96)
<223> OTHER INFORMATION: Xaa is an aliphatic or polar residue
<220> FEATURE:
<221> NAME/KEY: MISC_FEATURE
<222> LOCATION: (102)..(102)
<223> OTHER INFORMATION: Xaa is an acidic or polar residue
<220> FEATURE:
<221> NAME/KEY: MISC_FEATURE
<222> LOCATION: (110)..(110)
<223> OTHER INFORMATION: Xaa is an aliphatic, acidic, or aromatic
      residue
<220> FEATURE:
```

```
<221> NAME/KEY: MISC_FEATURE
<222> LOCATION: (114)..(114)
<223> OTHER INFORMATION: Xaa is a polar or non-polar residue
<220> FEATURE:
<221> NAME/KEY: MISC_FEATURE
<222> LOCATION: (135)..(135)
<223> OTHER INFORMATION: Xaa is a non-polar or basic residue
<220> FEATURE:
<221> NAME/KEY: MISC_FEATURE
<222> LOCATION: (144)..(144)
<223> OTHER INFORMATION: Xaa is an aliphatic or non-polar residue
<220> FEATURE:
<221> NAME/KEY: MISC_FEATURE
<222> LOCATION: (145)..(145)
<223> OTHER INFORMATION: Xaa is an acidic or aromatic residue
<220> FEATURE:
<221> NAME/KEY: MISC_FEATURE
<222> LOCATION: (147)..(147)
<223> OTHER INFORMATION: Xaa is an aromatic, non-polar, or aliphatic
      residue
<220> FEATURE:
<221> NAME/KEY: MISC_FEATURE
<222> LOCATION: (149)..(149)
<223> OTHER INFORMATION: Xaa is a non-polar or polar residue
<220> FEATURE:
<221> NAME/KEY: MISC_FEATURE
<222> LOCATION: (150)..(150)
<223> OTHER INFORMATION: Xaa is an aromatic or acidic residue
<220> FEATURE:
<221> NAME/KEY: MISC_FEATURE
<222> LOCATION: (153)..(153)
<223> OTHER INFORMATION: Xaa is an aliphatic, polar or aromatic residue
<220> FEATURE:
<221> NAME/KEY: MISC_FEATURE
<222> LOCATION: (157)..(157)
<223> OTHER INFORMATION: Xaa is a non-polar or polar residue
<220> FEATURE:
<221> NAME/KEY: MISC_FEATURE
<222> LOCATION: (158)..(158)
<223> OTHER INFORMATION: Xaa is a non-polar or aliphatic residue
<220> FEATURE:
<221> NAME/KEY: MISC_FEATURE
<222> LOCATION: (173)..(173)
<223> OTHER INFORMATION: Xaa is an acidic, non-polar, or aliphatic
      residue
<220> FEATURE:
<221> NAME/KEY: MISC_FEATURE
<222> LOCATION: (175)..(175)
<223> OTHER INFORMATION: Xaa is an aliphatic or polar residue
<220> FEATURE:
<221> NAME/KEY: MISC_FEATURE
<222> LOCATION: (190)..(190)
<223> OTHER INFORMATION: Xaa is a polar, aliphatic, aromatic, or
      non-polar residue
<220> FEATURE:
<221> NAME/KEY: MISC_FEATURE
<222> LOCATION: (195)..(195)
<223> OTHER INFORMATION: Xaa is a non-polar or aliphatic residue
<220> FEATURE:
<221> NAME/KEY: MISC_FEATURE
<222> LOCATION: (196)..(196)
<223> OTHER INFORMATION: Xaa is a polar, basic, non-polar, aromatic, or
      aliphatic residue
<220> FEATURE:
<221> NAME/KEY: MISC_FEATURE
<222> LOCATION: (197)..(197)
<223> OTHER INFORMATION: Xaa is an acidic or aromatic residue
<220> FEATURE:
<221> NAME/KEY: MISC_FEATURE
<222> LOCATION: (198)..(198)
<223> OTHER INFORMATION: Xaa is an acidic, polar, or non-polar residue
<220> FEATURE:
<221> NAME/KEY: MISC_FEATURE
<222> LOCATION: (199)..(199)
<223> OTHER INFORMATION: Xaa is an aliphatic or acidic residue
<220> FEATURE:
<221> NAME/KEY: MISC_FEATURE
<222> LOCATION: (201)..(201)
<223> OTHER INFORMATION: Xaa is a non-polar or polar residue
```

```
<220> FEATURE:
<221> NAME/KEY: MISC_FEATURE
<222> LOCATION: (202)..(202)
<223> OTHER INFORMATION: Xaa is an aliphatic, aromatic, or basic residue
<220> FEATURE:
<221> NAME/KEY: MISC_FEATURE
<222> LOCATION: (203)..(203)
<223> OTHER INFORMATION: Xaa is an acidic, non-polar, aromatic, or
      aliphatic residue
<220> FEATURE:
<221> NAME/KEY: MISC_FEATURE
<222> LOCATION: (205)..(205)
<223> OTHER INFORMATION: Xaa is a non-polar or polar residue
<220> FEATURE:
<221> NAME/KEY: MISC_FEATURE
<222> LOCATION: (206)..(206)
<223> OTHER INFORMATION: Xaa is a non-polar or aromatic residue
<220> FEATURE:
<221> NAME/KEY: MISC_FEATURE
<222> LOCATION: (207)..(207)
<223> OTHER INFORMATION: Xaa is a polar, non-polar, aromatic, acidic, or
      aliphatic residue
<220> FEATURE:
<221> NAME/KEY: MISC_FEATURE
<222> LOCATION: (209)..(209)
<223> OTHER INFORMATION: Xaa is a basic, aromatic, acidic, non-polar,
      polar, or aliphatic residue
<220> FEATURE:
<221> NAME/KEY: MISC_FEATURE
<222> LOCATION: (210)..(210)
<223> OTHER INFORMATION: Xaa is a polar, non-polar, or aliphatic residue
<220> FEATURE:
<221> NAME/KEY: MISC_FEATURE
<222> LOCATION: (211)..(211)
<223> OTHER INFORMATION: Xaa is a basic, aromatic, acidic, aliphatic,
      polar, or non-polar residue
<220> FEATURE:
<221> NAME/KEY: MISC_FEATURE
<222> LOCATION: (212)..(212)
<223> OTHER INFORMATION: Xaa is a polar, non-polar, aliphatic, acidic,
      basic, or aromatic residue
<220> FEATURE:
<221> NAME/KEY: MISC_FEATURE
<222> LOCATION: (213)..(213)
<223> OTHER INFORMATION: Xaa is an aromatic, basic, acidic, polar,
      non-polar, or aliphatic residue
<220> FEATURE:
<221> NAME/KEY: MISC_FEATURE
<222> LOCATION: (217)..(217)
<223> OTHER INFORMATION: Xaa is an aliphatic, polar, or aromatic residue
<220> FEATURE:
<221> NAME/KEY: MISC_FEATURE
<222> LOCATION: (226)..(226)
<223> OTHER INFORMATION: Xaa is an aliphatic residue
<220> FEATURE:
<221> NAME/KEY: MISC_FEATURE
<222> LOCATION: (233)..(233)
<223> OTHER INFORMATION: Xaa is an acidic or polar residue
<220> FEATURE:
<221> NAME/KEY: MISC_FEATURE
<222> LOCATION: (249)..(249)
<223> OTHER INFORMATION: Xaa is an aromatic, non-polar, or basic residue
<220> FEATURE:
<221> NAME/KEY: MISC_FEATURE
<222> LOCATION: (250)..(250)
<223> OTHER INFORMATION: Xaa is a polar or non-polar residue
<220> FEATURE:
<221> NAME/KEY: MISC_FEATURE
<222> LOCATION: (252)..(252)
<223> OTHER INFORMATION: Xaa is a polar or aromatic residue

<400> SEQUENCE: 240

Met Thr Asp Arg Leu Lys Gly Lys Val Ala Ile Val Thr Gly Gly Thr
1               5                   10                  15

Xaa Gly Ile Gly Leu Ala Ile Ala Asp Lys Phe Val Glu Glu Gly Ala
            20                  25                  30
```

```
Lys Val Val Ile Thr Gly Arg Xaa Ala Asp Val Gly Glu Lys Ala Ala
                35                  40                  45

Lys Ser Ile Gly Gly Thr Asp Val Ile Arg Phe Val Gln His Asp Xaa
 50                  55                  60

Ser Asp Glu Xaa Gly Trp Xaa Lys Leu Phe Asp Thr Thr Glu Glu Ala
 65                  70                  75                  80

Phe Gly Pro Val Thr Thr Val Asn Asn Ala Gly Ile Xaa Val Xaa
                85                  90                  95

Lys Ser Val Glu Asp Xaa Thr Thr Glu Glu Trp Arg Lys Xaa Leu Ser
                100                 105                 110

Val Xaa Leu Asp Gly Val Phe Phe Gly Thr Arg Leu Gly Ile Gln Arg
    115                 120                 125

Met Lys Asn Lys Gly Leu Xaa Ala Ser Ile Ile Asn Met Ser Ser Xaa
130                 135                 140

Xaa Gly Xaa Val Xaa Xaa Pro Thr Xaa Gly Ala Tyr Xaa Xaa Ser Lys
145                 150                 155                 160

Gly Ala Val Arg Ile Met Ser Lys Ser Ala Ala Leu Xaa Cys Xaa Leu
                165                 170                 175

Lys Asp Tyr Asp Val Arg Val Asn Thr Val His Pro Gly Xaa Ile Lys
                180                 185                 190

Thr Pro Xaa Xaa Xaa Xaa Xaa Glu Xaa Xaa Xaa Glu Xaa Xaa Xaa Gln
            195                 200                 205

Xaa Xaa Xaa Xaa Xaa Met Gly His Xaa Gly Glu Pro Asn Asp Ile Ala
210                 215                 220

Trp Xaa Cys Val Tyr Leu Ala Ser Xaa Glu Ser Lys Phe Ala Thr Gly
225                 230                 235                 240

Ala Glu Phe Val Val Asp Gly Gly Xaa Xaa Ala Xaa
                245                 250

<210> SEQ ID NO 241
<211> LENGTH: 252
<212> TYPE: PRT
<213> ORGANISM: Artificial Sequence
<220> FEATURE:
<223> OTHER INFORMATION: Synthetic engineered aldo-keto reductase
      variant
<220> FEATURE:
<221> NAME/KEY: MISC_FEATURE
<222> LOCATION: (17)..(17)
<223> OTHER INFORMATION: Xaa is a polar or aliphatic residue
<220> FEATURE:
<221> NAME/KEY: MISC_FEATURE
<222> LOCATION: (40)..(40)
<223> OTHER INFORMATION: Xaa is a basic or aromatic residue
<220> FEATURE:
<221> NAME/KEY: MISC_FEATURE
<222> LOCATION: (64)..(64)
<223> OTHER INFORMATION: Xaa is an aliphatic residue
<220> FEATURE:
<221> NAME/KEY: MISC_FEATURE
<222> LOCATION: (68)..(68)
<223> OTHER INFORMATION: Xaa is a non-polar or aliphatic residue
<220> FEATURE:
<221> NAME/KEY: MISC_FEATURE
<222> LOCATION: (71)..(71)
<223> OTHER INFORMATION: Xaa is a non-polar or polar residue
<220> FEATURE:
<221> NAME/KEY: MISC_FEATURE
<222> LOCATION: (94)..(94)
<223> OTHER INFORMATION: Xaa is a polar, aliphatic, or non-polar residue
<220> FEATURE:
<221> NAME/KEY: MISC_FEATURE
<222> LOCATION: (96)..(96)
<223> OTHER INFORMATION: Xaa is an aliphatic or polar residue
<220> FEATURE:
```

```
<221> NAME/KEY: MISC_FEATURE
<222> LOCATION: (102)..(102)
<223> OTHER INFORMATION: Xaa is an acidic or polar residue
<220> FEATURE:
<221> NAME/KEY: MISC_FEATURE
<222> LOCATION: (110)..(110)
<223> OTHER INFORMATION: Xaa is an aliphatic, acidic, or aromatic
      residue
<220> FEATURE:
<221> NAME/KEY: MISC_FEATURE
<222> LOCATION: (114)..(114)
<223> OTHER INFORMATION: Xaa is a polar or non-polar residue
<220> FEATURE:
<221> NAME/KEY: MISC_FEATURE
<222> LOCATION: (135)..(135)
<223> OTHER INFORMATION: Xaa is a non-polar or basic residue
<220> FEATURE:
<221> NAME/KEY: MISC_FEATURE
<222> LOCATION: (144)..(144)
<223> OTHER INFORMATION: Xaa is an aliphatic or non-polar residue
<220> FEATURE:
<221> NAME/KEY: MISC_FEATURE
<222> LOCATION: (145)..(145)
<223> OTHER INFORMATION: Xaa is an acidic or aromatic residue
<220> FEATURE:
<221> NAME/KEY: MISC_FEATURE
<222> LOCATION: (147)..(147)
<223> OTHER INFORMATION: Xaa is an aromatic, non-polar, or aliphatic
      residue
<220> FEATURE:
<221> NAME/KEY: MISC_FEATURE
<222> LOCATION: (149)..(149)
<223> OTHER INFORMATION: Xaa is a non-polar or polar residue
<220> FEATURE:
<221> NAME/KEY: MISC_FEATURE
<222> LOCATION: (150)..(150)
<223> OTHER INFORMATION: Xaa is an aromatic or acidic residue
<220> FEATURE:
<221> NAME/KEY: MISC_FEATURE
<222> LOCATION: (153)..(153)
<223> OTHER INFORMATION: Xaa is an aliphatic, polar, or aromatic residue
<220> FEATURE:
<221> NAME/KEY: MISC_FEATURE
<222> LOCATION: (157)..(157)
<223> OTHER INFORMATION: Xaa is a non-polar or polar residue
<220> FEATURE:
<221> NAME/KEY: MISC_FEATURE
<222> LOCATION: (158)..(158)
<223> OTHER INFORMATION: Xaa is a non-polar or aliphatic residue
<220> FEATURE:
<221> NAME/KEY: MISC_FEATURE
<222> LOCATION: (175)..(175)
<223> OTHER INFORMATION: Xaa is an aliphatic or polar residue
<220> FEATURE:
<221> NAME/KEY: MISC_FEATURE
<222> LOCATION: (190)..(190)
<223> OTHER INFORMATION: Xaa is a polar, aliphatic, aromatic, or
      non-polar residue
<220> FEATURE:
<221> NAME/KEY: MISC_FEATURE
<222> LOCATION: (195)..(195)
<223> OTHER INFORMATION: Xaa is a non-polar or aliphatic residue
<220> FEATURE:
<221> NAME/KEY: MISC_FEATURE
<222> LOCATION: (196)..(196)
<223> OTHER INFORMATION: Xaa is a polar, basic, non-polar, aromatic, or
      aliphatic residue
<220> FEATURE:
<221> NAME/KEY: MISC_FEATURE
<222> LOCATION: (197)..(197)
<223> OTHER INFORMATION: Xaa is an acidic or aromatic residue
<220> FEATURE:
<221> NAME/KEY: MISC_FEATURE
<222> LOCATION: (198)..(198)
<223> OTHER INFORMATION: Xaa is an acidic, polar, or non-polar residue
<220> FEATURE:
<221> NAME/KEY: MISC_FEATURE
<222> LOCATION: (199)..(199)
<223> OTHER INFORMATION: Xaa is an aliphatic or acidic residue
```

```
<220> FEATURE:
<221> NAME/KEY: MISC_FEATURE
<222> LOCATION: (201)..(201)
<223> OTHER INFORMATION: Xaa is a non-polar or polar residue
<220> FEATURE:
<221> NAME/KEY: MISC_FEATURE
<222> LOCATION: (202)..(202)
<223> OTHER INFORMATION: Xaa is an aliphatic, aromatic, or basic residue
<220> FEATURE:
<221> NAME/KEY: MISC_FEATURE
<222> LOCATION: (203)..(203)
<223> OTHER INFORMATION: Xaa is an acidic, non-polar, aromatic, or
      aliphatic residue
<220> FEATURE:
<221> NAME/KEY: MISC_FEATURE
<222> LOCATION: (205)..(205)
<223> OTHER INFORMATION: Xaa is a non-polar or polar residue
<220> FEATURE:
<221> NAME/KEY: MISC_FEATURE
<222> LOCATION: (206)..(206)
<223> OTHER INFORMATION: Xaa is a non-polar or aromatic residue
<220> FEATURE:
<221> NAME/KEY: MISC_FEATURE
<222> LOCATION: (207)..(207)
<223> OTHER INFORMATION: Xaa is a polar, non-polar, aromatic, acidic, or
      aliphatic residue
<220> FEATURE:
<221> NAME/KEY: MISC_FEATURE
<222> LOCATION: (209)..(209)
<223> OTHER INFORMATION: Xaa is a basic, aromatic, acidic, non-polar,
      polar, or aliphatic residue
<220> FEATURE:
<221> NAME/KEY: MISC_FEATURE
<222> LOCATION: (210)..(210)
<223> OTHER INFORMATION: Xaa is a polar, non-polar, or aliphatic residue
<220> FEATURE:
<221> NAME/KEY: MISC_FEATURE
<222> LOCATION: (211)..(211)
<223> OTHER INFORMATION: Xaa is a basic, aromatic, acidic, aliphatic,
      polar, or non-polar residue
<220> FEATURE:
<221> NAME/KEY: MISC_FEATURE
<222> LOCATION: (212)..(212)
<223> OTHER INFORMATION: Xaa is a polar, non-polar, aliphatic, acidic,
      basic, or aromatic residue
<220> FEATURE:
<221> NAME/KEY: MISC_FEATURE
<222> LOCATION: (213)..(213)
<223> OTHER INFORMATION: Xaa is an aromatic, basic, acidic, polar,
      non-polar, or aliphatic residue
<220> FEATURE:
<221> NAME/KEY: MISC_FEATURE
<222> LOCATION: (217)..(217)
<223> OTHER INFORMATION: Xaa is an aliphatic, polar, or aromatic residue
<220> FEATURE:
<221> NAME/KEY: MISC_FEATURE
<222> LOCATION: (226)..(226)
<223> OTHER INFORMATION: Xaa is an aliphatic residue
<220> FEATURE:
<221> NAME/KEY: MISC_FEATURE
<222> LOCATION: (233)..(233)
<223> OTHER INFORMATION: Xaa is an acidic or polar residue
<220> FEATURE:
<221> NAME/KEY: MISC_FEATURE
<222> LOCATION: (249)..(249)
<223> OTHER INFORMATION: Xaa is an aromatic, non-polar, or basic residue
<220> FEATURE:
<221> NAME/KEY: MISC_FEATURE
<222> LOCATION: (250)..(250)
<223> OTHER INFORMATION: Xaa is a polar or non-polar residue
<220> FEATURE:
<221> NAME/KEY: MISC_FEATURE
<222> LOCATION: (252)..(252)
<223> OTHER INFORMATION: Xaa is a polar or aromatic residue

<400> SEQUENCE: 241

Met Thr Asp Arg Leu Lys Gly Lys Val Ala Ile Val Thr Gly Gly Thr
1               5                   10                  15
```

```
Xaa Gly Ile Gly Leu Ala Ile Ala Asp Lys Phe Val Glu Glu Gly Ala
            20                  25                  30

Lys Val Val Ile Thr Gly Arg Xaa Ala Asp Val Gly Glu Lys Ala Ala
        35                  40                  45

Lys Ser Ile Gly Gly Thr Asp Val Ile Arg Phe Val Gln His Asp Xaa
    50                  55                  60

Ser Asp Glu Xaa Gly Trp Xaa Lys Leu Phe Asp Thr Thr Glu Ala
65                  70                  75                  80

Phe Gly Pro Val Thr Thr Val Asn Asn Ala Gly Ile Xaa Val Xaa
                85                  90                  95

Lys Ser Val Glu Asp Xaa Thr Thr Glu Glu Trp Arg Lys Xaa Leu Ser
            100                 105                 110

Val Xaa Leu Asp Gly Val Phe Phe Gly Thr Arg Leu Gly Ile Gln Arg
        115                 120                 125

Met Lys Asn Lys Gly Leu Xaa Ala Ser Ile Ile Asn Met Ser Ser Xaa
    130                 135                 140

Xaa Gly Xaa Val Xaa Xaa Pro Thr Xaa Gly Ala Tyr Xaa Xaa Ser Lys
145                 150                 155                 160

Gly Ala Val Arg Ile Met Ser Lys Ser Ala Ala Leu Leu Cys Xaa Leu
                165                 170                 175

Lys Asp Tyr Asp Val Arg Val Asn Thr Val His Pro Gly Xaa Ile Lys
            180                 185                 190

Thr Pro Xaa Xaa Xaa Xaa Xaa Glu Xaa Xaa Xaa Glu Xaa Xaa Xaa Gln
        195                 200                 205

Xaa Xaa Xaa Xaa Xaa Met Gly His Xaa Gly Glu Pro Asn Asp Ile Ala
210                 215                 220

Trp Xaa Cys Val Tyr Leu Ala Ser Xaa Glu Ser Lys Phe Ala Thr Gly
225                 230                 235                 240

Ala Glu Phe Val Val Asp Gly Gly Xaa Xaa Ala Xaa
                245                 250

<210> SEQ ID NO 242
<211> LENGTH: 252
<212> TYPE: PRT
<213> ORGANISM: Artificial Sequence
<220> FEATURE:
<223> OTHER INFORMATION: Synthetic engineered aldo-reductase variant
<220> FEATURE:
<221> NAME/KEY: MISC_FEATURE
<222> LOCATION: (17)..(17)
<223> OTHER INFORMATION: Xaa is a polar or aliphatic residue
<220> FEATURE:
<221> NAME/KEY: MISC_FEATURE
<222> LOCATION: (40)..(40)
<223> OTHER INFORMATION: Xaa is a basic or aromatic residue
<220> FEATURE:
<221> NAME/KEY: MISC_FEATURE
<222> LOCATION: (64)..(64)
<223> OTHER INFORMATION: Xaa is an aliphatic residue
<220> FEATURE:
<221> NAME/KEY: MISC_FEATURE
<222> LOCATION: (68)..(68)
<223> OTHER INFORMATION: Xaa is a non-polar or aliphatic residue
<220> FEATURE:
<221> NAME/KEY: MISC_FEATURE
<222> LOCATION: (71)..(71)
<223> OTHER INFORMATION: Xaa is a non-polar or polar residue
<220> FEATURE:
<221> NAME/KEY: MISC_FEATURE
<222> LOCATION: (94)..(94)
<223> OTHER INFORMATION: Xaa is a polar, aliphatic, or non-polar residue
<220> FEATURE:
<221> NAME/KEY: MISC_FEATURE
```

```
<222> LOCATION: (96)..(96)
<223> OTHER INFORMATION: Xaa is an aliphatic or polar residue
<220> FEATURE:
<221> NAME/KEY: MISC_FEATURE
<222> LOCATION: (102)..(102)
<223> OTHER INFORMATION: Xaa is an acidic or polar residue
<220> FEATURE:
<221> NAME/KEY: MISC_FEATURE
<222> LOCATION: (110)..(110)
<223> OTHER INFORMATION: Xaa is an aliphatic, acidic, or aromatic
      residue
<220> FEATURE:
<221> NAME/KEY: MISC_FEATURE
<222> LOCATION: (114)..(114)
<223> OTHER INFORMATION: Xaa is a polar or non-polar residue
<220> FEATURE:
<221> NAME/KEY: MISC_FEATURE
<222> LOCATION: (135)..(135)
<223> OTHER INFORMATION: Xaa is a non-polar or basic residue
<220> FEATURE:
<221> NAME/KEY: MISC_FEATURE
<222> LOCATION: (144)..(144)
<223> OTHER INFORMATION: Xaa is an aliphatic or non-polar residue
<220> FEATURE:
<221> NAME/KEY: MISC_FEATURE
<222> LOCATION: (145)..(145)
<223> OTHER INFORMATION: Xaa is an acidic or aromatic residue
<220> FEATURE:
<221> NAME/KEY: MISC_FEATURE
<222> LOCATION: (147)..(147)
<223> OTHER INFORMATION: Xaa is an aromatic, non-polar, or aliphatic
      residue
<220> FEATURE:
<221> NAME/KEY: MISC_FEATURE
<222> LOCATION: (149)..(149)
<223> OTHER INFORMATION: Xaa is a non-polar or polar residue
<220> FEATURE:
<221> NAME/KEY: MISC_FEATURE
<222> LOCATION: (150)..(150)
<223> OTHER INFORMATION: Xaa is an aromatic or acidic residue
<220> FEATURE:
<221> NAME/KEY: MISC_FEATURE
<222> LOCATION: (153)..(153)
<223> OTHER INFORMATION: Xaa is an aliphatic, polar or aromatic residue
<220> FEATURE:
<221> NAME/KEY: MISC_FEATURE
<222> LOCATION: (157)..(157)
<223> OTHER INFORMATION: Xaa is a non-polar or polar residue
<220> FEATURE:
<221> NAME/KEY: MISC_FEATURE
<222> LOCATION: (158)..(158)
<223> OTHER INFORMATION: Xaa is a non-polar or aliphatic residue
<220> FEATURE:
<221> NAME/KEY: MISC_FEATURE
<222> LOCATION: (173)..(173)
<223> OTHER INFORMATION: Xaa is an acidic, non-polar, or aliphatic
      residue
<220> FEATURE:
<221> NAME/KEY: MISC_FEATURE
<222> LOCATION: (175)..(175)
<223> OTHER INFORMATION: Xaa is an aliphatic or polar residue
<220> FEATURE:
<221> NAME/KEY: MISC_FEATURE
<222> LOCATION: (190)..(190)
<223> OTHER INFORMATION: Xaa is a polar, aliphatic, aromatic, or
      non-polar residue
<220> FEATURE:
<221> NAME/KEY: MISC_FEATURE
<222> LOCATION: (195)..(195)
<223> OTHER INFORMATION: Xaa is a non-polar or aliphatic residue
<220> FEATURE:
<221> NAME/KEY: MISC_FEATURE
<222> LOCATION: (196)..(196)
<223> OTHER INFORMATION: Xaa is a polar, basic, non-polar, aromatic, or
      aliphatic residue
<220> FEATURE:
<221> NAME/KEY: MISC_FEATURE
<222> LOCATION: (197)..(197)
<223> OTHER INFORMATION: Xaa is an acidic or aromatic residue
```

-continued

```
<220> FEATURE:
<221> NAME/KEY: MISC_FEATURE
<222> LOCATION: (198)..(198)
<223> OTHER INFORMATION: Xaa is an acidic, polar, or non-polar residue
<220> FEATURE:
<221> NAME/KEY: MISC_FEATURE
<222> LOCATION: (199)..(199)
<223> OTHER INFORMATION: Xaa is an aliphatic or acidic residue
<220> FEATURE:
<221> NAME/KEY: MISC_FEATURE
<222> LOCATION: (201)..(201)
<223> OTHER INFORMATION: Xaa is a non-polar or polar residue
<220> FEATURE:
<221> NAME/KEY: MISC_FEATURE
<222> LOCATION: (202)..(202)
<223> OTHER INFORMATION: Xaa is an aliphatic, aromatic, or basic residue
<220> FEATURE:
<221> NAME/KEY: MISC_FEATURE
<222> LOCATION: (203)..(203)
<223> OTHER INFORMATION: Xaa is an acidic, non-polar, aromatic, or
      aliphatic residue
<220> FEATURE:
<221> NAME/KEY: MISC_FEATURE
<222> LOCATION: (205)..(205)
<223> OTHER INFORMATION: Xaa is a non-polar or polar residue
<220> FEATURE:
<221> NAME/KEY: MISC_FEATURE
<222> LOCATION: (206)..(206)
<223> OTHER INFORMATION: Xaa is a non-polar or aromatic residue
<220> FEATURE:
<221> NAME/KEY: MISC_FEATURE
<222> LOCATION: (207)..(207)
<223> OTHER INFORMATION: Xaa is a polar, non-polar, aromatic, acidic, or
      aliphatic residue
<220> FEATURE:
<221> NAME/KEY: MISC_FEATURE
<222> LOCATION: (209)..(209)
<223> OTHER INFORMATION: Xaa is a basic, aromatic, acidic, non-polar,
      polar, or aliphatic residue
<220> FEATURE:
<221> NAME/KEY: MISC_FEATURE
<222> LOCATION: (210)..(210)
<223> OTHER INFORMATION: Xaa is a polar, non-polar, or aliphatic residue
<220> FEATURE:
<221> NAME/KEY: MISC_FEATURE
<222> LOCATION: (211)..(211)
<223> OTHER INFORMATION: Xaa is a basic, aromatic, acidic, aliphatic,
      polar, or non-polar residue
<220> FEATURE:
<221> NAME/KEY: MISC_FEATURE
<222> LOCATION: (212)..(212)
<223> OTHER INFORMATION: Xaa is a polar, non-polar, aliphatic, acidic,
      basic, or aromatic residue
<220> FEATURE:
<221> NAME/KEY: MISC_FEATURE
<222> LOCATION: (213)..(213)
<223> OTHER INFORMATION: Xaa is an aromatic, basic, acidic, polar,
      non-polar, or aliphatic residue
<220> FEATURE:
<221> NAME/KEY: MISC_FEATURE
<222> LOCATION: (217)..(217)
<223> OTHER INFORMATION: Xaa is an aliphatic, polar, or aromatic residue
<220> FEATURE:
<221> NAME/KEY: MISC_FEATURE
<222> LOCATION: (226)..(226)
<223> OTHER INFORMATION: Xaa is an aliphatic residue
<220> FEATURE:
<221> NAME/KEY: MISC_FEATURE
<222> LOCATION: (233)..(233)
<223> OTHER INFORMATION: Xaa is an acidic or polar residue
<220> FEATURE:
<221> NAME/KEY: MISC_FEATURE
<222> LOCATION: (250)..(250)
<223> OTHER INFORMATION: Xaa is a polar or non-polar residue
<220> FEATURE:
<221> NAME/KEY: MISC_FEATURE
<222> LOCATION: (252)..(252)
<223> OTHER INFORMATION: Xaa is a polar or aromatic residue
```

```
<400> SEQUENCE: 242

Met Thr Asp Arg Leu Lys Gly Lys Val Ala Ile Val Thr Gly Thr
1               5                   10                  15

Xaa Gly Ile Gly Leu Ala Ile Ala Asp Lys Phe Val Glu Glu Gly Ala
                20                  25                  30

Lys Val Val Ile Thr Gly Arg Xaa Ala Asp Val Gly Glu Lys Ala Ala
            35                  40                  45

Lys Ser Ile Gly Gly Thr Asp Val Ile Arg Phe Val Gln His Asp Xaa
50                  55                  60

Ser Asp Glu Xaa Gly Trp Xaa Lys Leu Phe Asp Thr Thr Glu Glu Ala
65                  70                  75                  80

Phe Gly Pro Val Thr Thr Val Asn Asn Ala Gly Ile Xaa Val Xaa
                85                  90                  95

Lys Ser Val Glu Asp Xaa Thr Thr Glu Glu Trp Arg Lys Xaa Leu Ser
            100                 105                 110

Val Xaa Leu Asp Gly Val Phe Phe Gly Thr Arg Leu Gly Ile Gln Arg
    115                 120                 125

Met Lys Asn Lys Gly Leu Xaa Ala Ser Ile Ile Asn Met Ser Ser Xaa
130                 135                 140

Xaa Gly Xaa Val Xaa Xaa Pro Thr Xaa Gly Ala Tyr Xaa Xaa Ser Lys
145                 150                 155                 160

Gly Ala Val Arg Ile Met Ser Lys Ser Ala Ala Leu Xaa Cys Xaa Leu
                165                 170                 175

Lys Asp Tyr Asp Val Arg Val Asn Thr Val His Pro Gly Xaa Ile Lys
            180                 185                 190

Thr Pro Xaa Xaa Xaa Xaa Xaa Glu Xaa Xaa Xaa Glu Xaa Xaa Xaa Gln
        195                 200                 205

Xaa Xaa Xaa Xaa Xaa Met Gly His Xaa Gly Glu Pro Asn Asp Ile Ala
    210                 215                 220

Trp Xaa Cys Val Tyr Leu Ala Ser Xaa Glu Ser Lys Phe Ala Thr Gly
225                 230                 235                 240

Ala Glu Phe Val Val Asp Gly Gly Xaa Ala Xaa
                245                 250

<210> SEQ ID NO 243
<211> LENGTH: 252
<212> TYPE: PRT
<213> ORGANISM: Artificial Sequence
<220> FEATURE:
<223> OTHER INFORMATION: Synthetic engineered aldo-keto reductase
      variant
<220> FEATURE:
<221> NAME/KEY: MISC_FEATURE
<222> LOCATION: (17)..(17)
<223> OTHER INFORMATION: Xaa is a polar or aliphatic residue
<220> FEATURE:
<221> NAME/KEY: MISC_FEATURE
<222> LOCATION: (40)..(40)
<223> OTHER INFORMATION: Xaa is a basic or aromatic residue
<220> FEATURE:
<221> NAME/KEY: MISC_FEATURE
<222> LOCATION: (64)..(64)
<223> OTHER INFORMATION: Xaa is an aliphatic residue
<220> FEATURE:
<221> NAME/KEY: MISC_FEATURE
<222> LOCATION: (68)..(68)
<223> OTHER INFORMATION: Xaa is a non-polar or aliphatic residue
<220> FEATURE:
<221> NAME/KEY: MISC_FEATURE
<222> LOCATION: (71)..(71)
<223> OTHER INFORMATION: Xaa is a non-polar or polar residue
<220> FEATURE:
```

```
<221> NAME/KEY: MISC_FEATURE
<222> LOCATION: (94)..(94)
<223> OTHER INFORMATION: Xaa is a polar, aliphatic, or non-polar residue
<220> FEATURE:
<221> NAME/KEY: MISC_FEATURE
<222> LOCATION: (96)..(96)
<223> OTHER INFORMATION: Xaa is an aliphatic or polar residue
<220> FEATURE:
<221> NAME/KEY: MISC_FEATURE
<222> LOCATION: (102)..(102)
<223> OTHER INFORMATION: Xaa is an acidic or polar residue
<220> FEATURE:
<221> NAME/KEY: MISC_FEATURE
<222> LOCATION: (110)..(110)
<223> OTHER INFORMATION: Xaa is an aliphatic, acidic, or aromatic
      residue
<220> FEATURE:
<221> NAME/KEY: MISC_FEATURE
<222> LOCATION: (114)..(114)
<223> OTHER INFORMATION: Xaa is a polar or non-polar residue
<220> FEATURE:
<221> NAME/KEY: MISC_FEATURE
<222> LOCATION: (135)..(135)
<223> OTHER INFORMATION: Xaa is a non-polar or basic residue
<220> FEATURE:
<221> NAME/KEY: MISC_FEATURE
<222> LOCATION: (144)..(144)
<223> OTHER INFORMATION: Xaa is an aliphatic or non-polar residue
<220> FEATURE:
<221> NAME/KEY: MISC_FEATURE
<222> LOCATION: (145)..(145)
<223> OTHER INFORMATION: Xaa is an acidic or aromatic residue
<220> FEATURE:
<221> NAME/KEY: MISC_FEATURE
<222> LOCATION: (147)..(147)
<223> OTHER INFORMATION: Xaa is an aromatic, non-polar, or aliphatic
      residue
<220> FEATURE:
<221> NAME/KEY: MISC_FEATURE
<222> LOCATION: (149)..(149)
<223> OTHER INFORMATION: Xaa is a non-polar or polar residue
<220> FEATURE:
<221> NAME/KEY: MISC_FEATURE
<222> LOCATION: (150)..(150)
<223> OTHER INFORMATION: Xaa is an aromatic or acidic residue
<220> FEATURE:
<221> NAME/KEY: MISC_FEATURE
<222> LOCATION: (153)..(153)
<223> OTHER INFORMATION: Xaa is an aliphatic, polar, or aromatic residue
<220> FEATURE:
<221> NAME/KEY: MISC_FEATURE
<222> LOCATION: (157)..(157)
<223> OTHER INFORMATION: Xaa is a non-polar or polar residue
<220> FEATURE:
<221> NAME/KEY: MISC_FEATURE
<222> LOCATION: (158)..(158)
<223> OTHER INFORMATION: Xaa is a non-polar or aliphatic residue
<220> FEATURE:
<221> NAME/KEY: MISC_FEATURE
<222> LOCATION: (175)..(175)
<223> OTHER INFORMATION: Xaa is an aliphatic or polar residue
<220> FEATURE:
<221> NAME/KEY: MISC_FEATURE
<222> LOCATION: (190)..(190)
<223> OTHER INFORMATION: Xaa is a polar, aliphatic, aromatic, or
      non-polar residue
<220> FEATURE:
<221> NAME/KEY: MISC_FEATURE
<222> LOCATION: (195)..(195)
<223> OTHER INFORMATION: Xaa is a non-polar or aliphatic residue
<220> FEATURE:
<221> NAME/KEY: MISC_FEATURE
<222> LOCATION: (196)..(196)
<223> OTHER INFORMATION: Xaa is a polar, basic, non-polar, aromatic, or
      aliphatic residue
<220> FEATURE:
<221> NAME/KEY: MISC_FEATURE
<222> LOCATION: (197)..(197)
<223> OTHER INFORMATION: Xaa is an acidic or aromatic residue
```

-continued

```
<220> FEATURE:
<221> NAME/KEY: MISC_FEATURE
<222> LOCATION: (198)..(198)
<223> OTHER INFORMATION: Xaa is an acidic, polar, or non-polar residue
<220> FEATURE:
<221> NAME/KEY: MISC_FEATURE
<222> LOCATION: (199)..(199)
<223> OTHER INFORMATION: Xaa is an aliphatic or acidic residue
<220> FEATURE:
<221> NAME/KEY: MISC_FEATURE
<222> LOCATION: (201)..(201)
<223> OTHER INFORMATION: Xaa is a non-polar or polar residue
<220> FEATURE:
<221> NAME/KEY: MISC_FEATURE
<222> LOCATION: (202)..(202)
<223> OTHER INFORMATION: Xaa is an aliphatic, aromatic, or basic residue
<220> FEATURE:
<221> NAME/KEY: MISC_FEATURE
<222> LOCATION: (203)..(203)
<223> OTHER INFORMATION: Xaa is an acidic, non-polar, aromatic, or
      aliphatic residue
<220> FEATURE:
<221> NAME/KEY: MISC_FEATURE
<222> LOCATION: (205)..(205)
<223> OTHER INFORMATION: Xaa is a non-polar or polar residue
<220> FEATURE:
<221> NAME/KEY: MISC_FEATURE
<222> LOCATION: (206)..(206)
<223> OTHER INFORMATION: Xaa is a non-polar or aromatic residue
<220> FEATURE:
<221> NAME/KEY: MISC_FEATURE
<222> LOCATION: (207)..(207)
<223> OTHER INFORMATION: Xaa is a polar, non-polar, aromatic, acidic, or
      aliphatic residue
<220> FEATURE:
<221> NAME/KEY: MISC_FEATURE
<222> LOCATION: (209)..(209)
<223> OTHER INFORMATION: Xaa is a basic, aromatic, acidic, non-polar,
      polar, or aliphatic residue
<220> FEATURE:
<221> NAME/KEY: MISC_FEATURE
<222> LOCATION: (210)..(210)
<223> OTHER INFORMATION: Xaa is a polar, non-polar, or aliphatic residue
<220> FEATURE:
<221> NAME/KEY: MISC_FEATURE
<222> LOCATION: (211)..(211)
<223> OTHER INFORMATION: Xaa is a basic, aromatic, acidic, aliphatic,
      polar, or non-polar residue
<220> FEATURE:
<221> NAME/KEY: MISC_FEATURE
<222> LOCATION: (212)..(212)
<223> OTHER INFORMATION: Xaa is a polar, non-polar, aliphatic, acidic,
      basic, or aromatic residue
<220> FEATURE:
<221> NAME/KEY: MISC_FEATURE
<222> LOCATION: (213)..(213)
<223> OTHER INFORMATION: Xaa is an aromatic, basic, acidic, polar,
      non-polar, or aliphatic residue
<220> FEATURE:
<221> NAME/KEY: MISC_FEATURE
<222> LOCATION: (217)..(217)
<223> OTHER INFORMATION: Xaa is an aliphatic, polar, or aromatic residue
<220> FEATURE:
<221> NAME/KEY: MISC_FEATURE
<222> LOCATION: (226)..(226)
<223> OTHER INFORMATION: Xaa is an aliphatic residue
<220> FEATURE:
<221> NAME/KEY: MISC_FEATURE
<222> LOCATION: (233)..(233)
<223> OTHER INFORMATION: Xaa is an acidic or polar residue
<220> FEATURE:
<221> NAME/KEY: MISC_FEATURE
<222> LOCATION: (250)..(250)
<223> OTHER INFORMATION: Xaa is a polar or non-polar residue
<220> FEATURE:
<221> NAME/KEY: MISC_FEATURE
<222> LOCATION: (252)..(252)
<223> OTHER INFORMATION: Xaa is a polar or aromatic residue
```

-continued

```
<400> SEQUENCE: 243

Met Thr Asp Arg Leu Lys Gly Lys Val Ala Ile Val Thr Gly Thr
1               5                   10                  15

Xaa Gly Ile Gly Leu Ala Ile Ala Asp Lys Phe Val Glu Glu Gly Ala
            20                  25                  30

Lys Val Ile Thr Gly Arg Xaa Ala Asp Val Gly Glu Lys Ala Ala
        35                  40                  45

Lys Ser Ile Gly Gly Thr Asp Val Ile Arg Phe Val Gln His Asp Xaa
    50                  55                  60

Ser Asp Glu Xaa Gly Trp Xaa Lys Leu Phe Asp Thr Thr Glu Ala
65                  70                  75                  80

Phe Gly Pro Val Thr Thr Val Asn Asn Ala Gly Ile Xaa Val Xaa
                85                  90                  95

Lys Ser Val Glu Asp Xaa Thr Thr Glu Glu Trp Arg Lys Xaa Leu Ser
            100                 105                 110

Val Xaa Leu Asp Gly Val Phe Phe Gly Thr Arg Leu Gly Ile Gln Arg
        115                 120                 125

Met Lys Asn Lys Gly Leu Xaa Ala Ser Ile Ile Asn Met Ser Ser Xaa
130                 135                 140

Xaa Gly Xaa Val Xaa Xaa Pro Thr Xaa Gly Ala Tyr Xaa Xaa Ser Lys
145                 150                 155                 160

Gly Ala Val Arg Ile Met Ser Lys Ser Ala Ala Leu Leu Cys Xaa Leu
                165                 170                 175

Lys Asp Tyr Asp Val Arg Val Asn Thr Val His Pro Gly Xaa Ile Lys
            180                 185                 190

Thr Pro Xaa Xaa Xaa Xaa Xaa Glu Xaa Xaa Xaa Glu Xaa Xaa Xaa Gln
        195                 200                 205

Xaa Xaa Xaa Xaa Xaa Met Gly His Xaa Gly Glu Pro Asn Asp Ile Ala
    210                 215                 220

Trp Xaa Cys Val Tyr Leu Ala Ser Xaa Glu Ser Lys Phe Ala Thr Gly
225                 230                 235                 240

Ala Glu Phe Val Val Asp Gly Gly Xaa Ala Xaa
                245                 250

<210> SEQ ID NO 244
<211> LENGTH: 252
<212> TYPE: PRT
<213> ORGANISM: Artificial Sequence
<220> FEATURE:
<223> OTHER INFORMATION: Synthetic engineered aldo-keto reductase
      variant
<220> FEATURE:
<221> NAME/KEY: MISC_FEATURE
<222> LOCATION: (17)..(17)
<223> OTHER INFORMATION: Xaa is a polar residue
<220> FEATURE:
<221> NAME/KEY: MISC_FEATURE
<222> LOCATION: (40)..(40)
<223> OTHER INFORMATION: Xaa is a basic residue
<220> FEATURE:
<221> NAME/KEY: MISC_FEATURE
<222> LOCATION: (64)..(64)
<223> OTHER INFORMATION: Xaa is an aliphatic residue
<220> FEATURE:
<221> NAME/KEY: MISC_FEATURE
<222> LOCATION: (68)..(68)
<223> OTHER INFORMATION: Xaa is a non-polar or aliphatic residue
<220> FEATURE:
<221> NAME/KEY: MISC_FEATURE
<222> LOCATION: (71)..(71)
<223> OTHER INFORMATION: Xaa is a non-polar residue
<220> FEATURE:
```

-continued

```
<221> NAME/KEY: MISC_FEATURE
<222> LOCATION: (94)..(94)
<223> OTHER INFORMATION: Xaa is a polar, aliphatic, or non-polar residue
<220> FEATURE:
<221> NAME/KEY: MISC_FEATURE
<222> LOCATION: (96)..(96)
<223> OTHER INFORMATION: Xaa is an aliphatic residue
<220> FEATURE:
<221> NAME/KEY: MISC_FEATURE
<222> LOCATION: (102)..(102)
<223> OTHER INFORMATION: Xaa is an acidic or polar residue
<220> FEATURE:
<221> NAME/KEY: MISC_FEATURE
<222> LOCATION: (110)..(110)
<223> OTHER INFORMATION: Xaa is an acidic or aromatic residue
<220> FEATURE:
<221> NAME/KEY: MISC_FEATURE
<222> LOCATION: (114)..(114)
<223> OTHER INFORMATION: Xaa is a non-polar residue
<220> FEATURE:
<221> NAME/KEY: MISC_FEATURE
<222> LOCATION: (135)..(135)
<223> OTHER INFORMATION: Xaa is a basic residue
<220> FEATURE:
<221> NAME/KEY: MISC_FEATURE
<222> LOCATION: (144)..(144)
<223> OTHER INFORMATION: Xaa is a non-polar residue
<220> FEATURE:
<221> NAME/KEY: MISC_FEATURE
<222> LOCATION: (145)..(145)
<223> OTHER INFORMATION: Xaa is an aromatic residue
<220> FEATURE:
<221> NAME/KEY: MISC_FEATURE
<222> LOCATION: (147)..(147)
<223> OTHER INFORMATION: Xaa is a non-polar or aliphatic residue
<220> FEATURE:
<221> NAME/KEY: MISC_FEATURE
<222> LOCATION: (149)..(149)
<223> OTHER INFORMATION: Xaa is a polar residue
<220> FEATURE:
<221> NAME/KEY: MISC_FEATURE
<222> LOCATION: (150)..(150)
<223> OTHER INFORMATION: Xaa is an aromatic or acidic residue
<220> FEATURE:
<221> NAME/KEY: MISC_FEATURE
<222> LOCATION: (153)..(153)
<223> OTHER INFORMATION: Xaa is a polar or aromatic residue
<220> FEATURE:
<221> NAME/KEY: MISC_FEATURE
<222> LOCATION: (157)..(157)
<223> OTHER INFORMATION: Xaa is a non-polar residue
<220> FEATURE:
<221> NAME/KEY: MISC_FEATURE
<222> LOCATION: (158)..(158)
<223> OTHER INFORMATION: Xaa is a non-polar or aliphatic residue
<220> FEATURE:
<221> NAME/KEY: MISC_FEATURE
<222> LOCATION: (175)..(175)
<223> OTHER INFORMATION: Xaa is a polar residue
<220> FEATURE:
<221> NAME/KEY: MISC_FEATURE
<222> LOCATION: (190)..(190)
<223> OTHER INFORMATION: Xaa is a polar, aliphatic, aromatic, or
      non-polar residue
<220> FEATURE:
<221> NAME/KEY: MISC_FEATURE
<222> LOCATION: (195)..(195)
<223> OTHER INFORMATION: Xaa is a non-polar residue
<220> FEATURE:
<221> NAME/KEY: MISC_FEATURE
<222> LOCATION: (196)..(196)
<223> OTHER INFORMATION: Xaa is a polar, basic, non-polar, aromatic, or
      aliphatic residue
<220> FEATURE:
<221> NAME/KEY: MISC_FEATURE
<222> LOCATION: (197)..(197)
<223> OTHER INFORMATION: Xaa is an aromatic residue
<220> FEATURE:
<221> NAME/KEY: MISC_FEATURE
```

```
<222> LOCATION: (198)..(198)
<223> OTHER INFORMATION: Xaa is a polar or non-polar residue
<220> FEATURE:
<221> NAME/KEY: MISC_FEATURE
<222> LOCATION: (199)..(199)
<223> OTHER INFORMATION: Xaa is an acidic residue
<220> FEATURE:
<221> NAME/KEY: MISC_FEATURE
<222> LOCATION: (201)..(201)
<223> OTHER INFORMATION: Xaa is a polar residue
<220> FEATURE:
<221> NAME/KEY: MISC_FEATURE
<222> LOCATION: (202)..(202)
<223> OTHER INFORMATION: Xaa is an aromatic or basic residue
<220> FEATURE:
<221> NAME/KEY: MISC_FEATURE
<222> LOCATION: (203)..203)
<223> OTHER INFORMATION: Xaa is a non-polar, aromatic, or aliphatic
      residue
<220> FEATURE:
<221> NAME/KEY: MISC_FEATURE
<222> LOCATION: (205)..(205)
<223> OTHER INFORMATION: Xaa is a polar residue
<220> FEATURE:
<221> NAME/KEY: MISC_FEATURE
<222> LOCATION: (206)..(206)
<223> OTHER INFORMATION: Xaa is an aromatic residue
<220> FEATURE:
<221> NAME/KEY: MISC_FEATURE
<222> LOCATION: (207)..(207)
<223> OTHER INFORMATION: Xaa is a non-polar, aromatic, acidic, or
      aliphatic residue
<220> FEATURE:
<221> NAME/KEY: MISC_FEATURE
<222> LOCATION: (209)..(209)
<223> OTHER INFORMATION: Xaa is an aromatic, acidic, non-polar, polar,
      or aliphatic residue
<220> FEATURE:
<221> NAME/KEY: MISC_FEATURE
<222> LOCATION: (210)..(210)
<223> OTHER INFORMATION: Xaa is a non-polar or aliphatic residue
<220> FEATURE:
<221> NAME/KEY: MISC_FEATURE
<222> LOCATION: (211)..(211)
<223> OTHER INFORMATION: Xaa is an aromatic, acidic, aliphatic, polar,
      or non-polar residue
<220> FEATURE:
<221> NAME/KEY: MISC_FEATURE
<222> LOCATION: (212)..(212)
<223> OTHER INFORMATION: Xaa is a non-polar, aliphatic, acidic, basic,
      or aromatic residue
<220> FEATURE:
<221> NAME/KEY: MISC_FEATURE
<222> LOCATION: (213)..(213)
<223> OTHER INFORMATION: Xaa is an aromatic, basic, acidic, polar,
      non-polar, or aliphatic residue
<220> FEATURE:
<221> NAME/KEY: MISC_FEATURE
<222> LOCATION: (217)..(217)
<223> OTHER INFORMATION: Xaa is a polar or aromatic residue
<220> FEATURE:
<221> NAME/KEY: MISC_FEATURE
<222> LOCATION: (226)..(226)
<223> OTHER INFORMATION: Xaa is an aliphatic residue
<220> FEATURE:
<221> NAME/KEY: MISC_FEATURE
<222> LOCATION: (233)..(233)
<223> OTHER INFORMATION: Xaa is a polar residue
<220> FEATURE:
<221> NAME/KEY: MISC_FEATURE
<222> LOCATION: (249)..(249)
<223> OTHER INFORMATION: Xaa is a non-polar or basic residue
<220> FEATURE:
<221> NAME/KEY: MISC_FEATURE
<222> LOCATION: (250)..(250)
<223> OTHER INFORMATION: Xaa is a non-polar residue
<220> FEATURE:
<221> NAME/KEY: MISC_FEATURE
<222> LOCATION: (252)..(252)
```

<223> OTHER INFORMATION: Xaa is an aromatic residue

<400> SEQUENCE: 244

Met Thr Asp Arg Leu Lys Gly Lys Val Ala Ile Val Thr Gly Gly Thr
1               5                   10                  15
Xaa Gly Ile Gly Leu Ala Ile Ala Asp Lys Phe Val Glu Glu Gly Ala
                20                  25                  30
Lys Val Val Ile Thr Gly Arg Xaa Ala Asp Val Gly Glu Lys Ala Ala
            35                  40                  45
Lys Ser Ile Gly Gly Thr Asp Val Ile Arg Phe Val Gln His Asp Xaa
        50                  55                  60
Ser Asp Glu Xaa Gly Trp Xaa Lys Leu Phe Asp Thr Thr Glu Glu Ala
65                  70                  75                  80
Phe Gly Pro Val Thr Thr Val Val Asn Asn Ala Gly Ile Xaa Val Xaa
                85                  90                  95
Lys Ser Val Glu Asp Xaa Thr Thr Glu Glu Trp Arg Lys Xaa Leu Ser
            100                 105                 110
Val Xaa Leu Asp Gly Val Phe Phe Gly Thr Arg Leu Gly Ile Gln Arg
        115                 120                 125
Met Lys Asn Lys Gly Leu Xaa Ala Ser Ile Ile Asn Met Ser Ser Xaa
    130                 135                 140
Xaa Gly Xaa Val Xaa Xaa Pro Thr Xaa Gly Ala Tyr Xaa Xaa Ser Lys
145                 150                 155                 160
Gly Ala Val Arg Ile Met Ser Lys Ser Ala Ala Leu Leu Cys Xaa Leu
                165                 170                 175
Lys Asp Tyr Asp Val Arg Val Asn Thr Val His Pro Gly Xaa Ile Lys
            180                 185                 190
Thr Pro Xaa Xaa Xaa Xaa Xaa Glu Xaa Xaa Xaa Glu Xaa Xaa Xaa Gln
        195                 200                 205
Xaa Xaa Xaa Xaa Xaa Met Gly His Xaa Gly Glu Pro Asn Asp Ile Ala
    210                 215                 220
Trp Xaa Cys Val Tyr Leu Ala Ser Xaa Glu Ser Lys Phe Ala Thr Gly
225                 230                 235                 240
Ala Glu Phe Val Val Asp Gly Gly Xaa Xaa Ala Xaa
                245                 250

<210> SEQ ID NO 245
<211> LENGTH: 252
<212> TYPE: PRT
<213> ORGANISM: Artificial Sequence
<220> FEATURE:
<223> OTHER INFORMATION: Synthetic engineered aldo-keto reductase
      variant
<220> FEATURE:
<221> NAME/KEY: MISC_FEATURE
<222> LOCATION: (17)..(17)
<223> OTHER INFORMATION: Xaa is a polar residue
<220> FEATURE:
<221> NAME/KEY: MISC_FEATURE
<222> LOCATION: (40)..(40)
<223> OTHER INFORMATION: Xaa is a basic residue
<220> FEATURE:
<221> NAME/KEY: MISC_FEATURE
<222> LOCATION: (64)..(64)
<223> OTHER INFORMATION: Xaa is an aliphatic residue
<220> FEATURE:
<221> NAME/KEY: MISC_FEATURE
<222> LOCATION: (68)..(68)
<223> OTHER INFORMATION: Xaa is a non-polar or aliphatic residue
<220> FEATURE:
<221> NAME/KEY: MISC_FEATURE
<222> LOCATION: (71)..(71)

```
<223> OTHER INFORMATION: Xaa is a non-polar residue
<220> FEATURE:
<221> NAME/KEY: MISC_FEATURE
<222> LOCATION: (94)..(94)
<223> OTHER INFORMATION: Xaa is a polar, aliphatic, or non-polar residue
<220> FEATURE:
<221> NAME/KEY: MISC_FEATURE
<222> LOCATION: (96)..(96)
<223> OTHER INFORMATION: Xaa is an aliphatic residue
<220> FEATURE:
<221> NAME/KEY: MISC_FEATURE
<222> LOCATION: (102)..(102)
<223> OTHER INFORMATION: Xaa is an acidic or polar residue
<220> FEATURE:
<221> NAME/KEY: MISC_FEATURE
<222> LOCATION: (110)..(110)
<223> OTHER INFORMATION: Xaa is an acidic or aromatic residue
<220> FEATURE:
<221> NAME/KEY: MISC_FEATURE
<222> LOCATION: (114)..(114)
<223> OTHER INFORMATION: Xaa is a non-polar residue
<220> FEATURE:
<221> NAME/KEY: MISC_FEATURE
<222> LOCATION: (135)..(135)
<223> OTHER INFORMATION: Xaa is a basic residue
<220> FEATURE:
<221> NAME/KEY: MISC_FEATURE
<222> LOCATION: (144)..(144)
<223> OTHER INFORMATION: Xaa is a non-polar residue
<220> FEATURE:
<221> NAME/KEY: MISC_FEATURE
<222> LOCATION: (145)..(145)
<223> OTHER INFORMATION: Xaa is an aromatic residue
<220> FEATURE:
<221> NAME/KEY: MISC_FEATURE
<222> LOCATION: (147)..(147)
<223> OTHER INFORMATION: Xaa is a non-polar or aliphatic residue
<220> FEATURE:
<221> NAME/KEY: MISC_FEATURE
<222> LOCATION: (149)..(149)
<223> OTHER INFORMATION: Xaa is a polar residue
<220> FEATURE:
<221> NAME/KEY: MISC_FEATURE
<222> LOCATION: (150)..(150)
<223> OTHER INFORMATION: Xaa is an aromatic or acidic residue
<220> FEATURE:
<221> NAME/KEY: MISC_FEATURE
<222> LOCATION: (153)..(153)
<223> OTHER INFORMATION: Xaa is a polar or aromatic residue
<220> FEATURE:
<221> NAME/KEY: MISC_FEATURE
<222> LOCATION: (157)..(157)
<223> OTHER INFORMATION: Xaa is a non-polar residue
<220> FEATURE:
<221> NAME/KEY: MISC_FEATURE
<222> LOCATION: (158)..(158)
<223> OTHER INFORMATION: Xaa is a non-polar or aliphatic residue
<220> FEATURE:
<221> NAME/KEY: MISC_FEATURE
<222> LOCATION: (173)..(173)
<223> OTHER INFORMATION: Xaa is a non-polar or aliphatic residue
<220> FEATURE:
<221> NAME/KEY: MISC_FEATURE
<222> LOCATION: (175)..(175)
<223> OTHER INFORMATION: Xaa is a polar residue
<220> FEATURE:
<221> NAME/KEY: MISC_FEATURE
<222> LOCATION: (190)..(190)
<223> OTHER INFORMATION: Xaa is a polar, aliphatic, aromatic, or
      non-polar residue
<220> FEATURE:
<221> NAME/KEY: MISC_FEATURE
<222> LOCATION: (195)..(195)
<223> OTHER INFORMATION: Xaa is a non-polar residue
<220> FEATURE:
<221> NAME/KEY: MISC_FEATURE
<222> LOCATION: (196)..(196)
<223> OTHER INFORMATION: Xaa is a polar, basic, non-polar, aromatic, or
      aliphatic residue
```

```
<220> FEATURE:
<221> NAME/KEY: MISC_FEATURE
<222> LOCATION: (197)..(197)
<223> OTHER INFORMATION: Xaa is an aromatic residue
<220> FEATURE:
<221> NAME/KEY: MISC_FEATURE
<222> LOCATION: (198)..(198)
<223> OTHER INFORMATION: Xaa is a polar or non-polar residue
<220> FEATURE:
<221> NAME/KEY: MISC_FEATURE
<222> LOCATION: (199)..(199)
<223> OTHER INFORMATION: Xaa is an acidic residue
<220> FEATURE:
<221> NAME/KEY: MISC_FEATURE
<222> LOCATION: (201)..(201)
<223> OTHER INFORMATION: Xaa is a polar residue
<220> FEATURE:
<221> NAME/KEY: MISC_FEATURE
<222> LOCATION: (202)..(202)
<223> OTHER INFORMATION: Xaa is an aromatic or basic residue
<220> FEATURE:
<221> NAME/KEY: MISC_FEATURE
<222> LOCATION: (203)..(203)
<223> OTHER INFORMATION: Xaa is a non-polar, aromatic, or aliphatic
      residue
<220> FEATURE:
<221> NAME/KEY: MISC_FEATURE
<222> LOCATION: (205)..(205)
<223> OTHER INFORMATION: Xaa is a polar residue
<220> FEATURE:
<221> NAME/KEY: MISC_FEATURE
<222> LOCATION: (206)..(206)
<223> OTHER INFORMATION: Xaa is an aromatic residue
<220> FEATURE:
<221> NAME/KEY: MISC_FEATURE
<222> LOCATION: (207)..(207)
<223> OTHER INFORMATION: Xaa is a non-polar, aromatic, acidic, or
      aliphatic residue
<220> FEATURE:
<221> NAME/KEY: MISC_FEATURE
<222> LOCATION: (209)..(209)
<223> OTHER INFORMATION: Xaa is an aromatic, acidic, non-polar, polar,
      or aliphatic residue
<220> FEATURE:
<221> NAME/KEY: MISC_FEATURE
<222> LOCATION: (210)..(210)
<223> OTHER INFORMATION: Xaa is a non-polar or aliphatic residue
<220> FEATURE:
<221> NAME/KEY: MISC_FEATURE
<222> LOCATION: (211)..(211)
<223> OTHER INFORMATION: Xaa is an aromatic, acidic, aliphatic, polar,
      or non-polar residue
<220> FEATURE:
<221> NAME/KEY: MISC_FEATURE
<222> LOCATION: (212)..(212)
<223> OTHER INFORMATION: Xaa is a non-polar, aliphatic, acidic, basic,
      or aromatic residue
<220> FEATURE:
<221> NAME/KEY: MISC_FEATURE
<222> LOCATION: (213)..(213)
<223> OTHER INFORMATION: Xaa is an aromatic, basic, acidic, polar,
      non-polar, or aliphatic residue
<220> FEATURE:
<221> NAME/KEY: MISC_FEATURE
<222> LOCATION: (217)..(217)
<223> OTHER INFORMATION: Xaa is a polar or aromatic residue
<220> FEATURE:
<221> NAME/KEY: MISC_FEATURE
<222> LOCATION: (226)..(226)
<223> OTHER INFORMATION: Xaa is an aliphatic residue
<220> FEATURE:
<221> NAME/KEY: MISC_FEATURE
<222> LOCATION: (233)..(233)
<223> OTHER INFORMATION: Xaa is a polar residue
<220> FEATURE:
<221> NAME/KEY: MISC_FEATURE
<222> LOCATION: (250)..(250)
<223> OTHER INFORMATION: Xaa is a non-polar residue
<220> FEATURE:
```

-continued

<221> NAME/KEY: MISC_FEATURE
<222> LOCATION: (252)..(252)
<223> OTHER INFORMATION: Xaa is an aromatic residue

<400> SEQUENCE: 245

Met Thr Asp Arg Leu Lys Gly Lys Val Ala Ile Val Thr Gly Thr
1               5                   10                  15

Xaa Gly Ile Gly Leu Ala Ile Ala Asp Lys Phe Val Glu Glu Gly Ala
            20                  25                  30

Lys Val Val Ile Thr Gly Arg Xaa Ala Asp Val Gly Lys Ala Ala
                35                  40                  45

Lys Ser Ile Gly Gly Thr Asp Val Ile Arg Phe Val Gln His Asp Xaa
    50                  55                  60

Ser Asp Glu Xaa Gly Trp Xaa Lys Leu Phe Thr Thr Glu Glu Ala
65                  70                  75                  80

Phe Gly Pro Val Thr Thr Val Asn Asn Ala Gly Ile Xaa Val Xaa
                85                  90                  95

Lys Ser Val Glu Asp Xaa Thr Thr Glu Glu Trp Arg Lys Xaa Leu Ser
            100                 105                 110

Val Xaa Leu Asp Gly Val Phe Phe Gly Thr Arg Leu Gly Ile Gln Arg
    115                 120                 125

Met Lys Asn Lys Gly Leu Xaa Ala Ser Ile Ile Asn Met Ser Ser Xaa
130                 135                 140

Xaa Gly Xaa Val Xaa Xaa Pro Thr Xaa Gly Ala Tyr Xaa Xaa Ser Lys
145                 150                 155                 160

Gly Ala Val Arg Ile Met Ser Lys Ser Ala Ala Leu Xaa Cys Xaa Leu
                165                 170                 175

Lys Asp Tyr Asp Val Arg Val Asn Thr Val His Pro Gly Xaa Ile Lys
            180                 185                 190

Thr Pro Xaa Xaa Xaa Xaa Xaa Glu Xaa Xaa Xaa Glu Xaa Xaa Xaa Gln
        195                 200                 205

Xaa Xaa Xaa Xaa Xaa Met Gly His Xaa Gly Glu Pro Asn Asp Ile Ala
    210                 215                 220

Trp Xaa Cys Val Tyr Leu Ala Ser Xaa Glu Ser Lys Phe Ala Thr Gly
225                 230                 235                 240

Ala Glu Phe Val Val Asp Gly Gly Xaa Ala Xaa
                245                 250

<210> SEQ ID NO 246
<211> LENGTH: 252
<212> TYPE: PRT
<213> ORGANISM: Artificial Sequence
<220> FEATURE:
<223> OTHER INFORMATION: Synthetic engineered aldo-keto reductase
      variant
<220> FEATURE:
<221> NAME/KEY: MISC_FEATURE
<222> LOCATION: (17)..(17)
<223> OTHER INFORMATION: Xaa is a polar residue
<220> FEATURE:
<221> NAME/KEY: MISC_FEATURE
<222> LOCATION: (40)..(40)
<223> OTHER INFORMATION: Xaa is a basic residue
<220> FEATURE:
<221> NAME/KEY: MISC_FEATURE
<222> LOCATION: (64)..(64)
<223> OTHER INFORMATION: Xaa is an aliphatic residue
<220> FEATURE:
<221> NAME/KEY: MISC_FEATURE
<222> LOCATION: (68)..(68)
<223> OTHER INFORMATION: Xaa is a non-polar or aliphatic residue
<220> FEATURE:

```
<221> NAME/KEY: MISC_FEATURE
<222> LOCATION: (71)..(71)
<223> OTHER INFORMATION: Xaa is a non-polar residue
<220> FEATURE:
<221> NAME/KEY: MISC_FEATURE
<222> LOCATION: (94)..(94)
<223> OTHER INFORMATION: Xaa is a polar, aliphatic, or non-polar residue
<220> FEATURE:
<221> NAME/KEY: MISC_FEATURE
<222> LOCATION: (96)..(96)
<223> OTHER INFORMATION: Xaa is an aliphatic residue
<220> FEATURE:
<221> NAME/KEY: MISC_FEATURE
<222> LOCATION: (102)..(102)
<223> OTHER INFORMATION: Xaa is an acidic or polar residue
<220> FEATURE:
<221> NAME/KEY: MISC_FEATURE
<222> LOCATION: (110)..(110)
<223> OTHER INFORMATION: Xaa is an acidic or aromatic residue
<220> FEATURE:
<221> NAME/KEY: MISC_FEATURE
<222> LOCATION: (114)..(114)
<223> OTHER INFORMATION: Xaa is a non-polar residue
<220> FEATURE:
<221> NAME/KEY: MISC_FEATURE
<222> LOCATION: (135)..(135)
<223> OTHER INFORMATION: Xaa is a basic residue
<220> FEATURE:
<221> NAME/KEY: MISC_FEATURE
<222> LOCATION: (144)..(144)
<223> OTHER INFORMATION: Xaa is a non-polar residue
<220> FEATURE:
<221> NAME/KEY: MISC_FEATURE
<222> LOCATION: (145)..(145)
<223> OTHER INFORMATION: Xaa is an aromatic residue
<220> FEATURE:
<221> NAME/KEY: MISC_FEATURE
<222> LOCATION: (147)..(147)
<223> OTHER INFORMATION: Xaa is a non-polar or aliphatic residue
<220> FEATURE:
<221> NAME/KEY: MISC_FEATURE
<222> LOCATION: (149)..(149)
<223> OTHER INFORMATION: Xaa is a polar residue
<220> FEATURE:
<221> NAME/KEY: MISC_FEATURE
<222> LOCATION: (150)..(150)
<223> OTHER INFORMATION: Xaa is an aromatic or acidic residue
<220> FEATURE:
<221> NAME/KEY: MISC_FEATURE
<222> LOCATION: (153)..(153)
<223> OTHER INFORMATION: Xaa is a polar or aromatic residue
<220> FEATURE:
<221> NAME/KEY: MISC_FEATURE
<222> LOCATION: (157)..(157)
<223> OTHER INFORMATION: Xaa is a non-polar residue
<220> FEATURE:
<221> NAME/KEY: MISC_FEATURE
<222> LOCATION: (158)..(158)
<223> OTHER INFORMATION: Xaa is a non-polar or aliphatic residue
<220> FEATURE:
<221> NAME/KEY: MISC_FEATURE
<222> LOCATION: (175)..(175)
<223> OTHER INFORMATION: Xaa is a polar residue
<220> FEATURE:
<221> NAME/KEY: MISC_FEATURE
<222> LOCATION: (190)..(190)
<223> OTHER INFORMATION: Xaa is a polar, aliphatic, aromatic, or
      non-polar residue
<220> FEATURE:
<221> NAME/KEY: MISC_FEATURE
<222> LOCATION: (195)..(195)
<223> OTHER INFORMATION: Xaa is a non-polar residue
<220> FEATURE:
<221> NAME/KEY: MISC_FEATURE
<222> LOCATION: (196)..(196)
<223> OTHER INFORMATION: Xaa is a polar, basic, non-polar, aromatic, or
      aliphatic residue
<220> FEATURE:
<221> NAME/KEY: MISC_FEATURE
```

```
<222> LOCATION: (197)..(197)
<223> OTHER INFORMATION: Xaa is an aromatic residue
<220> FEATURE:
<221> NAME/KEY: MISC_FEATURE
<222> LOCATION: (198)..(198)
<223> OTHER INFORMATION: Xaa is a polar or non-polar residue
<220> FEATURE:
<221> NAME/KEY: MISC_FEATURE
<222> LOCATION: (199)..(199)
<223> OTHER INFORMATION: Xaa is an acidic residue
<220> FEATURE:
<221> NAME/KEY: MISC_FEATURE
<222> LOCATION: (201)..(201)
<223> OTHER INFORMATION: Xaa is a polar residue
<220> FEATURE:
<221> NAME/KEY: MISC_FEATURE
<222> LOCATION: (202)..(202)
<223> OTHER INFORMATION: Xaa is an aromatic or basic residue
<220> FEATURE:
<221> NAME/KEY: MISC_FEATURE
<222> LOCATION: (203)..(203)
<223> OTHER INFORMATION: Xaa is a non-polar, aromatic, or aliphatic
      residue
<220> FEATURE:
<221> NAME/KEY: MISC_FEATURE
<222> LOCATION: (205)..(205)
<223> OTHER INFORMATION: Xaa is a polar residue
<220> FEATURE:
<221> NAME/KEY: MISC_FEATURE
<222> LOCATION: (206)..(206)
<223> OTHER INFORMATION: Xaa is an aromatic residue
<220> FEATURE:
<221> NAME/KEY: MISC_FEATURE
<222> LOCATION: (207)..(207)
<223> OTHER INFORMATION: Xaa is a non-polar, aromatic, acidic, or
      aliphatic residue
<220> FEATURE:
<221> NAME/KEY: MISC_FEATURE
<222> LOCATION: (209)..(209)
<223> OTHER INFORMATION: Xaa is an aromatic, acidic, non-polar, polar,
      or aliphatic residue
<220> FEATURE:
<221> NAME/KEY: MISC_FEATURE
<222> LOCATION: (210)..(210)
<223> OTHER INFORMATION: Xaa is a non-polar or aliphatic residue
<220> FEATURE:
<221> NAME/KEY: MISC_FEATURE
<222> LOCATION: (211)..(211)
<223> OTHER INFORMATION: Xaa is an aromatic, acidic, aliphatic, polar,
      or non-polar residue
<220> FEATURE:
<221> NAME/KEY: MISC_FEATURE
<222> LOCATION: (212)..(212)
<223> OTHER INFORMATION: Xaa is a non-polar, aliphatic, acidic, basic,
      or aromatic residue
<220> FEATURE:
<221> NAME/KEY: MISC_FEATURE
<222> LOCATION: (213)..(213)
<223> OTHER INFORMATION: Xaa is an aromatic, basic, acidic, polar,
      non-polar, or aliphatic residue
<220> FEATURE:
<221> NAME/KEY: MISC_FEATURE
<222> LOCATION: (217)..(217)
<223> OTHER INFORMATION: Xaa is a polar or aromatic residue
<220> FEATURE:
<221> NAME/KEY: MISC_FEATURE
<222> LOCATION: (226)..(226)
<223> OTHER INFORMATION: Xaa is an aliphatic residue
<220> FEATURE:
<221> NAME/KEY: MISC_FEATURE
<222> LOCATION: (233)..(233)
<223> OTHER INFORMATION: Xaa is a polar residue
<220> FEATURE:
<221> NAME/KEY: MISC_FEATURE
<222> LOCATION: (250)..(250)
<223> OTHER INFORMATION: Xaa is a non-polar residue
<220> FEATURE:
<221> NAME/KEY: MISC_FEATURE
<222> LOCATION: (252)..(252)
```

```
<223> OTHER INFORMATION: Xaa is an aromatic residue

<400> SEQUENCE: 246

Met Thr Asp Arg Leu Lys Gly Lys Val Ala Ile Val Thr Gly Gly Thr
1               5                   10                  15

Xaa Gly Ile Gly Leu Ala Ile Ala Asp Lys Phe Val Glu Glu Gly Ala
                20                  25                  30

Lys Val Val Ile Thr Gly Arg Xaa Ala Asp Val Gly Glu Lys Ala Ala
            35                  40                  45

Lys Ser Ile Gly Gly Thr Asp Val Ile Arg Phe Val Gln His Asp Xaa
        50                  55                  60

Ser Asp Glu Xaa Gly Trp Xaa Lys Leu Phe Asp Thr Thr Glu Glu Ala
65                  70                  75                  80

Phe Gly Pro Val Thr Thr Val Val Asn Asn Ala Gly Ile Xaa Val Xaa
                85                  90                  95

Lys Ser Val Glu Asp Xaa Thr Thr Glu Glu Trp Arg Lys Xaa Leu Ser
                100                 105                 110

Val Xaa Leu Asp Gly Val Phe Phe Gly Thr Arg Leu Gly Ile Gln Arg
        115                 120                 125

Met Lys Asn Lys Gly Leu Xaa Ala Ser Ile Ile Asn Met Ser Ser Xaa
        130                 135                 140

Xaa Gly Xaa Val Xaa Xaa Pro Thr Xaa Gly Ala Tyr Xaa Xaa Ser Lys
145                 150                 155                 160

Gly Ala Val Arg Ile Met Ser Lys Ser Ala Ala Leu Leu Cys Xaa Leu
                165                 170                 175

Lys Asp Tyr Asp Val Arg Val Asn Thr Val His Pro Gly Xaa Ile Lys
            180                 185                 190

Thr Pro Xaa Xaa Xaa Xaa Xaa Glu Xaa Xaa Xaa Glu Xaa Xaa Xaa Gln
        195                 200                 205

Xaa Xaa Xaa Xaa Xaa Met Gly His Xaa Gly Glu Pro Asn Asp Ile Ala
        210                 215                 220

Trp Xaa Cys Val Tyr Leu Ala Ser Xaa Glu Ser Lys Phe Ala Thr Gly
225                 230                 235                 240

Ala Glu Phe Val Val Asp Gly Gly Xaa Ala Xaa
                245                 250
```